United States Patent
Duffy et al.

(10) Patent No.: US 11,619,631 B2
(45) Date of Patent: *Apr. 4, 2023

(54) ULTRA-SENSITIVE DETECTION OF MOLECULES OR PARTICLES USING BEADS OR OTHER CAPTURE OBJECTS

(71) Applicant: Quanterix Corporation, Billerica, MA (US)

(72) Inventors: David C. Duffy, Arlington, MA (US); David M. Rissin, Somerville, MA (US); David R. Walt, Boston, MA (US); David Fournier, Northborough, MA (US); Cheuk Kan, Waltham, MA (US)

(73) Assignee: Quanterix Corporation, Billerica, MA (US)

( * ) Notice: Subject to any disclaimer, the term of this patent is extended or adjusted under 35 U.S.C. 154(b) by 310 days.

This patent is subject to a terminal disclaimer.

(21) Appl. No.: 16/381,614

(22) Filed: Apr. 11, 2019

(65) Prior Publication Data

US 2019/0302109 A1   Oct. 3, 2019

Related U.S. Application Data

(63) Continuation of application No. 15/487,889, filed on Apr. 14, 2017, now Pat. No. 10,725,032, which is a continuation of application No. 15/265,996, filed on Sep. 15, 2016, now abandoned, which is a continuation of application No. 13/530,979, filed on Jun. 22, 2012, now Pat. No. 9,482,662, which is a continuation of application No. 12/731,130, filed on Mar. 24, 2010, now Pat. No. 8,236,574.

(60) Provisional application No. 61/309,141, filed on Mar. 1, 2010.

(51) Int. Cl.
*G01N 33/543* (2006.01)

(52) U.S. Cl.
CPC . *G01N 33/54393* (2013.01); *G01N 33/54306* (2013.01); *G01N 33/54313* (2013.01)

(58) Field of Classification Search
None
See application file for complete search history.

(56) References Cited

U.S. PATENT DOCUMENTS

| | | |
|---|---|---|
| 3,712,986 A | 1/1973 | Collings |
| 4,200,110 A | 4/1980 | Peterson et al. |
| 4,232,119 A | 11/1980 | Carlsson et al. |
| 4,631,211 A | 12/1986 | Houghten |
| 4,780,421 A * | 10/1988 | Kameda ............ C07D 493/10 435/968 |
| 4,883,642 A | 11/1989 | Bisconte |
| 4,907,037 A | 3/1990 | Boisde et al. |
| 4,924,870 A | 5/1990 | Wlodarczyk et al. |
| 4,962,037 A | 10/1990 | Jett et al. |
| 5,026,159 A | 6/1991 | Allen et al. |
| 5,028,535 A | 7/1991 | Buechler et al. |
| 5,089,391 A | 2/1992 | Buechler et al. |
| 5,091,300 A | 2/1992 | Hurni et al. |
| 5,108,961 A | 4/1992 | Zhong et al. |
| 5,152,816 A | 10/1992 | Berkey |
| 5,190,857 A | 3/1993 | Allen et al. |
| 5,196,306 A | 3/1993 | Bobrow et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,315,375 A | 5/1994 | Allen |
| 5,320,814 A | 6/1994 | Walt et al. |
| 5,329,461 A | 7/1994 | Allen et al. |
| 5,374,395 A | 12/1994 | Robinson et al. |
| 5,405,783 A | 4/1995 | Pirrung et al. |
| 5,445,934 A | 8/1995 | Fodor et al. |
| 5,468,846 A | 11/1995 | Ichikawa et al. |
| 5,488,567 A | 1/1996 | Allen et al. |

(Continued)

FOREIGN PATENT DOCUMENTS

| | | |
|---|---|---|
| AU | 199956253 B2 | 3/2000 |
| CN | 1635146 A | 7/2005 |

(Continued)

OTHER PUBLICATIONS

U.S. Appl. No. 15/487,889, filed Apr. 14, 2017, Duffy et al.
U.S. Appl. No. 15/921,429, filed Mar. 14, 2018, Fournier et al.
U.S. Appl. No. 15/808,969, filed Nov. 10, 2017, Rissin et al.
U.S. Appl. No. 14/963,421, filed Dec. 9, 2015, Wilson et al.
U.S. Appl. No. 14/111,331, filed Dec. 18, 2013, Wilson et al.
U.S. Appl. No. 15/269,142, filed Sep. 19, 2016, Wilson et al.
U.S. Appl. No. 15/942,379, filed Mar. 30, 2018, Duffy et al.
U.S. Appl. No. 14/889,982, filed Nov. 9, 2015, Rissin et al.
U.S. Appl. No. 15/543,401, filed Jul. 13, 2017, Duffy et al.
U.S. Appl. No. 16/286,811, filed Feb. 27, 2019, Walt et al.

(Continued)

*Primary Examiner* — Ann Montgomery
(74) *Attorney, Agent, or Firm* — Wolf, Greenfield & Sacks, P.C.

(57) ABSTRACT

The present invention relates to systems and methods for detecting analyte molecules or particles in a fluid sample and in some cases, determining a measure of the concentration of the molecules or particles in the fluid sample. Methods of the present invention may comprise immobilizing a plurality of analyte molecules or particles with respect to a plurality of capture objects. At least a portion of the plurality of capture objects may be spatially separated into a plurality of locations. A measure of the concentration of analyte molecules in a fluid sample may be determined, at least in part, on the number of reaction vessels comprising an analyte molecule immobilized with respect to a capture object. In some cases, the assay may additionally comprise steps including binding ligands, precursor labeling agents, and/or enzymatic components.

20 Claims, 24 Drawing Sheets

(56) References Cited

U.S. PATENT DOCUMENTS

| | | |
|---|---|---|
| 5,512,490 A | 4/1996 | Walt et al. |
| 5,532,138 A | 7/1996 | Singh et al. |
| 5,532,379 A | 7/1996 | Fujimoto |
| 5,545,531 A | 8/1996 | Rava et al. |
| 5,583,001 A | 12/1996 | Bobrow et al. |
| 5,620,850 A | 4/1997 | Bamdad et al. |
| 5,633,972 A | 5/1997 | Walt et al. |
| 5,641,634 A | 6/1997 | Mandecki |
| 5,690,894 A | 11/1997 | Pinkel et al. |
| 5,700,637 A | 12/1997 | Southern |
| 5,731,158 A | 3/1998 | Bobrow et al. |
| 5,770,455 A | 6/1998 | Cargill et al. |
| 5,807,522 A | 9/1998 | Brown et al. |
| 5,814,524 A | 9/1998 | Walt et al. |
| 5,885,529 A * | 3/1999 | Babson ............... B01L 3/50853 422/65 |
| 5,900,481 A | 5/1999 | Lough et al. |
| 5,981,180 A | 11/1999 | Chandler et al. |
| 6,001,564 A | 12/1999 | Bergeron et al. |
| 6,007,690 A | 12/1999 | Nelson et al. |
| 6,013,445 A | 1/2000 | Albrecht et al. |
| 6,023,540 A | 2/2000 | Walt et al. |
| 6,133,436 A | 10/2000 | Koster et al. |
| 6,143,496 A | 11/2000 | Brown et al. |
| 6,156,270 A | 12/2000 | Buechler |
| 6,174,695 B1 | 1/2001 | Hammock et al. |
| 6,210,910 B1 | 4/2001 | Walt et al. |
| 6,266,459 B1 | 7/2001 | Walt et al. |
| 6,285,807 B1 | 9/2001 | Walt et al. |
| 6,327,410 B1 | 12/2001 | Walt et al. |
| 6,329,139 B1 | 12/2001 | Nova et al. |
| 6,368,874 B1 | 4/2002 | Gallop et al. |
| 6,377,721 B1 | 4/2002 | Walt et al. |
| 6,388,746 B1 | 5/2002 | Eriksson et al. |
| 6,396,995 B1 | 5/2002 | Stuelpnagel et al. |
| 6,406,845 B1 | 6/2002 | Walt et al. |
| 6,432,630 B1 * | 8/2002 | Blankenstein ......... B01D 57/02 435/4 |
| 6,450,203 B1 | 9/2002 | Backhouse et al. |
| 6,482,593 B2 | 11/2002 | Walt et al. |
| 6,582,908 B2 | 6/2003 | Fodor et al. |
| 6,589,736 B1 * | 7/2003 | Rothschild ............. C07H 21/00 435/5 |
| 6,599,331 B2 | 7/2003 | Chandler et al. |
| 6,602,702 B1 * | 8/2003 | McDevitt ............. G01N 21/253 422/82.05 |
| 6,620,584 B1 | 9/2003 | Chee et al. |
| 6,635,452 B1 | 10/2003 | Monforte et al. |
| 6,667,159 B1 | 12/2003 | Walt et al. |
| 6,713,309 B1 | 3/2004 | Anderson et al. |
| 6,714,303 B2 | 3/2004 | Ivarsson |
| 6,821,449 B2 | 11/2004 | Caplen et al. |
| 6,838,051 B2 | 1/2005 | Marquiss et al. |
| 6,858,394 B1 | 2/2005 | Chee et al. |
| 6,859,570 B2 | 2/2005 | Walt et al. |
| 6,878,345 B1 | 4/2005 | Astle |
| 6,929,924 B2 | 8/2005 | Bouanani et al. |
| 6,942,968 B1 | 9/2005 | Dickinson et al. |
| 6,943,034 B1 | 9/2005 | Winkler et al. |
| 6,991,939 B2 | 1/2006 | Walt et al. |
| 6,999,657 B2 | 2/2006 | Walt |
| 7,041,481 B2 | 5/2006 | Anderson et al. |
| 7,056,746 B2 | 6/2006 | Seul et al. |
| 7,060,431 B2 | 6/2006 | Chee et al. |
| 7,115,884 B1 | 10/2006 | Walt et al. |
| 7,211,390 B2 | 5/2007 | Rothberg et al. |
| 7,214,640 B2 | 5/2007 | Margetts |
| 7,244,559 B2 | 7/2007 | Rothberg et al. |
| 7,250,267 B2 | 7/2007 | Walt et al. |
| 7,264,929 B2 | 9/2007 | Rothberg et al. |
| 7,348,181 B2 | 3/2008 | Walt et al. |
| 7,480,433 B2 | 1/2009 | Walt et al. |
| 7,572,581 B2 | 8/2009 | Gelfand et al. |
| 7,651,841 B2 | 1/2010 | Song et al. |
| 7,759,062 B2 | 7/2010 | Allawi et al. |
| 7,776,553 B2 | 8/2010 | Love et al. |
| 7,838,250 B1 | 11/2010 | Goix et al. |
| 8,222,047 B2 * | 7/2012 | Duffy ............... G01N 33/54326 436/518 |
| 8,236,574 B2 | 8/2012 | Duffy et al. |
| 8,415,171 B2 | 4/2013 | Rissin et al. |
| 8,460,878 B2 * | 6/2013 | Walt ................ G01N 33/54366 435/7.1 |
| 8,460,879 B2 | 6/2013 | Walt et al. |
| 8,492,098 B2 | 7/2013 | Walt et al. |
| 8,592,221 B2 | 11/2013 | Fraden et al. |
| 8,846,415 B2 | 9/2014 | Duffy et al. |
| 9,110,025 B2 * | 8/2015 | Rissin ............... G01N 21/6452 |
| 9,310,360 B2 | 4/2016 | Duffy et al. |
| 9,333,163 B2 | 5/2016 | Farokhzad et al. |
| 9,395,359 B2 | 7/2016 | Walt et al. |
| 9,482,622 B2 | 11/2016 | Sato et al. |
| 9,482,662 B2 | 11/2016 | Duffy et al. |
| 9,551,663 B2 | 1/2017 | Rissin et al. |
| 9,551,664 B2 * | 1/2017 | Fujita ................ G01N 21/6458 |
| 9,678,068 B2 | 6/2017 | Duffy et al. |
| 9,809,838 B2 | 11/2017 | Walt et al. |
| 9,846,155 B2 * | 12/2017 | Rissin ................ G01N 33/573 |
| 9,932,626 B2 | 4/2018 | Duffy et al. |
| 9,952,237 B2 | 4/2018 | Fournier et al. |
| 10,261,089 B2 | 4/2019 | Walt et al. |
| 10,357,772 B2 | 7/2019 | Fraden et al. |
| 10,393,759 B2 | 8/2019 | Wilson et al. |
| 10,640,814 B2 | 5/2020 | Duffy et al. |
| 10,725,032 B2 | 7/2020 | Duffy et al. |
| 10,960,397 B2 | 3/2021 | Fraden et al. |
| 10,989,713 B2 | 4/2021 | Rissin et al. |
| 11,112,415 B2 | 9/2021 | Fournier et al. |
| 11,187,702 B2 | 11/2021 | Link et al. |
| 11,275,092 B2 | 3/2022 | Wilson et al. |
| 11,434,264 B2 | 9/2022 | Pollock et al. |
| 2002/0009391 A1 | 1/2002 | Marquiss et al. |
| 2002/0090650 A1 | 7/2002 | Empedocles et al. |
| 2002/0122612 A1 | 9/2002 | Walt et al. |
| 2003/0027126 A1 | 2/2003 | Walt et al. |
| 2003/0091475 A1 | 5/2003 | Yu et al. |
| 2003/0096227 A1 | 5/2003 | Shinitzky et al. |
| 2003/0096243 A1 | 5/2003 | Busa |
| 2003/0104361 A1 | 6/2003 | Weininger et al. |
| 2003/0143555 A1 | 7/2003 | Bourget et al. |
| 2003/0143580 A1 | 7/2003 | Straus et al. |
| 2003/0198573 A1 | 10/2003 | Forood et al. |
| 2004/0018561 A1 | 1/2004 | Decrescenzo et al. |
| 2004/0038426 A1 | 2/2004 | Manalis |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0142386 A1 | 7/2004 | Rigler et al. |
| 2004/0248325 A1 * | 12/2004 | Bukusoglu ......... G01N 33/5088 436/548 |
| 2004/0253624 A1 | 12/2004 | Smith et al. |
| 2004/0259237 A1 | 12/2004 | Kellogg et al. |
| 2005/0053996 A1 | 3/2005 | Tong |
| 2005/0112634 A1 | 5/2005 | Woudenberg et al. |
| 2005/0112655 A1 | 5/2005 | Banerjee et al. |
| 2005/0129581 A1 | 6/2005 | McBride et al. |
| 2005/0130173 A1 | 6/2005 | Leamon et al. |
| 2005/0130188 A1 * | 6/2005 | Walt .................... C12Q 1/6837 506/3 |
| 2005/0131650 A1 | 6/2005 | Andersson et al. |
| 2005/0164289 A1 | 7/2005 | Quate et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0255491 A1 * | 11/2005 | Lee .................... G01N 33/6842 435/6.1 |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |

(56) References Cited

U.S. PATENT DOCUMENTS

| | | |
|---|---|---|
| 2006/0078998 A1 | 4/2006 | Puskas et al. |
| 2006/0084183 A1 | 4/2006 | Henricksen |
| 2006/0139635 A1 | 6/2006 | Kersey et al. |
| 2007/0040095 A1 | 2/2007 | Walt et al. |
| 2007/0059754 A1 | 3/2007 | Kordunsky et al. |
| 2007/0074972 A1 | 4/2007 | Nassef et al. |
| 2007/0116607 A1 | 5/2007 | Wang et al. |
| 2007/0259381 A1 | 11/2007 | Rissin et al. |
| 2007/0259385 A1 | 11/2007 | Rissin et al. |
| 2007/0259448 A1 | 11/2007 | Rissin et al. |
| 2008/0032324 A1 | 2/2008 | Walt et al. |
| 2008/0039343 A1 | 2/2008 | Guire et al. |
| 2008/0064113 A1 | 3/2008 | Goix et al. |
| 2008/0248962 A1 | 10/2008 | Kim et al. |
| 2008/0254482 A1 | 10/2008 | Mattoon et al. |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski et al. |
| 2009/0289834 A1 | 11/2009 | Devensky |
| 2009/0307772 A1 | 12/2009 | Markham et al. |
| 2010/0022414 A1 | 1/2010 | Link et al. |
| 2010/0028953 A1 | 2/2010 | Koch et al. |
| 2010/0047773 A1 | 2/2010 | Koch et al. |
| 2010/0075355 A1* | 3/2010 | Duffy .................. G01N 33/543 435/18 |
| 2010/0075407 A1 | 3/2010 | Duffy et al. |
| 2010/0075439 A1* | 3/2010 | Duffy ............... G01N 33/54306 436/518 |
| 2010/0075862 A1 | 3/2010 | Duffy et al. |
| 2010/0140289 A1 | 6/2010 | Knobel et al. |
| 2010/0173394 A1 | 7/2010 | Colston, Jr. et al. |
| 2010/0189338 A1* | 7/2010 | Lin .................... G01N 15/1475 382/133 |
| 2010/0192573 A1 | 8/2010 | Hamilton et al. |
| 2010/0204335 A1 | 8/2010 | Beddingfield et al. |
| 2010/0225913 A1 | 9/2010 | Trainer |
| 2010/0227379 A1 | 9/2010 | Wo et al. |
| 2010/0233734 A1 | 9/2010 | Hobbs |
| 2010/0329929 A1 | 12/2010 | Goix et al. |
| 2011/0037463 A1 | 2/2011 | Bertacco et al. |
| 2011/0183330 A1 | 7/2011 | Lo et al. |
| 2011/0195852 A1 | 8/2011 | Walt et al. |
| 2011/0212462 A1* | 9/2011 | Duffy ................. G01N 33/5306 435/7.1 |
| 2011/0212537 A1 | 9/2011 | Rissin et al. |
| 2011/0212848 A1 | 9/2011 | Duffy et al. |
| 2011/0223585 A1 | 9/2011 | Gullberg et al. |
| 2011/0245097 A1 | 10/2011 | Rissin et al. |
| 2012/0183967 A1 | 7/2012 | Man et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0233905 A1 | 8/2015 | Walt et al. |
| 2015/0353997 A1 | 12/2015 | Duffy et al. |
| 2015/0355182 A1 | 12/2015 | Rissin et al. |
| 2016/0123969 A1 | 5/2016 | Rissin et al. |
| 2016/0258959 A1 | 9/2016 | Wilson et al. |
| 2017/0038390 A1 | 2/2017 | Walt et al. |
| 2017/0159104 A1 | 6/2017 | Walt et al. |
| 2017/0160292 A1 | 6/2017 | Wilson et al. |
| 2018/0003703 A1 | 1/2018 | Duffy et al. |
| 2018/0017552 A1 | 1/2018 | Duffy et al. |
| 2018/0224451 A1 | 8/2018 | Rissin et al. |
| 2018/0306830 A1 | 10/2018 | Fournier et al. |
| 2018/0363038 A1 | 12/2018 | Duffy et al. |
| 2019/0293655 A1 | 9/2019 | Walt et al. |
| 2020/0032326 A1 | 1/2020 | Walt et al. |
| 2020/0123592 A1 | 4/2020 | Díaz-Mochón et al. |
| 2020/0124620 A1 | 4/2020 | Wilson et al. |
| 2020/0271643 A1 | 8/2020 | Wilson et al. |
| 2020/0393457 A1 | 12/2020 | Duffy et al. |
| 2021/0311058 A1 | 10/2021 | Rissin et al. |
| 2022/0034917 A1 | 2/2022 | Fournier et al. |
| 2022/0050108 A1 | 2/2022 | Link et al. |
| 2022/0099678 A1 | 3/2022 | Walt et al. |
| 2022/0205992 A1 | 6/2022 | Rissin et al. |
| 2022/0229074 A1 | 7/2022 | Wilson et al. |
| 2022/0244276 A1 | 8/2022 | Wilson et al. |

FOREIGN PATENT DOCUMENTS

| | | |
|---|---|---|
| CN | 1928561 A | 3/2007 |
| CN | 1950520 A | 4/2007 |
| CN | 101351564 A | 1/2009 |
| CN | 101529227 A | 9/2009 |
| CN | 101541974 A | 9/2009 |
| DE | 19540098 A1 | 4/1997 |
| EP | 0 805 215 A2 | 11/1997 |
| EP | 1 180 679 A1 | 2/2002 |
| EP | 1 259 810 A2 | 11/2002 |
| EP | 1 721 657 A1 | 11/2006 |
| EP | 2 267 451 A2 | 12/2010 |
| JP | 2001-269196 A | 10/2001 |
| JP | 2002-506200 A | 2/2002 |
| JP | 2002-525587 A | 8/2002 |
| JP | 2004-354164 A | 12/2004 |
| JP | 2005-518553 A | 6/2005 |
| JP | 2006-511792 A | 4/2006 |
| WO | WO 88/05533 A1 | 7/1988 |
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 02/077646 A1 | 10/2002 |
| WO | WO 03/54142 A2 | 7/2003 |
| WO | WO 03/73817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2005/095262 A1 | 10/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109364 A2 | 9/2011 |
| WO | WO 2011/109372 A1 | 9/2011 |
| WO | WO 2016/115256 A1 | 7/2016 |

(56) References Cited

FOREIGN PATENT DOCUMENTS

| WO | WO 2016/130923 A1 | 8/2016 |
| WO | WO 2018/222585 A2 | 12/2018 |
| WO | WO 2019/060607 A1 | 3/2019 |

OTHER PUBLICATIONS

Office Communication for U.S. Appl. No. 12/236,484, filed Sep. 23, 2008, published as US 2010-0075862, which Office Communication is dated Apr. 13, 2011, and claims as pending for U.S. Appl. No. 12/236,484 as of Apr. 13, 2011.
Office Communication dated for U.S. Appl. No. 12/236,484, filed Sep. 23, 2008, published as US 2010-0075862, which Office Communication is dated Sep. 9, 2010, and claims as pending for U.S. Appl. No. 12/236,484 as of Sep. 9, 2010.
International Preliminary Report on Patentability, Chapter 1, for International Application No. PCT/US2009/005250, dated Apr. 7, 2011.
International Search Report for International Application No. PCT/US2009/005250, dated Mar. 22, 2010.
Office Communication for U.S. Appl. No. 12/236,486, filed Sep. 23, 2008, published as US 2010-0075407, which Office Communication is dated Nov. 23, 2011, and claims as pending for U.S. Appl. No. 12/236,486 as of Nov. 23, 2011.
Notice of Allowance for U.S. Appl. No. 12/236,486, filed Sep. 23, 2008, published as US 2010-0075407 on Mar. 25, 2010, which Notice of Allowance is dated Mar. 22, 2012, and claims as pending for U.S. Appl. No. 12/236,486 as of Mar. 22, 2012.
Office Communication for U.S. Appl. No. 13/527,210, filed Jun. 19, 2012, which Office Communication is dated Jun. 20, 2013, and claims as pending for Office Communication for U.S. Appl. No. 13/527,210 as of Jun. 20, 2013.
Office Communication for U.S. Appl. No. 13/527,210, filed Jun. 19, 2012, which Office Communication is dated Feb. 6, 2014, and claims as pending for Office Communication for U.S. Appl. No. 13/527,210 as of Nov. 20, 2013.
Notice of Allowance for U.S. Appl. No. 13/527,210, filed Jun. 19, 2012, which Notice of Allowance is dated May 27, 2014, and claims as pending for U.S. Appl. No. 13/527,210 as of Nov. 20, 2013.
International Preliminary Report on Patentability, Chapter 1, for International Application No. PCT/US2009/005248, dated Apr. 7, 2011.
International Search Report for International Application No. PCT/US2009/005248, dated Mar. 1, 2010.
Office Communication for U.S. Appl. No. 12/236,488, filed Sep. 23, 2008, published as US 2010-0075439, which Office Communication is dated Aug. 2, 2010, and claims as pending for U.S. Appl. No. 12/236,488 as of Aug. 2, 2010.
Office Communication for CA Application No. 2791654, filed Mar. 1, 2011, which Office Communication is dated Aug. 21, 2013, and claims as pending for CA Application No. 2791654.
Office Communication for CA Application No. 2,791,654, filed Mar. 1, 2011, which Office Communication is dated Mar. 18, 2014, and claims as pending for CA Application No. 2,791,654.
Office Communication for CN Application No. 201180019462.2, filed Mar. 1, 2011, which Office Communication is dated Sep. 23, 2013, and claims as pending for CN Application No. 201180019462.2.
Office Communication for CN Application No. 201180019462.2, filed Mar. 1, 2011, which Office Communication is dated Dec. 26, 2013, and claims as pending for CN Application No. 201180019462.2.
Office Communication for CN Application No. 201180019462.2, filed Mar. 1, 2011, which Office Communication is dated Jul. 10, 2014, and claims as pending for CN Application No. 201180019462.2 as of May 13, 2014.
Office Communication for CN Application No. 201180019462.2, filed Mar. 1, 2011, which Office Communication is dated Nov. 21, 2014, and claims as pending for CN Application No. 201180019462.2 as of May 13, 2014.

Notification of Grant for CN Application No. 201180019462.2, filed Mar. 1, 2011, which Notification of Grant is dated Mar. 5, 2015, and claims as granted for CN Application No. 201180019462.2.
Office Communication for CN Application No. 201510256620.6, filed May 20, 2015, which Office Communication is dated Apr. 1, 2016, and claims as pending for CN Application No. 201510256620.6 as of Nov. 25, 2015.
Office Communication for EP Application No. 11730109.3, filed Mar. 1, 2011, which Office Communication is dated Jul. 15, 2013, and claims as pending for EP Application No. 11730109.3 as of Jul. 15, 2013.
Office Communication for EP Application No. 11730109.3, filed Mar. 1, 2011, published as EP 2542891, which Office Communication is dated Nov. 28, 2013, and claims as pending for EP Application No. 11730109.3.
Office Communication for EP Application No. 11730109.3, filed Mar. 1, 2011, which Office Communication is dated Jun. 25, 2014, and claims as pending for EP Application No. 11730109.3 as of Apr. 8, 2014.
Intention to Grant for EP Application No. 11730109.3, filed Mar. 1, 2011, which Intention to Grant is dated Nov. 12, 2014, and claims as granted for EP Application No. 11730109.3.
Extended European Search Report for European Application No. 15168213.5 dated Feb. 15, 2016.
Extended European Search Report for European Application No. 17201287.4 dated Mar. 21, 2018, and claims pending.
Office Communication for EP App. No. 17 201 287.4 dated Feb. 4, 2019 and claims as pending.
Translation of Office Communication for JP Application No. 2012-556164, filed Mar. 1, 2011, which Office Communication is dated Aug. 6, 2013, and translated claims as pending for JP Application No. 2012-556164 as of Aug. 6, 2013.
Office Communication for JP Application No. 2012-556164, filed Mar. 1, 2011, which Office Communication is dated Apr. 22, 2014, and claims as allowed for JP Application No. 2012-556164.
Office Communication for JP Application No. 2014-105431, filed Mar. 1, 2011, which Office Communication is dated Feb. 10, 2015, and claims as filed for JP Application No. 2014-105431.
Office Communication for U.S. Appl. No. 12/731,130, filed Mar. 24, 2020, published as US 2011-0212848 on Sep. 1, 2011, which Office Communication is dated Mar. 28, 2012, and claims as pending for U.S. Appl. No. 12/731,130 as of Mar. 28, 2012.
Notice of Allowance for U.S. Appl. No. 12/731,130, filed Mar. 24, 2010, published as US 2011-0212848 on Sep. 1, 2011, which Notice of Allowance is dated Jun. 1, 2012, and allowed claims for U.S. Appl. No. 12/731,130 as of Jun. 1, 2012.
Office Communication for U.S. Appl. No. 13/530,979, filed Jun. 22, 2012, which Office Communication is dated Jun. 19, 2015, and claims as pending for U.S. Appl. No. 13/530,979 as of Apr. 5, 2013.
Office Communication for U.S. Appl. No. 13/530,979, filed Jun. 22, 2012, which Office Communication is dated Jan. 22, 2016, and claims as pending for U.S. Appl. No. 13/530,979 as of Dec. 9, 2015.
Office Communication for U.S. Appl. No. 13/530,979, filed Jun. 22, 2012, which Office Communication is dated Jan. 28, 2016, and claims as pending for U.S. Appl. No. 13/530,979 as of Dec. 9, 2015.
Office Communication for U.S. Appl. No. 13/531,061, filed Jun. 22, 2012, which Office Communication is dated Aug. 21, 2015, and claims as pending for U.S. Appl. No. 13/531,061 as of Apr. 5, 2015.
International Search Report and Written Opinion for International Application No. PCT/US2011/026645, dated Nov. 24, 2011.
International Preliminary Report on Patentability for PCT/US2011/026645 dated Sep. 13, 2012.
Office Communication for U.S. Appl. No. 12/731,135, filed Mar. 24, 2010, published as US 20110212462, which Office Communication is dated May 23, 2013, and claims as pending for U.S. Appl. No. 12/731,135 as of May 23, 2013.
Office Communication for U.S. Appl. No. 12/731,135, filed Mar. 24, 2010, which Office Communication is dated Apr. 3, 2015, and claims as pending for U.S. Appl. No. 12/731,135.
Office Communication for U.S. Appl. No. 12/731,135, filed Mar. 4, 2010, which Office Communication is dated Mar. 29, 2016, and claims as pending for U.S. Appl. No. 12/731,135 as of Sep. 3, 2015.

(56) References Cited

OTHER PUBLICATIONS

International Search Report and Written Opinion for International Application No. PCT/US2011/026657, dated May 24, 2011.
International Preliminary Report on Patentability for PCT/US2011/026657 dated Sep. 13, 2012.
Office Communication for U.S. Appl. No. 12/731,136, filed Mar. 24, 2010, published as US 2011-0212537 on Sep. 1, 2011, which Office Communication is dated Jun. 15, 2012, and claims as pending for U.S. Appl. No. 12/731,136 as of Jun. 15, 2012.
Notice of Allowance for U.S. Appl. No. 12/731,136, filed Mar. 24, 2010, published as 2011-0212537, which Notice of Allowance is dated Nov. 15, 2012, and claims as allowed for U.S. Appl. No. 12/731,136 as of Nov. 15, 2012.
Office Communication for U.S. Appl. No. 13/768,843, filed Feb. 15, 2013, which Office Communication is dated Jan. 29, 2016, and claims as pending for U.S. Appl. No. 13/768,843 as of May 20, 2013.
International Search Report and Written Opinion for International Application No. PCT/US2011/026665, dated Jul. 5, 2011.
International Preliminary Report on Patentability for International Application No. PCT/US2011/026665 dated Sep. 13, 2012.
Office Communication for U.S. Appl. No. 13/035,472, filed Feb. 25, 2011, which Office Communication is dated Mar. 20, 2014, and claims as pending for U.S. Appl. No. 13/035,472.
International Search Report and Written Opinion for International Application No. PCT/US2012/022923 dated Jun. 25, 2012.
Invitation to Pay Additional Fees for International Application No. PCT/US2012/022923 dated Apr. 2, 2012.
International Preliminary Report on Patentability for International Application No. PCT/US2012/022923 dated Aug. 8, 2013.
Office Communication for U.S. Appl. No. 13/037,987, which Office Communication is dated May 2, 2014, and claims as pending for U.S. Appl. No. 13/037,987.
Office Communication for U.S. Appl. No. 13/037,987, filed Mar. 1, 2011, which Office Communication is dated Oct. 20, 2014, and claims as pending for U.S. Appl. No. 13/037,987 as of Jul. 2, 2014.
International Preliminary Report on Patentability, Chapter 1, for International Application No. PCT/US2007/019184, dated Mar. 11, 2010.
International Search Report and Written Opinion for International Application No. PCT/US2007/019184, dated Jun. 19, 2008.
European Search Report for Application No. 07751131.9 dated Sep. 8, 2009.
Extended European Search Report for European Application No. 12177276.8 dated Nov. 26, 2012.
Office Communication for U.S. Appl. No. 11/707,385, filed Feb. 16, 2007, published as US-2007-0259448, which Office Communication is dated Jan. 26, 2010, and claims as pending for Office Communication for U.S. Appl. No. 11/707,385 as of Jan. 26, 2010.
Office Communication for U.S. Appl. No. 11/707,385, filed Feb. 16, 2007, published as US 2007-0259448, which Office Action is date Mar. 16, 2009, and claims as pending for U.S. Appl. No. 11/707,385 as of Mar. 16, 2009.
Office Communication for U.S. Appl. No. 11/707,385, filed Feb. 16, 2007, published as US 2007-0259448, which Office Communication is dated Sep. 27, 2012, and claims as pending for U.S. Appl. No. 11/707,385 as of Sep. 27, 2012.
Notice of Allowance for U.S. Appl. No. 11/707,385, filed Feb. 16, 2007, published as US-2007-0259448, which Notice of Allowance is dated Feb. 25, 2013, and claims as allowed for Office Communication for U.S. Appl. No. 11/707,385 as of Feb. 25, 2013.
Office Communication for U.S. Appl. No. 11/707,383, filed Feb. 16, 2007, published as US 2007-0259385, which Office Communication is dated Mar. 16, 2009, and claims as pending for Office Communication for U.S. Appl. No. 11/707,383, as of Mar. 16, 2009.
Office Communication for U.S. Appl. No. 11/707,383, filed Feb. 16, 2007, published as US 2007-0259385, which Office Communication is dated Nov. 27, 2009, and claims as pending for Office Communication for U.S. Appl. No. 11/707,383 as of Nov. 27, 2009.
Office Communication for U.S. Appl. No. 11/707,383, filed Feb. 16, 2007, published as US 2007-0259385, which Office Communication is dated Sep. 27, 2012, and claims as pending for U.S. Appl. No. 11/707,383 as of Sep. 27, 2012.
Notice of Allowance for U.S. Appl. No. 11/707,383, filed Feb. 16, 2007, published as US 2007-0259385, which Office Communication is dated Feb. 8, 2013, and claims as allowed for U.S. Appl. No. 11/707,383 as of Feb. 8, 2013.
Office Communication for U.S. Appl. No. 11/707,384, filed Feb. 16, 2007, published as US 2007-0259381, which Office Communication is dated Dec. 2, 2009, and claims as pending for Office Communication for U.S. Appl. No. 11/707,384 as of Dec. 2, 2009.
Office Communication for U.S. Appl. No. 11/707,384, filed Feb. 16, 2007, published as US 2007-0259381, which Office Communication is dated Mar. 16, 2009, and claims as pending for Office Communication for U.S. Appl. No. 11/707,384 as of Mar. 16, 2009.
Office Communication for U.S. Appl. No. 11/707,384, filed Feb. 16, 2007, published as US 2007-0259381, which Office Communication is dated Sep. 27, 2012, and claims as pending for U.S. Appl. No. 11/707,384 as of Sep. 27, 2012.
Notice of Allowance for U.S. Appl. No. 11/707,384, filed Feb. 16, 2007, published as US 2007-0259381, which Office Communication is dated Feb. 6, 2013, and claims as allowed for U.S. Appl. No. 11/707,384 as of Feb. 6, 2013.
International Preliminary Report on Patentability, Chapter 1, for International Application No. PCT/US2007/004349 dated Sep. 25, 2008.
International Preliminary Report on Patentability, Chapter 2, for International Application No. PCT/US2007/004349 dated Mar. 23, 2009.
International Search Report and Written Opinion for International Application No. PCT/US2007/04349, dated Aug. 21, 2008.
[No Author Listed], bioMérieux and Quanterix Sign Strategic Partnership in Ultrasensitive and Multiplex Immunoassays. Quanterix Press Release. Nov. 15, 2012. 2 pages.
[No Author Listed], Does Brain Hypoxia Help Kick Off Alzheimer's Pathology? Alzheimer Research Forum. Dec. 16, 2011. http://www.alzforum.org/new/detailprint.asp?id=3002 [last accessed Jan. 30, 2012]. 4 pages.
[No Author Listed], Novel test following prostate surgery could detect cancer recurrence earlier. AACR Press Release. Sep. 2, 20109. Last accessed at http://www.aacr.org/home/public--media/aacr-press-releases.aspx?d=2072 on Jan. 31, 2012. 2 pages.
[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last Accessed Jan. 31, 2012]. 2 pages.
[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed], Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed], Quanterix Digital ELISA Measures Low Abundance Biomarkers of Inflammation in Crohn's Disease. Quanterix Press Release. Aug. 19, 2011. Last accessed at http://www.quanterix.com/events-news/press-releases/item/142-quanterix-digital-elisa-measures-low-abundance-biomarkers-of-inflammation-in-crohn's-disease on Sep. 20, 2012.
[No Author Listed], Quanterix Launches Multiplexed Single Molecule Immunoassay Technology to Improve Diagnosis and Potential Treatment of Complex Diseases. Quanterix Press Release. Sep. 17, 2013. 2 pages.

(56) References Cited

OTHER PUBLICATIONS

[No Author Listed], Quanterix to Present Poster Session on Blood-based Brain Biomarker Measurements of Sports Related Brain Injury at Neuroscience. Quanterix Press Release. Nov. 4, 2013. 1 page.

[No Author Listed], Quanterix's Simoa technology to detect blood biomarker for concussion in hockey players. Quanterix Press Release. Mar. 14, 2014. 1 page.

[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.

[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.

[No Author Listed], Scientific Principle of Simoa™ (Single Molecule Array) Technology. Whitepaper 1.0. Jul. 19, 2013. 2 pages.

[No Author Listed], Single molecule arrays for digital detection in complex samples. Quanterix Corporation. IQT Technology Focus Day. Mar. 25, 2010. PowerPoint presentation. 30 pages.

Adams et al., Encoded fiber-optic microsphere arrays for probing protein-carbohydrate interactions. Angewandte Chemie. 2003; 115:5475-5478.

Agrawal et al., Nanometer-scale mapping and single-molecule detection with color-coded nanoparticle probes. Proc Natl Acad Sci USA. Mar. 4, 2008;105(9):3298-303. Epub Feb. 27, 2008.

Agrawal et al., Single-bead immunoassays using magnetic microparticles and spectral-shifting quantum dots. J Agric Food Chem. May 17, 2007; 55(10):3778-82. Epub Apr. 25, 2007.

Ahn et al., Detection of *Salmonella* spp. Using microsphere-based, fiber-optic DNA microarrays. Anal Chem. Aug. 1, 2005; 77(15):5041-7.

Ahn et al., Fiber-optic microarray for simultaneous detection of multiple harmful algal bloom species. Appl Environ Microbiol. Sep. 2006; 72(9):5742-9.

Albert et al., Automatic decoding of sensor types within randomly ordered, high-density optical sensor arrays. Anal Bioanal Chem. Apr. 2002; 373(8):792-802. Epub Jul. 27, 2002.

Albert et al., Cross-reactive chemical sensor arrays. Chem Rev. Jul. 12, 2000; 100(7):2595-626.

Albert et al., Information coding in artificial olfaction ultisensory arrays. Anal Chem. Aug. 15, 2003; 75(16):4161-7.

Albert et al., Optical multibead arrays for simple and complex odor discrimination. Anal Chem. Jun. 1, 2001; 73(11):2501-8.

Angenendt et al., Subnanoliter enzymatic assays on microarrays. Proteomics. Feb. 2005;5(2):420-5.

Arnaud, Observing single enzymes at work. Chemical & Engineering News. Oct. 2007; 85(44):8.

Beer et al., On-chip, real-time, single-copy polymerase chain reaction in picoliter droplets. Anal Chem. Nov. 15, 2007;79(22):8471-5. Epub Oct. 11, 2007. Abstract only.

Bencic-Nagale et al., Extending the longevity of fluorescence-based sensor arrays using adaptive exposure. Anal Chem. Oct. 1, 2005; 77(19):6155-62.

Bhat et al., Single molecule detection in nanofluidic digital array enables accurate measurement of DNA copy number Anal Bioanal Chem. May 2009;394(2):457-67. Epub Mar. 15, 2009.

Biran et al., Optical imaging fiber-based live bacterial cell array biosensor. Anal Biochem. Apr. 1, 2003;315(1):106-13.

Biran et al., Optical imaging fiber-based single live cell arrays: a high-density cell assay platform. Anal Chem. Jul. 1, 2002; 74(13):3046-54.

Blake et al., Phenotypic consequences of promoter-mediated transcriptional noise. Mol Cell. Dec. 28, 2006; 24(6):853-65.

Blicharz et al., Detection of inflammatory cytokines using a fiber optic microsphere immunoassay array. *Proc. SPIE*. 2006; 6380, 638010-1-638010-6.

Blicharz et al., Fiber-optic microsphere-based antibody array for the analysis of inflammatory cytokins in saliva. Anal. Chem. 2009;81(6):2106-14.

Blicharz et al., Use of colorimetric test strips for monitoring the effect of hemodialysis on salivary nitrite and uric acid in patients with end-stage renal disease: a proof of principle. Clin Chem. Sep. 2008; 54(9): 1473-80. Epub Aug. 1, 2008.

Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.

Bowden et al., Development of a microfluidic platform with an optical imaging microarray capable of attomolar target DNA detection. Anal Chem. Sep. 1, 2005; 77(17):5583-8.

Boyden, The chemotactic effect of mixtures of antibody and antigen on polymorphonuclear leucocytes. J Exp Med. Mar. 1, 1962;115:453-66.

Brehm-Stecher et al., Single-cell microbiology: tools, technologies, and applications. Microbiol Mol Biol Rev. Sep. 2004; 68(3):538-59.

Brogan et al., Optical fiber-based sensors: application to chemical biology. Curr Opin Chem Biol. Oct. 2005; 9(5):494-500.

Bronk et al., Combined imaging and chemical sensing using a single optical imaging fiber. Anal Chem. Sep. 1, 1995; 67(17):2750-7.

Bronk et al., Fabrication of patterned sensor arrays with aryl azides on a polymer-coated imaging optical fiber bundle. Anal Chem. Oct. 15, 1994; 66(20):3519-20.

Burton et al., A microfluidic chip-compatible bioassay based on single-molecule detection with high sensitivity and multiplexing. Lab Chip. Apr. 7, 2010; 10(7):843-51. Epub Jan. 14, 2010.

Campian, Colored and fluorescent solid supports. Innovation and Perspectives in Solid Phase Synthesis. Ed. R. Epton, Mayflower Worldwide Limited, Birmingham. Ch. 77. 1994:469-472.

Chang et al., Digital ELISA of HIV P24 capsid protein with sensitivity of nucleic acid amplification tests. 2012 AACC Meeting. Los Angeles, CA. Abstract and Poster. 2012. 2 pages.

Chang et al., Prototype digital immunoassay for troponin I with sub-femtomolar sensitivity. 2013 AACC Meeting. Houston, TX. Abstract and Poster. 2013. 2 pages.

Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.

Chang et al., Single molecule enzyme-linked immunosorbent assays: theoretical considerations. J Immunol Methods. Apr. 30, 2012;378(1-2): 102-15. doi: 10.1016/j.jim.2012.02.011. Epub Apr. 30, 2013. 28 pages.

Chen et al., Microfabricated arrays of cylindrical wells facilitate single-molecule enzymology of alpha-chymotrypsin. Biotechnol Prog. Jul.-Aug. 2009;25(4):929-37.

Chin et al., Editor's Choice: Distinctive individualism. Science. Apr. 4, 2008;320:21.

Chon et al., Characterization of single-cell migration using a computer-aided fluorescence time-lapse videomicroscopy system. Anal Biochem. Oct. 15, 1997;252(2):246-54.

Deutsch et al., Apparatus for high-precision repetitive sequential optical measurement of living cells. Cytometry. Jul. 1, 1994; 16(3):214-26.

Dicesare et al., Individual cell migration analysis using fiber-optic bundles. Anal Bioanal Chem. May 2005; 382(1):37-43. Epub Apr. 1, 2005.

Dickinson et al., A chemical-detecting system based on a cross-reactive optical sensor array. Nature. Aug. 22, 1996; 382(6593):697-700.

Dickinson et al., Convergent, self-encoded bead sensor arrays in the design of an artificial. Anal Chem. Jun. 1, 1999; 71(11):2192-8.

Dickinson et al., Current trends in 'artificial-nose' technology. Trends Biotechnol. Jun. 1998; 16(6):250-8.

Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.

(56) References Cited

OTHER PUBLICATIONS

Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.
Duffy, Single Molecule Arrays (Simoa) for Ultrasensitive Protein Detection in Companion Diagnostics. Next Generation DX Summit. Aug. 22, 2012. PowerPoint presentation. 36 slides.
Duffy, Ultra-sensitive protein detection using single molecule arrays (Simoa): the potential for detecting single molecules of botulinum toxin. The Botulinum J. 2012;2(2):164-7.
Egner et al., Tagging in combinatorial chemistry: the use of coloured and flurorescent beads. ChemCommun. 1997; 735-736.
Eid et al., Real-time DNA sequencing from single polymerase molecules. Science. Jan. 2, 2009; 323(5910):133-8. Epub Nov. 20, 2008.
Ekins et al., Single-molecule ELISA. Clin Chem. Mar. 2011;57(3):372-5. Epub Oct. 13, 2010. Papers in press. Oct. 13, 2010. pp. 1-3.
English et al., Ever-fluctuating single enzyme molecules: Michaelis-Menten equation revisited. Nat Chem Biol. Feb. 2006; 2(2):87-94. Epub Dec. 25, 2005.
Epstein et al., Combinatorial decoding: an approach for universal DNA array fabrication. J Am Chem Soc. Nov. 12, 2003; 125(45):13753-9.
Epstein et al., Fluorescence-based nucleic acid detection and microarrays. Analytica Chimica Acta. 2002; 469:3-36.
Epstein et al., High-density fiber-optic genosensor microsphere array capable of zeptomole detection limits. Anal Chem. Apr. 15, 2002; 74(8):1836-40.
Epstein et al., High-density, microsphere-based fiber optic DNA microarrays. Biosens Bioelectron. May 2003; 18(5-6):541-6.
Epstein, et al., Fluorescence-based fibre optic arrays: a universal platform for sensing. Chem Soc Rev. Jul. 2003; 32(4):203-14.
Ferguson et al., A fiber-optic DNA biosensor microarray for the analysis of gene expression. Nat Biotechnol. Dec. 1996; 14(13):1681-4.
Ferguson et al., High-density fiber-optic DNA random microsphere array. Anal Chem. Nov. 15, 2000; 72(22):5618-24.
Ferguson et al., Simultaneous monitoring of pH, $CO_2$ and $O_2$ using an optical imaging fiber. Analytica Chimica Acta. 1997; 340(1-3):123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. Clin Chem. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. J Am Chem Soc. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. Proc Natl Acad Sci USA. Nov. 6, 2007; 104(45):17680-5. Epub Oct. 26, 2007.
Härma et al., Europium nanoparticles and time-resolved fluorescence for ultrasensitive detection of prostate-specific antigen. Clin Chem. Mar. 2001; 47(3):561-8.
Härma et al., Miniature single-particle immunoassay for prostate-specific antigen in serum using recombinant Fab fragments. Clin Chem. Nov. 2000; 46(11):1755-61.
Härma et al., Zeptomole detection sensitivity of prostate-specific antigen in a rapid microtitre plate assay using time-resolved fluorescence. Luminescence. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.
Haugland, Handbook: A Guide to Fluorescent Probes and Labeling Technologies. Invitrogen, Eugene, OR. Molecular Probes, US. 2005. pp. 473-538.
He et al., Selective encapsulation of single cells and subcellular organelles into picoliter- and femtoliter-vol. droplets. Anal Chem. Mar. 15, 2005; 77(6):1539-44.
Healey et al., Fiberoptic DNA sensor array capable of detecting point mutations. Anal Biochem. Sep. 5, 1997; 251(2):270-9.
Healey et al., Multianalyte biosensors on optical imaging bundles. Biosens Bioelectron. 1997;12(6):521-9.
Healey et al., Photodeposition of micrometer-scale polymer patterns on optical imaging fibers. Science. Aug. 25, 1995; 269(5227):1078-80.
Hindson et al., High-throughput droplet digital PCR system for absolute quantitation of DNA copy number. Anal Chem. Nov. 15, 2011;83(22):8604-10. Epub Oct. 28, 2011.
Hirano et al., A novel method for DNA molecular counting. Nucleic Acids Symp Ser. 2000;(44):157-8.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. Anal Biochem. Sep. 1989; 181(2):360-70.
Johnson et al., Identification of multiple analytes using an optical sensor array and pattern recognition neural networks. Analytical Chemistry. 1997; 69(22):4641-4648.
Joos, Quanterix Web Symposium: Immunoassays in Multiplex for Biomarker Discovery and Validation. Presentation. Feb. 27, 2013. 43 pages.
Kiss et al., High-throughput quantitative polymerase chain reaction in picoliter droplets. Anal Chem. Dec. 1, 2008;80(23):8975-81.
Kremsky et al., Immobilization of DNA via oligonucleotides containing an aldehyde or carboxylic acid group at the 5' terminus. Nucleic Acids Res. Apr. 10, 1987; 15(7):2891-909.
Kuang et al., Living bacterial cell array for genotoxin monitoring. Anal Chem. May 15, 2004; 76(10):2902-9.
Kuang et al., Monitoring "promiscuous" drug effects on single cells of multiple cell types. Anal Biochem. Oct. 15, 2005; 345(2):320-5.
Kuang et al., Simultaneously monitoring gene expression kinetics and genetic noise in single cells by optical well arrays. Anal Chem. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. Anal Biochem. Jun. 15, 2000; 282(1):142-6.
Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci USA. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10, 1999; 273(2):168-78.

(56) References Cited

OTHER PUBLICATIONS

Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004; 126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Morrison et al., Nanoliter high throughput quantitative PCR. Nucleic Acids Res. 2006;34(18):e123. Epub Sep. 25, 2006.
Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90.
Okrongly, Single Molecule Enzyme Detection and Application to Immunoassay: Implications for Personalized Medicine. Abstract and Presentation. ISE International Conference. May 4, 2010. 24 pages.
Panova et al., In situ fluorescence imaging of localized corrosion with a pH-sensitive imaging fiber. Anal Chem. Apr. 15, 1997; 69(8):1635-41.
Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. Anal Chem. May 1980; 52(6):864-9.
Prabhakar et al., Simultaneous quantification of proinflammatory cytokines in human plasma using the LabMAP assay. J Immunol Methods. Feb. 1, 2002;260(1-2):207-18.
Qiu et al., Fluorescence single-molecule counting assays for high-sensitivity detection of cytokines and chemokines. Clin Chem. Nov. 2007;53(11):2010-2.
Randle et al., Integrating molecular detection and response to create self-signalling antibodies. Biochem Biophys Res Commun. Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Digital concentration readout of single enzyme molecules using femtoliter arrays and Poisson statistics. Nano Lett. Mar. 2006; 6(3):520-3.
Rissin et al., Digital readout of target binding with attomole detection limits via enzyme amplification in femtoliter arrays. J Am Chem Soc. May 17, 2006; 128(19):6286-7.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. Anal Chim Acta. Mar. 30, 2006; 564(1):34-9. Epub Nov. 11, 2005.
Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.
Rissin et al., Multiplexed single molecule immunoassays. Lab Chip. Aug. 7, 2013;13(15):2902-11. doi: 10.1039/c3lc50416f.
Rissin et al., Simultaneous detection of single molecules and singulated ensembles of molecules enables immunoassays with broad dynamic range. Anal Chem. Mar. 15, 2011;83(6):2279-85. Epub Feb. 23, 2011.
Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.
Roeffaers et al., Single-molecule fluorescence spectroscopy in (bio)catalysis. Proc Natl Acad Sci USA. Jul. 31, 2007; 104(31):12603-9. Epub Jul. 30, 2007.
Rondelez et al., Highly coupled ATP synthesis by F1-ATPase single molecules. Nature. Feb. 17, 2005; 433(7027):773-7.
Rondelez et al., Microfabricated arrays of femtoliter chambers allow single molecule enzymology. Nat Biotechnol. Mar. 2005; 23(3):361-5. Epub Feb. 20, 2005.
Rotman, Measurement of activity of single molecules of beta-D-galactosidase. Proc Natl Acad Sci USA. Dec. 15, 1961; 47:1981-91.
Schauer et al., A cross-reactive, class-selective enzymatic array assay. J Am Chem Soc. Sep. 26, 2001; 123(38):9443-4.
Schmidinger, et al., Inhibitor and protein microarrays for activity-based recognition of lipolytic enzymes. Chembiochem. Mar. 2006; 7(3):527-34.
Schweitzer et al., Inaugural article: immunoassays with rolling circle DNA amplification: a versatile platform for ultrasensitive antigen detection. Proc Natl Acad Sci USA. Aug. 29, 2000; 97(18):10113-9.
Seydack, Nanoparticle labels in immunosensing using optical detection methods. Biosens Bioelectron. Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.
Shephard et al., Array-based binary analysis for bacterial typing. Anal Chem. Jan. 1, 2005; 77(1):319-26.
Song et al., Detecting biological warfare agents. Emerg Infect Dis. Oct. 2005; 11(10):1629-32.
Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.
Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013. Supporting information included.
Song et al., Fiber-optic microsphere-based arrays for multiplexed biological warfare agent detection. Anal Chem. Feb. 15, 2006; 78(4):1023-33.
Song et al., Single molecule measurements of tumor necrosis factor α andinterleukin-6 in the plasma of patients with Crohn's disease. J Immunol Methods Sep. 30, 2011;372(1-2):177-86. Epub Jul. 27, 2011.
Soukka et al., Supersensitive time-resolved immuno fluorometric assay of free prostate-specific antigen with nanoparticle label technology. Clin Chem. 2001; 47(7):1269-78.
Stamou et al., Self-assembled microarrays of attoliter molecular vessels. Angew Chem Int Ed Engl. Nov. 24, 2003; 42(45):5580-3.
Steemers et al., Multi- analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. Nat Biotechnol. Jan. 2000; 18(1):91-4.
Stitzel et al., Array-to-array transfer of an artificial nose classifier. Anal Chem. Nov. 1, 2001; 73(21):5266-71.
Subbaraman, Detecting single cancer molecules. Technol Rev. Jun. 3, 2010. Last accessed at http://www.technologyreview.com/biomedicine/25462/ on Jan. 31, 2012. 2 pages.
Sykes et al., Quantitation of targets for PCR by use of limiting dilution. Biotechniques. 1992;13(3):444-9.

(56) References Cited

OTHER PUBLICATIONS

Szunerits et al., "Aluminum Surface Corrosion and the Mechanism of Inhibitors Using pH and Metal Ion Selective Imaging Fiber Bundles," Analytical Chemistry, 2002, 74(4), 886-894.
Szunerits et al., "Fabrication of an Optoelectrochemical Microring Array," Analytical Chemistry, 2002, 74(7), 1718-1723.
Szunerits et al., Spatially resolved electrochemiluminescence on an array of electrode tips. Anal Chem. Sep. 1, 2003; 75(17):4382-8.
Szunerits et al., The use of optical fiber bundles combined with electrochemistry for chemical imaging. Chemphyschem. Feb. 17, 2003; 4(2):186-92.
Szurdoki et al., A duplexed microsphere-based fluorescent immunoassay. Anal Biochem. Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. Taianta. Sep. 15, 2005; 67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. Anal. Chem. 1997; 69:4242-4248.
Tanen et al., Development of an Ultrasensitive Digital Immunoassay on the Single Molecule Array (SimoaTM) Platform. 2014 AAPS Annual Meeting. San Diego, CA. Abstract and Poster. Nov. 2-6, 2014. 2 pages.
Taylor et al., Application of high-density optical microwell arrays in a live-cell biosensing system. Anal Biochem. Feb. 15, 2000; 278(2):132-42.
Tessler et al., Protein quantification in complex mixtures by solid phase single-molecule counting. Anal Chem. Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci USA. Nov. 3, 2009;106(44):18437-42. Epub Oct. 19, 2009. 6 pages.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/on Jan. 31, 2012. 4 pages.
Todd et al., Ultrasensitive flow-based immunoassays using single-molecule counting. Clin Chem. Nov. 2007; 53(11):1990-5. Epub Sep. 21, 2007.
Tromberg et al., Development of antibody-based fiber-optic sensors for detection of a benzo[a]pyrene metabolite. Anal Chem. Sep. 15, 1988; 60(18):1901-8.
Ueberfeld et al., Reversible ratiometric probe for quantitative DNA measurements. Anal Chem. Feb. 15, 2004; 76(4):947-52.
Vo-Dinh et al., Phase-resolved fiber-optics fluoroimmunosensor. Applied Spectroscopy. 1990; 44(1):128-132.
Vogelstein et al., Digital PCR. Proc Natl Acad Sci U S A. Aug. 3, 1999;96(16):9236-41.
Walt et al., Biosensing with live cells using a high-density optical fiber array. Radiation Research. 2001; 156(4):442.
Walt et al., Microsensor arrays for saliva diagnostics. Ann N Y Acad Sci. Mar. 2007; 1098:389-400.
Walt et al., Optical sensor arrays for odor recognition. Biosens Bioelectron. Sep. 15, 1998; 13(6):697-9.
Walt et al., Ultrasensitive detection of proteins using single molecule arrays (SiMoA). Presented Mar. 1, 2010. Pittcon. Abstract and PowerPoint presentation. 33 pages.
Walt, An array of solutions, fiber arrays contribute to studies of individual cellular behavior and response. SPIE'S oemagazine. 2005; 19-21.
Walt, Fiber optic array biosensors. Biotechniques. Nov. 2006; 41(5):529, 531, 533 passim.
Walt, Fiber optic imaging sensors. Accounts of Chemical Research. 1998; 31:267-278.
Walt, Imaging optical sensor arrays. Curr Opin Chem Biol. Oct. 2002; 6(5):689-95.
Walt, Optical methods for single molecule detection and analysis. Anal Chem. Feb. 5, 2013;85(3):1258-63. doi: 10.1021/ac3027178. Epub Dec. 19, 2012.
Walt, Techview: molecular biology. Bead-based fiber-optic arrays. Science. Jan. 21, 2000; 287(5452):451-2.
Wang et al., Quantification of protein based on single-molecule counting by total internal reflection fluorescence microscopy with adsorption equilibrium. Anal Chim Acta. May 2, 2007; 590(1):104-9. Epub Mar. 15, 2007.
Warren et al., Transcription factor profiling in individual hematopoietic progenitors by digital RT-PCR. Proc Natl Acad Sci USA. Nov. 21, 2006;103(47):17807-12. Epub Nov. 10, 2006.
Whitaker et al., Fiber-based single cell analysis of reporter gene expression in yeast two-hybrid systems. Anal Biochem. Jan. 1, 2007; 360(1):63-74. Epub Oct. 30, 2006.
Whitaker et al., Multianalyte single-cell analysis with multiple cell lines using a fiber-optic array. Anal Chem. Dec. 1, 2007; 79(23):9045-53. Epub Nov. 1, 2007.
White et al., An olfactory neuronal network for vapor recognition in an artificial nose. Biol Cybern. Apr. 1998; 78(4):245-51.
White et al., Rapid analyte recognition in a device based on optical sensors and the olfactory system. Analytical Chemistry. 1996; 68(13):2191-2202.
Wilson et al., Development of AccuPSA™, a novel digital immunoassay for sub-femtomolar measurement of PSA in post radical prostatectomy patients. AACR Molecular diagnostics in Cancer Therapeutic Development Poster. 2011. 1 page.
Wilson et al., Fifth-generation digital immunoassay for prostate-specific antigen by single molecule array technology. Clin Chem. Dec. 2011;57(12):1712-21. Epub Oct. 13, 2011.
Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.
Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.
Wu et al., Development and preliminary clinical validation of a high sensitivity assay for cardiac troponin using a capillary flow (single molecule) fluorescence detector. Clin Chem. Nov. 2006; 52(11):2157-9.
Xie et al., Optical studies of single molecules at room temperature. Annu Rev Phys Chem. 1998;49:441-80.
Xie et al., Single gold nanoparticles counter: an ultrasensitive detection platform for one-step homogeneous immunoassays and DNA hybridization assays. J Am Chem Soc. Sep. 9, 2009;131(35):12763-70.
Xue et al., Differences in the chemical reactivity of individual molecules of an enzyme. Nature. Feb. 23, 1995; 373(6516):681-3.
Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.
Young et al., Integrating high-content screening and ligand-target prediction to identify mechanism of action. Nat Chem Biol. Jan. 2008; 4(1):59-68. Epub Dec. 9, 2007.
Office Action for EP App. No. 17201287.4 dated Jul. 10, 2019 and claims pending.
Giraud et al., Fluorescence lifetime biosensing with DNA microarrays and a CMOS-SPAD imager. Biomed Opt Express. Nov. 4, 2010;1(5):1302-1308. doi: 10.1364/BOE.1.001302.
Philippova et al., Magnetic polymer beads: Recent trends and developments in synthetic design and applications. Eur Polym J. Apr. 2011;47(4):542-59.
U.S. Appl. No. 16/906,257, filed Jun. 19, 2020, Duffy et al.
U.S. Appl. No. 17/396,264, filed Aug. 6, 2021, Fournier et al.
U.S. Appl. No. 17/210,258, filed Mar. 23, 2021, Rissin et al.

(56) References Cited

OTHER PUBLICATIONS

U.S. Appl. No. 16/522,237, filed Jul. 25, 2019, Wilson et al.
U.S. Appl. No. 17/135,848, filed Dec. 28, 2020, Rissin et al.
Extended European Search Report for EP Application No. 21181713.5 dated Dec. 21, 2021.
Kaur et al., LNA-modified oligonucleotides effectively drive intramolecular-stable hairpin to intermolecular-duplex state. Biochem Biophys Res Commun. Jan. 5, 2007;352(1):118-22. doi: 10.1016/j.bbrc.2006.10.155. Epub Nov. 7, 2006. Abstract only.
Konry et al., Microsphere-based rolling circle amplification microarray for the detection of DNA and proteins in a single assay. Anal Chem. Jul. 15, 2009;81(14):5777-82. doi: 10.1021/ac900694y.
Li et al., Typing of multiple single-nucleotide polymorphisms by a microsphere-based rolling circle amplification assay. Anal Chem. Dec. 1, 2007;79(23):9030-8. doi: 10.1021/ac701702t. Epub Nov. 1, 2007.
Mullenix et al., Rolling Circle Amplification Improves Sensitivity in Multiplex Immunoassays on Microspheres. Clin Chem. Oct. 1, 2002;48(10):1855-8. doi: 10.1093/clinchem/48.10.1855.
Yang et al., Synthesis and investigation of deoxyribonucleic acid/locked nucleic acid chimeric molecular beacons. Nucleic Acids Res. 2007;35(12):4030-41. doi: 10.1093/nar/gkm358. Epub Jun. 8, 2007.
Kunikata et al., Three dimensional microelectrode array device integrating multi-channel microfluidics to realize manipulation and characterization of enzyme-immobilized polystyrene beads. Sens Actuators B Chem. Aug. 18, 2009;141(1):256-62. Abstract only.
U.S. Appl. No. 17/589,912, filed Feb. 1, 2022, Wilson et al.
U.S. Appl. No. 17/674,968, filed Feb. 18, 2022, Wilson et al.
U.S. Appl. No. 17/496,926, filed Oct. 8, 2021, Walt et al.
U.S. Appl. No. 16/424,989, filed May 29, 2019, Walt et al.

\* cited by examiner

ULTRA-SENSITIVE DETECTION OF MOLECULES OR PARTICLES USING BEADS OR OTHER CAPTURE OBJECTS

RELATED APPLICATIONS

This application is a continuation of U.S. patent application Ser. No. 15/487,889, filed Apr. 14, 2017, entitled "Ultra-Sensitive Detection of Molecules or Particles Using Beads or Other Capture Objects," by Duffy et al., which is a continuation of U.S. patent application Ser. No. 15/265, 996, filed Sep. 15, 2016, entitled "Ultra-Sensitive Detection of Molecules or Particles Using Beads or Other Capture Objects," by Duffy et al., which is a continuation of U.S. patent application Ser. No. 13/530,979, filed Jun. 22, 2012, now U.S. Pat. No. 9,482,662, entitled "Ultra-Sensitive Detection of Molecules or Particles Using Beads or Other Capture Objects," by Duffy et al., which is a continuation of U.S. patent application Ser. No. 12/731,130, filed Mar. 24, 2010, now U.S. Pat. No. 8,236,574, entitled "Ultra-Sensitive Detection of Molecules or Particles Using Beads or Other Capture Objects," by Duffy et al., which claims the benefit of U.S. Provisional Patent Application Ser. No. 61/309,141, filed Mar. 1, 2010, entitled "Ultra-Sensitive Detection of Molecules or Particles Using Beads or Other Capture Objects," by Duffy et al., each of which is incorporated herein by reference.

STATEMENT REGARDING FEDERALLY-SPONSORED RESEARCH OR DEVELOPMENT

This invention was made with government support under contract R43CA133987 awarded by the National Cancer Institute. The government has certain rights in the invention.

FIELD OF THE INVENTION

Described are systems and methods for detecting analyte molecules or particles in a fluid sample and in some cases, determining a measure of the concentration of the molecules or particles in the fluid sample.

BACKGROUND OF THE INVENTION

Methods and systems that are able to quickly and accurately detect and, in certain cases, quantify a target analyte molecule in a sample are the cornerstones of modern analytical measurements. Such systems and/or methods are employed in many areas such as academic and industrial research, environmental assessment, food safety, medical diagnosis, and detection of chemical, biological, and/or radiological warfare agents. Advantageous features of such techniques may include specificity, speed, and sensitivity.

Most current techniques for quantifying low levels of analyte molecules in a sample use amplification procedures to increase the number of reporter molecules in order to be able to provide a measurable signal. For example, these known processes include enzyme-linked immunosorbent assays (ELISA) for amplifying the signal in antibody-based assays, as well as the polymerase chain reaction (PCR) for amplifying target DNA strands in DNA-based assays. A more sensitive but indirect protein target amplification technique, called immunoPCR (see Sano, T.; Smith, C. L.; Cantor, C. R. *Science* 1992, 258, 120-122), makes use of oligonucleotide markers, which can subsequently be amplified using PCR and detected using a DNA hybridization assay (see Nam, J. M.; Thaxton, C. S.; Mirkin, C. A. *Science* 2003; 301, 1884-1886; Niemeyer, C. M.; Adler, M.; Pignataro, B.; Lenhert, S.; Gao, S.; Chi, L. F.; Fuchs, H.; Blohm, D. *Nucleic Acids Research* 1999, 27, 4553-4561; and Zhou, H.; Fisher, R. J.; Papas, T. S. *Nucleic Acids Research* 1993, 21, 6038-6039). While the immuno-PCR method permits ultra low-level protein detection, it is a complex assay procedure, and can be prone to false-positive signal generation (see Niemeyer, C. M.; Adler, M.; Wacker, R. *Trends in Biotechnology* 2005, 23, 208-216).

One feature of typical known methods and/or systems for detecting or quantifying low concentrations of a particular analyte in solution is that they are based on ensemble responses in which many analyte molecules give rise to a measured signal. Most detection schemes require that a large number of molecules are present in the ensemble for the aggregate signal to be above the detection threshold. This requirement limits the sensitivity of most detection techniques and the dynamic range (i.e., the range of concentrations that can be detected). Many of the known methods and techniques are further plagued with problems of non-specific binding, which is the binding of analyte molecules or particles to be detected or reporter species non-specifically to sites other than those expected. This leads to an increase in the background signal, and therefore limits the lowest concentration that may be accurately or reproducibly detected.

Accordingly, improved methods for detecting and, optionally, quantifying analyte molecules or particles in a fluid sample are needed, especially in samples where such molecules or particles are present at very low concentration.

SUMMARY OF THE INVENTION

Described herein are systems and methods for detecting analyte molecules or particles in a fluid sample and in some cases, determining a measure of the concentration of the molecules or particles in the fluid sample. The subject matter of the present invention involves, in some cases, interrelated products, alternative solutions to a particular problem, and/or a plurality of different uses of one or more systems and/or articles.

In some embodiments, a method for determining a measure of the concentration of analyte molecules or particles in a fluid sample comprises exposing a plurality of capture objects that each include a binding surface having affinity for at least one type of analyte molecule or particle, to a solution containing or suspected of containing the at least one type of analyte molecules or particles, immobilizing analyte molecules or particles with respect to the plurality of capture objects such that at least some of the capture objects associate with a single analyte molecule or particle and a statistically significant fraction of the capture objects do not associate with any analyte molecule or particle, spatially segregating at least a portion of the capture objects subjected to the immobilizing step into a plurality of separate locations, addressing at least a portion of the plurality of locations subjected to the spatially segregating step and determining the number of said locations containing an analyte molecule or particle, and determining a measure of the concentration of analyte molecules or particles in the fluid sample based at least in part on the number of locations determined to contain an analyte molecule or particle.

In some embodiments, a method for determining a measure of the concentration of analyte molecules or particles in a fluid sample comprises exposing a plurality of capture objects that each include a binding surface having affinity for at least one type of analyte molecule or particle, to a solution containing or suspected of containing the at least one type of analyte molecules or particles to form capture objects comprising at least one immobilized analyte molecule or particle, mixing the capture objects prepared in the exposing step to a plurality of binding ligands such that at least some of the capture objects associate with a single binding ligand and a statistically significant fraction of the capture objects do not associate with any binding ligand, spatially segregating at least a portion of the capture objects subjected to the mixing step into a plurality of locations, addressing at least a portion of the plurality of locations subjected to the spatially segregating step and determining the number of locations containing a binding ligand, and determining a measure of the concentration of analyte molecules or particles in the fluid sample based at least in part on the number of locations determined to contain a binding ligand.

In some embodiments, a method for determining a measure of the concentration of analyte molecules or particles in a fluid sample comprises providing a substrate comprising a plurality of locations, at least a portion of which locations contain a bead, wherein with respect to the total number of beads present on the substrate, the ratio of beads comprising at least one analyte molecule or particle to beads comprising no analyte molecules or particles is between about 8:1 and about 1:10,000,000, addressing at least a portion of the plurality of locations, wherein during the addressing step at least two of the plurality of locations is addressed at least partially concurrently, detecting at each addressed location the presence or absence of a bead and whether, if present, the bead comprises any analyte molecules or particles, and determining a measure of the concentration of analyte molecules or particles in the fluid sample at least in part by determining the number of locations addressed containing a bead comprising at least one analyte molecule or particle.

In some embodiments, a method for determining a measure of the concentration of analyte molecules or particles in a fluid sample comprises providing a substrate comprising a plurality of locations, at least a portion of which contain a bead, wherein with respect to the total number of beads present on the substrate, the ratio of beads comprising at least one analyte molecule or particle associated with a binding ligand to beads comprising no analyte molecules or particles associated with a binding ligand is between about 8:1 and about 1:10,000,000, addressing at least a portion of the plurality of locations, wherein during the addressing step at least two of the plurality of locations is addressed at least partially concurrently, detecting at each addressed location the presence or absence of a bead and whether, if present, the bead comprises any analyte molecules or particles associated with a binding ligand, and determining a measure of the concentration of analyte molecules or particles in the fluid sample at least in part by determining the number of locations addressed containing a bead comprising at least one analyte molecule or particle associated with a binding ligand.

In some embodiments, an article or kit comprises a plurality of beads having an average diameter between about 0.1 micrometer and about 100 micrometers, and a substrate comprising a plurality of reaction vessels, wherein the average depth of the reaction vessels is between about 1.0 times and about 1.5 times the average diameter of the beads and the average diameter of the reactions vessels is between about 1.0 times and about 1.9 times the average diameter of the beads.

In some embodiments, a method for determining a measure of the concentration of analyte molecules or particles in a fluid sample comprises exposing a plurality of capture objects that each include a binding surface having affinity for at least one type of analyte molecule or particle, to a solution containing or suspected of containing the at least one type of analyte molecules or particles, wherein at least some of the capture objects become associated with at least one analyte molecule or particle, mixing the plurality of capture objects prepared in the exposing step to a plurality of binding ligands comprising an enzymatic component such that a statistically significant fraction of the capture objects associated with at least one analyte molecule or particle associate with a single binding ligand, spatially segregating at least a portion of the capture objects subjected to the mixing step into a plurality of separate locations, determining a measure of the concentration of analyte molecules or particles in the fluid sample based at least in part by addressing at least a portion of the plurality of locations subjected to the spatially segregating step to determine the presence of the enzymatic component or a product of a reaction involving the enzymatic component.

In some embodiments, a method for determining a measure of the concentration of analyte molecules or particles in a fluid sample comprises immobilizing a plurality of analyte molecules or particles with respect to a plurality of beads, spatially segregating at least a portion of the plurality of beads into a plurality of separate locations, and addressing at least some of the plurality of locations and determining the number of locations containing a bead, and further determining the number of said locations containing a bead and an analyte molecule or particle, and determining a measure of the concentration of analyte molecules or particles in the fluid sample based at least in part on the ratio of the number of locations containing a bead and an analyte molecule and particle, to the number of locations containing a bead.

In some embodiments, a method for determining a measure of the concentration of analyte molecules or particles in a fluid sample comprises immobilizing a plurality of analyte molecules or particles with respect to a plurality of beads, spatially segregating at least a portion of the plurality of beads into a plurality of separate locations, addressing at least some of the plurality of locations and determining the number of locations containing a bead, further determining the number of said locations containing a bead and an analyte molecule or particle, and determining a measure of the concentration of analyte molecules or particles in the fluid sample based at least in part on the ratio of the number of locations containing a bead and an analyte molecule and particle, to the number of locations containing a bead but not containing any analyte molecules or particles.

In some embodiments, a method for determining a measure of the concentration of analyte molecules or particles in a fluid sample comprises providing a plurality of capture objects that each are associated with either a single analyte molecule or particle or are free of any analyte molecules or particles, individually addressing at least a portion of the capture objects and determining the number of said capture objects associated with an analyte molecule or particle, and determining a measure of the concentration of analyte molecules or particles in the fluid sample based at least in part on the number of capture objects subjected to the addressing step determined to be associated with an analyte molecule or particle.

BRIEF DESCRIPTION OF THE DRAWINGS

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents mentioned in the text are incorporated by reference in their entirety. In case of conflict between the description contained in the present specification and a document incorporated by reference, the present specification, including definitions, will control.

DETAILED DESCRIPTION

Figure 1:
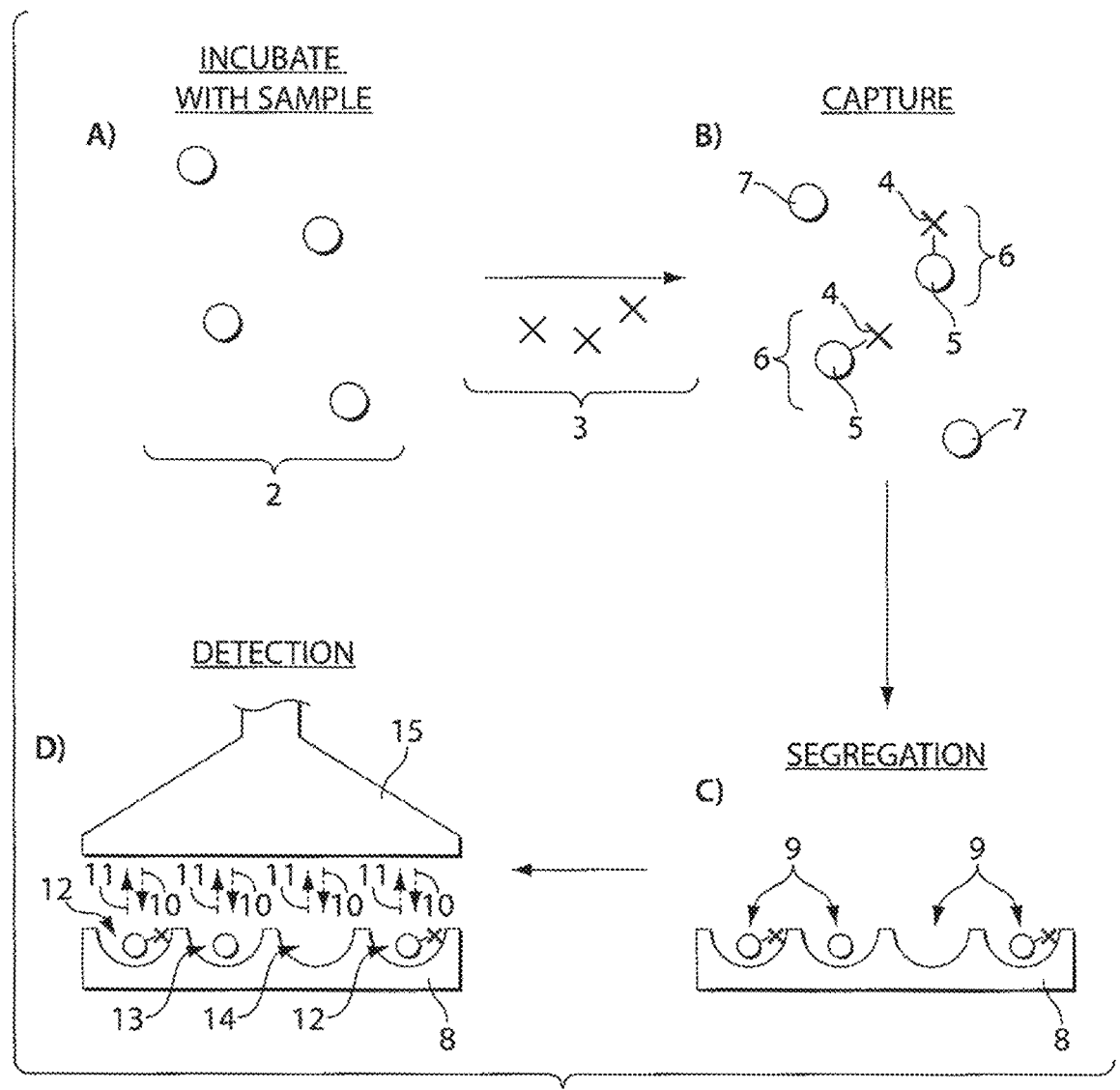
FIG. 1 is a schematic flow diagram depicting one embodiment of steps (A-D) for performing an exemplary method of the present invention.

Described herein are systems and methods that may in certain embodiments be employed for the detection and/or quantification of analyte molecules, particles (such as, for example, cells, cell organelles and other biological or non-biological particulates), and the like, in a sample. The subject matter of the present invention involves, in some cases, interrelated products, alternative solutions to a particular problem, and/or a plurality of different uses of one or more systems and/or articles. It should be understood, that while much of the discussion below is directed to analyte molecules, this is by way of example only, and other materials may be detected and/or quantified, for example, analytes in particulate form. Some exemplary analyte molecules and particles are described herein.

The systems and methods of the present invention in certain instances may help reduce the negative effects of non-specific binding on detection sensitivity when compared to typical conventional systems and methods for performing similar assays. Non-specific binding is the binding or association in a non-specific fashion of one component of an assay with another component of the assay with which it is not desirable that it interact. For example, association, binding, or immobilization of a binding ligand with a substrate or assay material as opposed to with an analyte molecule or particle to which it has binding specificity. Non-specific binding may lead to false positive signals. Non-specific binding may not only affect the accuracy of the assay measurement, but may also limit the lowest level of detection. Therefore, certain methods and/or systems of the present invention that provide improvements in the level of non-specific binding, may allow for the detection and/or quantification of analyte molecules in a sample at a lower detection limit as compared to typical conventional technologies. In addition, certain embodiments of the methods and/or systems of the present invention may also allow for the detection and/or quantification of analyte molecules in certain samples in which such analyte molecules have previously been undetected and/or unquantifiable because of the very low concentration in which they are present.

Certain methods of the present invention may be useful for characterizing analyte molecules in a sample. In some cases, the methods may be useful for detecting and/or quantifying analyte molecules in a fluid sample which is suspected of containing at least one type of analyte molecule, since, as explained in more detail below, the inventive assays may be designed such that the number (or equivalently fraction) of interrogated locations (e.g., wells, reaction sites, areas on a surface, etc.) which contain a capture object (e.g., bead, surface, etc. providing a capture surface) comprising an analyte molecule—or, more generally, the number or fraction of interrogated capture objects of a total interrogated population comprising an analyte molecule—can be correlated to the concentration of analyte molecules in the fluid sample. Certain embodiments of present invention thus can provide a measure of the concentration of analyte molecules in a fluid sample based at least in part on the number or fraction of locations, e.g., on a substrate, which contain a capture object associated with an analyte molecule. In some cases, this number/fraction may be related to the total number of locations comprising a capture object (e.g., with or without an associated analyte molecule or labeling agent) and/or to the total number of locations interrogated. Specific methods and calculations of how to quantify analyte molecules in a fluid sample using embodiments of the invention are discussed more below.

In certain embodiments, a method for detection and/or quantifying analyte molecules (or particles) in a sample comprises immobilizing a plurality of analyte molecules with respect to a plurality of capture objects that each include a binding surface having affinity for at least one type of analyte molecule (or particle). For example, the capture objects may comprise a plurality of beads comprising a plurality of capture components (e.g., an antibody having specific affinity for an analyte molecule of interest, etc.). At least some of the capture objects (e.g., at least some associated with at least one analyte molecule) may be spatially separated/segregated into a plurality of locations, and at least some of the locations may be addressed/interrogated. A measure of the concentration of analyte molecules in the fluid sample may be determined based on the information received when addressing the locations. In some cases, a measure of the concentration may be based at least in part on the number of locations determined to contain a capture object that is or was associated with at least one analyte molecule. In other cases and/or under differing conditions, a measure of the concentration may be based at least in part on an intensity level of at least one signal indicative of the presence of a plurality of analyte molecules and/or capture objects associated with an analyte molecule at one or more of the addressed locations.

In some embodiments, the number/fraction of locations containing a capture object but not containing an analyte molecule may also be determined and/or the number/fraction of locations not containing any capture object may also be determined. In such embodiments, a measure of the concentration of analyte molecule in the fluid sample may be based at least in part on the ratio of the number of locations determined to contain a capture object associated with an analyte molecule to the total number of locations determined to contain a capture object not associated with an analyte molecule and/or a measure of the concentration of analyte molecule in the fluid sample may be based at least in part on the ratio of the number of locations determined to contain a capture object associated with an analyte molecule to the number of locations determined to not contain any capture objects. In yet other embodiments, a measure of the concentration of analyte molecules in a fluid sample may be based at least in part on the ratio of the number of locations determined to contain a capture object and an analyte molecule to the total number of locations addressed and/or analyzed.

In certain embodiments, at least some of the plurality of capture objects (e.g., at least some associated with at least one analyte molecule) are spatially separated into a plurality of locations, for example, a plurality of reaction vessels in an array format. The plurality of reaction vessels may be formed in, on and/or of any suitable material, and in some cases, the reaction vessels can be sealed or may be formed upon the mating of a substrate with a sealing component, as discussed in more detail below. In certain embodiments, especially where quantization of the capture objects associated with at least one analyte molecule is desired, the partitioning of the capture objects can be performed such that at least some (e.g., a statistically significant fraction) of the reaction vessels comprise at least one or, in certain cases, only one capture object associated with at least one analyte molecule and at least some (e.g., a statistically significant fraction) of the reaction vessels comprise an capture object not associated with any analyte molecules. The capture objects associated with at least one analyte molecule may be quantified in certain embodiments, thereby allowing for the detection and/or quantification of analyte molecules in the fluid sample by techniques described in more detail herein.

An exemplary embodiment of an inventive assay method is illustrated in FIG. 1. A plurality of capture objects 2, are provided (step (A)). In this particular example, the plurality of capture objects comprises a plurality of beads. The beads are exposed to a fluid sample containing a plurality of analyte molecules 3 (e.g., beads 2 are incubated with analyte molecules 3). At least some of the analyte molecules are immobilized with respect to a bead. In this example, the analyte molecules are provided in a manner (e.g., at a concentration) such that a statistically significant fraction of the beads associate with a single analyte molecule and a statistically significant fraction of the beads do not associate with any analyte molecules. For example, as shown in step (B), analyte molecule 4 is immobilized with respect to bead 5, thereby forming complex 6, whereas some beads 7 are not associated with any analyte molecules. It should be understood, in some embodiments, more than one analyte molecule may associate with at least some of the beads, as described herein. At least some of the plurality of beads (e.g., those associated with a single analyte molecule or not associated with any analyte molecules) may then be spatially separated/segregated into a plurality of locations. As shown in step (C), the plurality of locations is illustrated as substrate 8 comprising a plurality of wells/reaction vessels 9. In this example, each reaction vessel comprises either zero or one beads. At least some of the reaction vessels may then be addressed (e.g., optically or via other detection means) to determine the number of locations containing an analyte molecule. For example, as shown in step (D), the plurality of reaction vessels are interrogated optically using light source 15, wherein each reaction vessel is exposed to electromagnetic radiation (represented by arrows 10) from light source 15. The light emitted (represented by arrows 11) from each reaction vessel is determined (and/or recorded) by detector 15 (in this example, housed in the same system as light source 15). The number of reaction vessels containing an analyte molecule (e.g., reaction vessels 12) is determined based on the light detected from the reaction vessels. In some cases, the number of reaction vessels containing a bead not associated with an analyte molecule (e.g., reaction vessel 13), the number of wells not containing a bead (e.g., reaction vessel 14) and/or the total number of wells addressed may also be determined. Such determination(s) may then be used to determine a measure of the concentration of analyte molecules in the fluid sample.

A statistically significant fraction of capture objects that contain at least one analyte molecule (or no analyte molecules) will typically be able to be reproducibly detected and quantified using a particular system of detection and will typically be above the background noise (e.g., non-specific binding) that is determined when carrying out the assay with a sample that does not contain any analyte molecules, divided by the total number of objects (or locations) addressed. A "statistically significant fraction" as used herein for the present embodiments, may be estimated according to the Equation 1:

$$n \leq 3\sqrt{n} \qquad \text{(Eq. 1)}$$

wherein n is the number of determined events for a selected category of events. That is, a statistically significant fraction occurs when the number of events is greater than three times square root of the number of events. For example, to determine a statistically significant fraction of the capture objects not associated with any analyte molecules or particles, n is the number of capture objects detected that are not associated with any analyte molecules or particles. As another example, to determine a statistically significant fraction of the capture objects associated with at least one analyte molecule, n is the number of capture objects detected that are determined to be associated with an analyte molecule.

In some embodiments, the statistically significant fraction of capture objects (e.g., beads) associated with at least one analyte molecule (or a single analyte molecule in some cases where the ratio of mixing capture objects to analyte molecules would lead, statistically, to only zero or one analyte molecule associate with each capture object) to the total number of capture objects (e.g., beads) is less than about 1:2, less than about 1:3, less than about 1:4, is less than about 2:5, less than about 1:5, less than about 1:10, less than about 1:20, less than about 1:100, less than about 1:200, or less than about 1:500. Therefore, in such embodiments, the fraction of capture objects (e.g., beads) not associated with any analyte molecules to the total number of capture objects (e.g., beads) is at least about 1:100, about 1:50, about 1:20, about 1:10, about 1:5, about 1:4, about 1:3, about 1:2, about 1:1, about 2:1, about 3:1, about 4:1, about 5:1, about 10:1, about 20:1, about 50:1, about 100:1, or the like.

In some embodiments, the percentage of capture objects (e.g., beads) associated with at least one analyte molecule (or a single analyte molecule in some cases where the ratio of mixing capture objects to analyte molecules would lead, statistically, to only zero or one analyte molecule associate with each capture objects) is less than about 50%, less than about 40%, less than about 30%, less than about 20%, less than about 10%, less than about 5%, less than about 2%, less than about 1%, less than about 0.5%, less than about 0.01%, or the like, the total number of capture objects. In some embodiments, the percentage of capture objects (e.g., beads) not associated with an analyte molecule to the total number of capture objects (e.g., beads) is at least about 30%, at least about 40%, at least about 50%, at least about 60%, at least about 70%, at least about 80%, at least about 90%, at least about 95%, at least about 98%, or the like, the total number of capture objects.

In some embodiments, prior to spatially separating the plurality of capture objects, the capture objects may be exposed to a plurality of binding ligands which have an affinity for at least one type of analyte molecule (or particle). A "binding ligand," as used herein, is any molecule, particle, or the like which specifically binds to or otherwise specifically associates with an analyte molecule to aid in the detection of the analyte molecule. Binding ligands may be particularly useful in embodiments where at least some of the capture objects are associated with respect to more than one analyte molecule (e.g., two, three, four, five, or more, analyte molecules). In some cases, the binding ligand may be provided in a manner (e.g., at a concentration level) such that a statistically significant fraction of the capture objects comprising at least one analyte molecule associate with at least one binding ligand (or in some cases, a single binding ligand) and a statistically significant fraction of the capture objects (e.g., capture objects either associated with at least one analyte molecule or not associated with any analyte molecules) do not associate with any binding ligand.

A statistically significant fraction of the locations that contain a capture object (e.g., bead) associated with at least one analyte molecule and a single binding ligand is greater than or equal to the minimum number of locations that can be reproducibly determined to contain an capture object (e.g., bead) associated with a single binding ligand with a particular system of detection (i.e., substantially similar results are obtained for multiple essentially identical fluid samples comprising the capture objects associated with an analyte molecule and/or binding ligand) and that is above the background noise (e.g., non-specific binding) that is determined when carrying out the assay with a sample that does not contain any analyte molecules and/or binding ligands, divided by the total number of locations. The statistically significant fraction of locations that contain a capture object associated with at least one analyte molecule and a single binding ligand can be determined according to Equation 1. The ratio of the number of capture objects to analyte molecules and/or binding ligands which may be provided such that substantially all of the capture objects are associated with zero or a single analyte molecule may be calculated using a Poisson distribution adjustment, as described herein.

In some embodiments, the statistically significant fraction of capture objects (e.g., beads) associated with at least one analyte molecule and at least one binding ligand to the total number of capture objects (e.g., beads) is less than about 1:2, less than about 1:3, less than about 1:4, is less than about 2:5, less than about 1:5, less than about 1:10, less than about 1:20, less than about 1:100, less than about 1:200, or less than about 1:500. In some cases, the statistically significant fraction of capture objects (e.g., beads) associated not associated with any binding ligand to the total number of capture objects at least about 1:100, about 1:50, about 1:20, about 1:10, about 1:5, about 1:4, about 1:3, about 1:2, about 1:1, about 2:1, about 3:1, about 4:1, about 5:1, about 10:1, about 20:1, about 50:1, about 100:1, or the like.

In some embodiments, the percentage of capture objects (e.g., beads) associated with at least one analyte molecule and at least one binding ligand to the total number of capture objects (e.g., beads) is less than about 50%, less than about 40%, less than about 30%, less than about 20%, less than about 10%, less than about 5%, less than about 2%, less than about 1%, less than about 0.5%, less than about 0.01%, or less. In some embodiments, the percentage of capture objects (e.g., beads) not associated with any binding ligand to the total number of capture objects is at least about 30%, at least about 40%, at least about 50%, at least about 60%, at least about 70%, at least about 80%, at least about 90%, at least about 95%, at least about 98%, or greater.

Figure 2:
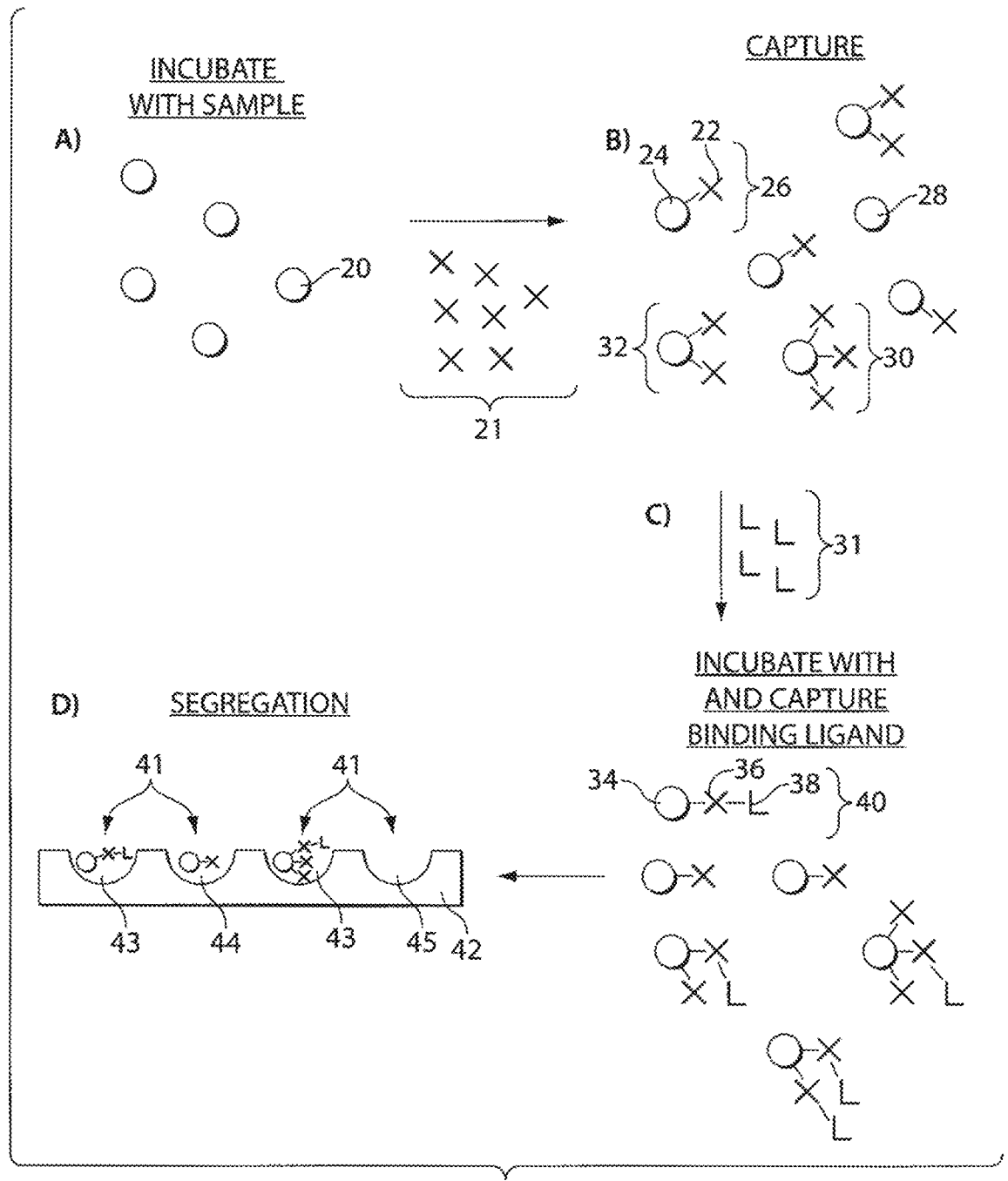
FIG. 2 is a schematic flow diagram depicting one embodiment of steps (A-D) for performing an exemplary method of the present invention.

A non-limiting example of an embodiment where a capture object is associated with more than one analyte molecule is illustrated in FIG. 2. A plurality of capture objects 20 are provided (step (A)). In this example, the plurality of capture objects comprises a plurality of beads. The plurality of beads is exposed to a fluid sample containing plurality of analyte molecules 21 (e.g., beads 20 are incubated with analyte molecules 21). At least some of the analyte molecules are immobilized with respect to a bead. For example, as shown in step (B), analyte molecule 22 is immobilized with respect to bead 24, thereby forming complex 26. Also illustrated is complex 30 comprising a bead immobilized with respect to three analyte molecules and complex 32 comprising a bead immobilized with respect to two analyte molecules. Additionally, in some cases, some of the beads may not associate with any analyte molecules (e.g., bead 28). The plurality of beads from step (B) is exposed to a plurality of binding ligands 31. As shown in step (C), a binding ligand associates with some of the analyte molecules immobilized with respect to a bead. For example, complex 40 comprises bead 34, analyte molecule 36, and binding ligand 38. The binding ligands are provided in a manner such that a statistically significant fraction of the beads comprising at least one analyte molecule become associated with at least one binding ligand (e.g., one, two, three, etc.) and a statistically significant fraction (i.e. as determined by Equation 1 above) of the beads comprising at least one analyte molecule do not become associated with any binding ligands. At least a portion of the plurality of beads from step (C) are then spatially separated into a plurality of locations. As shown in step (D), in this example, the locations comprise a plurality of reaction vessels 41 on a substrate 42. The plurality of reaction vessels may be exposed to the plurality of beads from step (C) such at each reaction vessel contains zero or one beads. The substrate may then be analyzed to determine the number of reaction vessels containing a binding ligand (e.g., reaction vessels 43), wherein in the number may be related to a measure of the concentration of analyte molecules in the fluid sample. In some cases, the number of reaction vessels containing a bead and not containing a binding ligand (e.g., reaction vessel 44), the number of reaction vessels not containing a bead (e.g., reaction vessel 45), and/or the total number of reaction vessels addressed/analyzed may also be determined. Such determination(s) may then be used to determine a measure of the concentration of analyte molecules in the fluid sample.

The foregoing exemplary methods may be performed using a number of different assay formats, different reaction conditions, and/or detection systems in different embodiments of the invention, several examples of which are described below. Additional components and/or method steps may be utilized as a substitute for and/or in combination with the exemplary methods and components described herein within the scope of the invention. It should be understood, while certain of the discussion herein focuses on a plurality of locations comprising a plurality of wells/reaction vessels in a substrate, this is by no means limiting and other materials may be used to segregate capture objects/molecules into a plurality of spatially distinct locations (e.g., regions in/on a hydrogel, points/regions on the surface of a planar substrate, etc.). As another example, while much of the discussion herein focuses on a plurality of capture objects comprising a plurality of beads, this is by no means limiting and in other embodiments the capture objects may take other physical forms (e.g., nanotubes, disks, rings, microfluidic droplets, etc.).

Exemplary Assay Formats

The inventive assays may be carried our according to a very wide variety of basic protocols and formats. The particular format chosen can be based on the nature of the analyte molecules, the nature of the fluid sample containing the analyte molecules, and the availability and properties of binding partners of the analyte as well as other factors. Several exemplary basic formats were discussed previously in the context of the discussion of FIGS. 1-2. As would be apparent to those skilled in the art with the benefit of the teachings provided by the present disclosure, the invention may alternatively be performed according to protocols/formats not specifically described in the specific, exemplary embodiments illustrated in this detailed description, but which do not require undue burden or experimentation to practice.

As described above, an exemplary basic assay format/protocol comprises exposing a plurality of capture objects (e.g., beads) configured to capture an analyte molecule or particle to a sample containing or suspected of containing such analyte molecules (or particles). At least some of the analyte molecules may become immobilized with respect to a capture object. The plurality of capture objects may each include a binding surface having affinity for at least one type of analyte molecule. At least a portion of the capture objects may then be spatially segregated into a plurality of locations (e.g., reaction vessels/wells). Based at least in part on a determination of the number of locations comprising a capture object comprising at least one analyte molecule, a measure of the concentration of analyte molecules may be determined. Various other aspects of this basic assay format will now be discussed, including numerous considerations regarding the materials, concentrations, solutions, steps, and the like.

In certain embodiments, a plurality of capture objects is exposed to a sample containing or suspected of containing at least one type of analyte molecules, wherein the plurality of capture objects comprises a binding surface having an affinity for the at least one type of analyte molecule. In some cases, the binding surface may comprise a plurality of capture components. A "capture component", as used herein, is any molecule, other chemical/biological entity, or solid support modification disposed upon a solid support that can be used to specifically attach, bind or otherwise capture a target molecule or particle (e.g., an analyte molecule), such that the target molecule/particle becomes immobilized with respect to the capture component and the support. The immobilization, as described herein, may be caused by the association of an analyte molecule with a capture component on the surface of the capture object. As used herein, "immobilized" means captured, attached, bound, or affixed so as to prevent dissociation or loss of the target molecule/particle, but does not require absolute immobility with respect to either the capture component or the object.

The number of analyte molecules which are immobilized with respect to a capture object may depend on the ratio of the total number of analyte molecules in the sample versus at least one of the total number, size, and/or surface density of capture components of capture objects provided. In some embodiments, the number of molecules or particles immobilized with respect to a single capture object may follow a standard Poisson distribution. In some cases, a statistically significant number of the capture objects associate with a single analyte molecule and a statistically significant number of capture objects do not associate with any analyte molecules. The total number of capture objects provided may be between about 10,000 and about 10,000,000, between about 50,000 and about 5,000,000, or between about 100,000 and about 1,000,000. In some cases, the total number of capture objects provided is at least about 10,000, at least about 50,000, at least about 100,000, at least about 1,000,000, at least about 5,000,000, or at least about 10,000,000. In some cases, the ratio of the number of analyte molecules in the fluid sample to capture objects provided is between about 10:1 and about 1:10,000,000, between about 8:1 and about 1:10,000,000, between about 10:1 and about 2:1, between about 2:1 and about 1:10, or less than about 1:10 (e.g., about 1:20, about 1:30, etc.). The ratio of analyte molecules in the fluid sample to capture objects provided may affect the assay steps and/or analysis carried out to determine a measure of the concentration of analyte molecules in the fluid sample, as described herein in the Quantification section.

In some cases, substantially all of the analyte molecules provided in the sample may become immobilized with respect to a capture object. That is, greater than about 90%, greater than about 95%, greater than about 97%, greater than about 98%, or greater than about 99% of the analyte molecules in the sample may become immobilized with respect to a capture object. In some cases, however, only a fraction of the analyte molecules in the sample may become immobilized with respect to a capture object. That is, in some cases, between about 1% and about 90%, between about 10% and about 90%, between about 20% and about 80%, or between about 30% and about 70% of the analyte molecules provided in the sample are immobilized with respect to a capture object. In some embodiments, at least about 10%, about 20%, about 30%, about 40%, about 50%, about 60%, about 70%, about 80%, or about 90%, or about 95% of the analyte molecules are immobilized with respect to a capture object.

In some formats of the assay, following immobilization, the plurality of capture objects (e.g., at least some of which are associated with at least one analyte molecule) may be exposed to a plurality of binding ligands. At least some of the analyte molecules immobilized with respect to a capture object may associate with a binding ligand. The number of binding ligands which associate with a capture object (e.g., via an analyte molecule) may depend on the ratio of the total number of analyte molecules immobilized with respect to a single capture object versus the total number of binding ligands exposed to the capture objects. For example, in embodiments where substantially all of the capture objects are associated with either zero or one analyte molecules, conditions may be selected such that substantially all of the analyte molecules associate with a single binding ligand, therefore each capture object associated with a single analyte molecule becomes associated with a single binding ligand (e.g., via the analyte molecule). Thus, the number of locations (e.g., reaction vessels) which contain a single analyte molecule may be determined by determining the number of locations (e.g., reaction vessels) which comprise a binding ligand. In such embodiments (e.g., where zero or at least one analyte molecules are associated with each capture object), the ratio of binding ligands provided (e.g., in a mixing step) to the total number of analyte molecules immobilized with respect to a capture object may be about 20:1, about 10:1, about 5:1, about 2:1, or about 1:1.

In some embodiments, however, a single capture object may be associated with zero, one, or more than one (e.g., two, three, four, etc.) analyte molecules. In such embodiments, the binding ligand may be provided at a concentration such that a statistically significant fraction of the capture objects comprising at least one analyte molecule associate with only a single binding ligand and a statistically significant fraction of the capture objects comprising at least one analyte molecule do not associate with any binding ligand. In other embodiments, however, the binding ligands may be provided at a concentration such that a statistically significant fraction of the capture objects comprising at least one analyte molecule associate with at least one binding ligand (e.g., one, two, three, etc.) and a statistically significant fraction of the capture objects comprising at least one analyte molecule do not associate with any binding ligand. The concentration of analyte molecules in the fluid sample may then be determined, either with an analysis based at least in part of the number of locations containing a capture object associated with a binding ligand (e.g., by relating the concentration of analyte molecules in the fluid sample to the number of locations comprising a binding ligand), and/or an analysis based at least in part on an intensity reading of a signal indicative of the number of binding ligands at the addressed locations (e.g., in embodiments where at least some of the capture objects comprise more than one analyte molecule and/or more than one binding ligand, as described herein). In such embodiments (e.g., wherein more than one analyte molecule may be immobilized with respect to each capture object), the ratio of the number of binding ligands provided in solution to the number of analyte molecules immobilized with respect to a capture object may be about 1:50, about 1:40, about 1:30, about 1:20, about 1:10, about 1:5, about 1:3, about 1:2, about 1:1, or the like. In some cases, the ratio of the number of binding ligands provided in solution may be calculated based on the number of capture objects provided. In some cases, the ratio of binding ligands provided to the number of capture objects is about 1:50, about 1:40, about 1:30, about 1:20, about 1:10, about 1:5, about 1:3, about 1:2, about 1:1, or the like. In other cases, the ratio the number of capture objects to the number of binding ligands provided is about 1:50, about 1:40, about 1:30, about 1:20, about 1:10, about 1:5, about 1:3, about 1:2, or the like. In some embodiments, the quantification determination may comprise a Poisson distribution adjustment, as described herein.

In some embodiments, the concentration of binding ligand used in an assay may be selected as to minimize certain events which may occur when an excess of binding ligand is present, for example, non-specific binding of the binding ligand. In some cases, if the concentration of binding ligand is too high, an increase in background readings may occur due to non-specific interactions (e.g., with the capture objects, reaction vessels, etc.). In some cases, the concentration of binding ligand may be selected (or estimated, in the case of an unknown concentration of analyte molecule) such that a only a fraction of the analyte molecules immobilized with respect to a capture object associate with a binding ligand (e.g., about 0.1%, about 1%, about 2%, about 3%, about 4%, about 5%, about 10%, about 20%, about 30%, about 40%, about 50%, or more). This may be especially useful in embodiments where the percentage of capture objects which associate with at least one analyte molecule is relatively high (e.g., greater than about 20%, greater than about 30%, greater than about 40%, greater than about 50%, greater than about 60%, greater than about 70%, greater than about 80%, greater than about 90%, or more). By providing the binding ligand at a lower concentration, in some cases, not every analyte molecule immobilized with respect to a capture object will associate with a binding ligand, which can be advantageous for quantification, for example when the presence of a binding ligand is required for detection, and especially when using a digital/binary read-out technique. For example, if the percentage of capture objects associated with an analyte molecule is about 50% or greater, a reduced number of binding ligands may be provided such that less than all of the immobilized analyte molecules associate with a binding ligand. In other cases, the percentage of binding ligands that associate with an analyte molecule may be reduced by decreasing the incubation time with the analyte molecule (e.g., limit the time of exposure such that only a fraction of the immobilized analyte molecules associate with an analyte molecule).

The total number of analyte molecules/binding ligands/capture objects/etc. in a solution may be determined using calculations with knowledge of the concentration of the analyte molecules/binding ligands/capture objects/etc. in solution. For example, the total number of binding ligands in a solution may be determined according to Equation 2:

$$\text{\# of binding ligands} = N_A \times [\text{binding ligand}] \times \text{volume} \quad \text{(Eq. 2)}$$

wherein $N_A$ is Avogadro's number ($6.022 \times 10^{23}$ mol$^{-1}$), [binding ligand] is the concentration of the binding ligand in solution in moles per liter, and volume is the total volume of solution in liters employed. Similar calculations may be carried out for other components (e.g., analyte molecules (e.g., in a calibration sample), capture objects, etc.).

Following immobilization of a plurality of analyte molecules with respect to a plurality of capture objects and, in some cases, association of a binding ligand to at least some the immobilized analyte molecules, at least a portion of the capture objects may be spatially segregated into a plurality of locations. The percentage of capture objects which are spatially segregated into the plurality of locations may vary depending on numerous factors including, but not limited to, the ratio of the number of capture objects versus the total number of locations, the method of spatially segregating the capture objects, and/or the length of the time the capture objects are exposed to the locations. In some cases, at least about 0.5%, at least about 1%, at least about 2%, at least about 5%, at least about 10%, at least about 20%, at least about 30%, at least about 40%, at least about 50%, at least about 60%, at least about 70%, at least about 80%, at least above 90%, or more, of the capture objects are spatially segregated into the plurality of locations. In some cases, between about 0.1% and about 50%, between about 0.1% and about 30%, between about 0.5% and about 20%, between about 0.5% and about 10%, between about 0.5% and about 5%, between about 1% and about 10%, or about 0.5%, about 1%, about 2%, about 4%, about 5%, about 10%, about 20%, about 30%, about 50%, about 70%, or about 90% of the capture objects are spatially segregated into the plurality of locations. Following spatially segregating at least a portion of the capture objects into a plurality of locations, at least a portion of the locations may be addressed. The number of locations addressed may be about 0.5%, about 1%, about 2%, about 3%, about 5%, about 10%, about 20%, about 30%, about 40%, about 50%, about 60%, about 70%, about 80%, about 90%, about 95%, or more, of the total number of locations.

The portion of locations may be addressed to determine the number of locations containing an analyte molecule, or in some cases, a binding ligand. In some cases, the number of locations containing a capture object not associated with an analyte molecule (or a binding ligand), the number of locations containing and/or not containing a capture object, and/or the total number of locations analyzed/determined may also be determined. A measure of the concentration of analyte molecules in the fluid sample may be determined at least in part on the number of locations determined to contain an analyte molecule (or binding ligand). In some cases the measure of the concentration of analyte molecules in the fluid sample may be based at least in part on the ratio of the number of locations containing a capture object associated with an analyte molecule to the total number of locations addressed or the total number of locations addressed that contain a capture object. In other cases, a measure of the concentration of analyte molecules in the fluid sample may be based at least in part on the ratio of the number of locations containing a capture object associated with an analyte molecule to the number of locations containing a capture object not associated with an analyte molecule. Specific methods and calculations which may be used to determine the measure of the concentration of analyte molecules in the fluid sample are discussed in more detail below.

The ratios, percentages, and other parameters described herein with respect to the amount/quantity/ratio of a first component to a second component (for example, analyte molecules/capture objects, binding ligands/capture objects, binding ligands/analyte molecules, capture objects/locations, precursor labeling agents/binding ligands, etc.) may be adjusted as desired to yield a desired ratio of analyte molecules/binding ligands captured per capture object, and/or may be controlled or determined using no more than routine experimentation, calculations (in some cases, including accounting for Poisson distributions), screening tests, etc., given the teaching and guidance provided by the present specification. For example, if the number of capture objects provided is known (e.g., as determined using a similar formula as given in Equation 1), the number of binding ligands that need to be provided may be determined based on the desired ratio of capture objects to binding ligands, and hence, the amount of moles of binding ligand that should be provided may be determined. As another example, in the case of an unknown concentration of analyte molecules, if a first assay method indicates that a significant number of capture objects comprise more than one analyte molecule (e.g., all or a significant number of locations are determined to contain an analyte molecule or there is less than a statistically significant number of beads determined to be free of analyte molecules), the fluid sample may be diluted and/or the number of capture objects may be increased such that the number of capture objects comprising at least one analyte molecule may be decreased.

Other aspects of the assay will now be discussed in detail. It should be understood, that none, a portion of, or all of the following steps may be performed at least once during the certain exemplary assay formats described herein. Non-limiting examples of additional steps not described which may be performed include, but are not limited to, washing and/or exposure to additional binding ligands, precursor labeling agents, and/or labeling agents, etc.

In some embodiments, the plurality of capture objects (e.g., at least some of which are associated with at least one analyte molecule) may be exposed to at least one additional reaction component prior to, concurrent with, and/or following spatially separating at least some of the plurality of capture objects into a plurality of locations. In some cases, the capture objects may be exposed to a plurality of binding ligands. In certain embodiments, a binding ligand may be adapted to be directly detected (e.g., the binding ligand comprises a detectable molecule or moiety) or may be adapted to be indirectly detected (e.g., including a component that can convert a precursor labeling agent into a labeling agent), as discussed more below. More than one type of binding may be employed in any given assay method, for example, a first type of binding ligand and a second type of binding ligand. In one example, the first type of binding ligand is able to associate with a first type of analyte molecule and the second type of binding ligand is able to associate with the first binding ligand. In another example, both a first type of binding ligand and a second type of binding ligand may associate with the same or different epitopes of a single analyte molecule, as described below.

Certain binding ligands can comprise a component that is able to facilitate detection, either directly or indirectly. A component may be adapted to be directly detected in embodiments where the component comprises a measurable property (e.g., a fluorescence emission, a color, etc.). A component may facilitate indirect detection, for example, by converting a precursor labeling agent into a labeling agent (e.g., an agent that is detected in an assay). A "precursor labeling agent" is any molecule, particle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique.

In some embodiments, at least one binding ligand comprises an enzymatic component. In some embodiments, the analyte molecule may comprise an enzymatic component. The enzymatic component may convert a precursor labeling agent (e.g., an enzymatic substrate) into a labeling agent (e.g., a detectable product). A measure of the concentration of analyte molecules in the fluid sample can then be determined based at least in part by determining the number of locations containing a labeling agent (e.g., by relating the number of locations containing a labeling agent to the number of locations containing an analyte molecule). Non-limiting examples of enzymes or enzymatic components include horseradish peroxidase, beta-galactosidase, and alkaline phosphatase. Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Isothermal Amplification (LAMP), etc. Such systems and methods will be known to those of ordinary skill in the art, for example, as described in "DNA Amplification: Current Technologies and Applications," Vadim Demidov et al., 2004.

Figure 3:
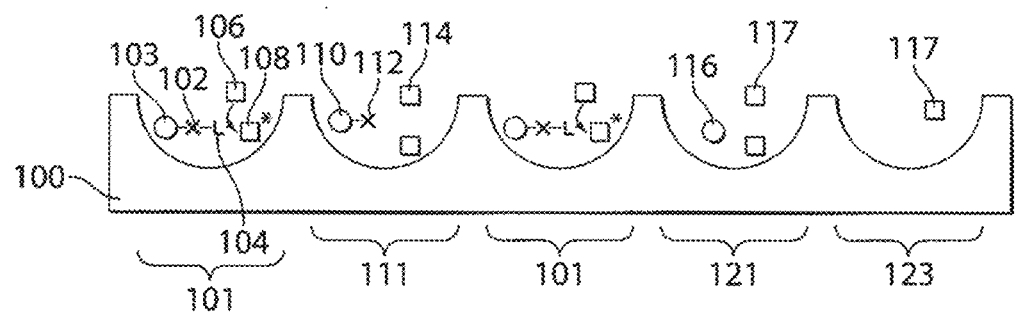
FIG. 3 is a schematic diagram depicting one embodiment of a portion of a method of the present invention.

As an example of an assay method which comprises the use of a precursor labeling agent, as shown in FIG. 3, substrate 100 comprising a plurality of locations is provided, wherein the locations comprise reaction vessels. In reaction vessel 101 (e.g., location), analyte molecule 102 is immobilized with respect to bead 103 (e.g., capture object). Binding ligand 104 is associated with analyte molecule 102. Binding ligand 104 comprises an enzymatic component (not shown). Precursor labeling agent 106 is converted to labeling agent 108 (upon exposure to the enzymatic component). Labeling agent 108 is detected using methods described herein. In contrast, reaction vessel 111 contains analyte molecule 112 immobilized with respect to bead 110. In this reaction vessel, analyte molecule 112 is not associated with a binding ligand comprising an enzymatic component. Therefore, precursor labeling agent 114 is not converted to a labeling agent in the reaction vessel. Thus this reaction vessel would give a different signal as compared to reaction vessel 101 where the precursor labeling agent was converted to a labeling agent. In some cases, there may also be reaction vessels which contain a bead not associated with an analyte molecule, for example, reaction vessel 121 contains bead 116. Additionally, some of the reaction vessels may not comprise any bead, for example, reaction vessel 123. Reaction vessels 121 and 123 may give different signals as compared to reaction vessel 101 as there would be no labeling agent present. However, reaction vessels 121 and 123 may contain precursor labeling agent 117. More than one precursor labeling agent may be present in any given reaction vessel.

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use is described in commonly owned U.S. patent application Ser. No. 12/236,484, entitled "High Sensitivity Determination of the Concentration of Analyte molecules in a Fluid Sample," by Duffy, et al., filed Sep. 23, 2008, incorporated herein by reference.

In some embodiments, during the assay, at least one washing step may be carried out. In one instance, a plurality of capture objects may be washed after exposing the capture objects to one or more solutions comprising analyte molecules, binding ligands, precursor labeling agents, or the like. For example, following immobilization of the analyte molecules with respect to a plurality of capture objects, the plurality of capture objects may be subjected to a washing step thereby removing any analyte molecules not specifically immobilized with respect to a capture object. In certain embodiments, the wash solution is selected so that it does not cause appreciable change to the configuration of the capture objects and/or analyte molecules and/or does not disrupt any specific binding interaction between at least two components of the assay (e.g., a capture component and an analyte molecule). In other cases, the wash solution may be a solution that is selected to chemically interact with one or more assay components. As will be understood by those of ordinary skill in the art, a wash step may be performed at any appropriate time point during the inventive methods.

In some embodiments, assay methods may be carried out that do not comprise the use of a plurality of capture objects comprising a binding surface for at least one type of analyte molecule and/or a plurality of locations to which the capture objects may be spatially separated. For example, an assay according to the invention in certain embodiments may use any suitable method which is capable of isolating single analyte molecules and/or capture objects associated with one or more analyte molecules such that they can be individually addressed for detection. For example, an assay method may comprise providing a plurality of capture objects which are each associated with either a single analyte molecule or are free of any analyte molecules. At least a portion of the capture objects may be individually addressed to determine the number of the capture objects associated with an analyte molecule or particle. Based at least in part on the number of capture objects determined to be associated with an analyte molecule, a measure of the concentration of analyte molecules or particles in a fluid sample may be determined.

Figure 4A:
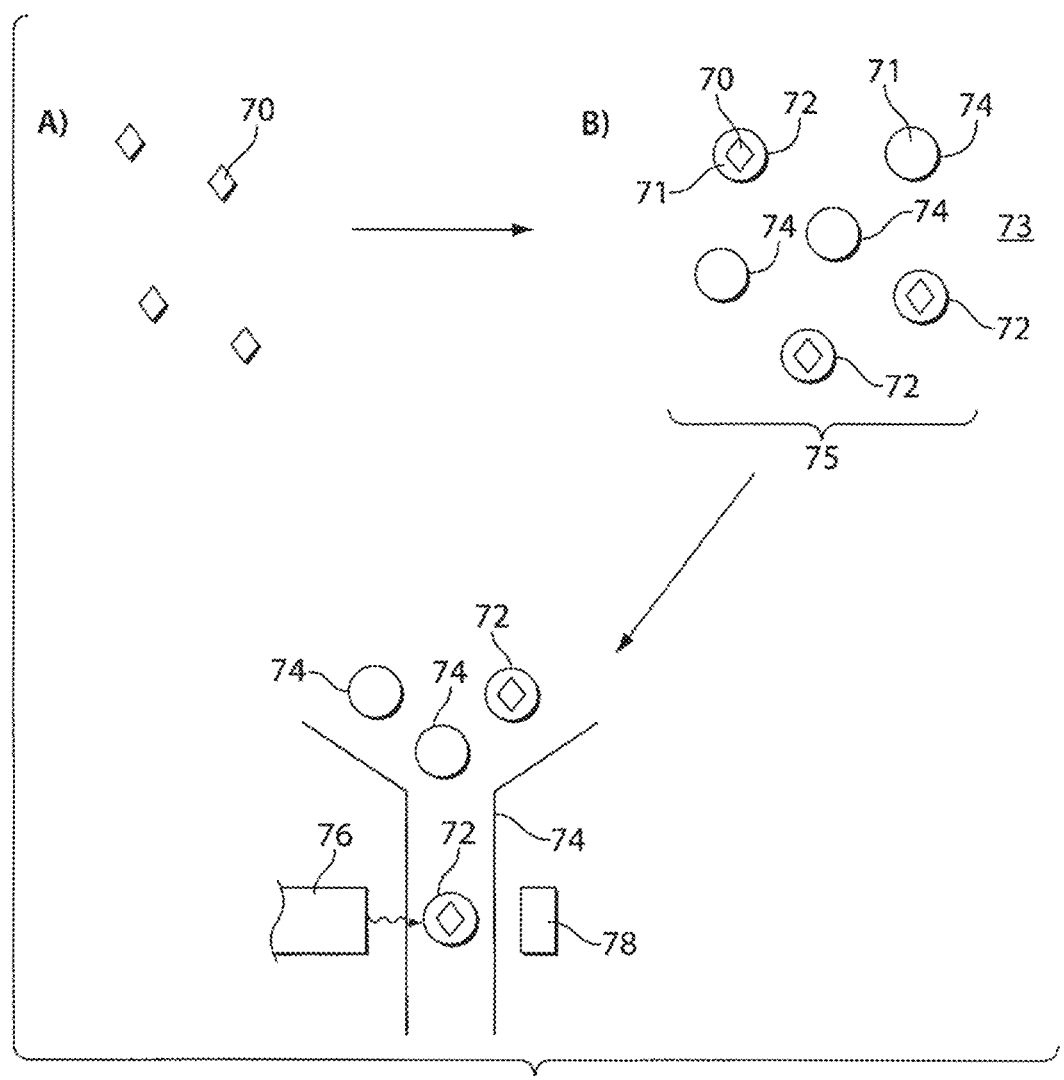
FIG. 4A is a schematic flow diagram depicting one embodiment of steps (A-C) for performing an exemplary method of the present invention.

FIG. 4A illustrates a non-limiting embodiment where single analyte molecules are spatially segregating into a plurality of droplets. In FIG. 4A, plurality of analyte molecules 70 are provided, as shown in step (A). In this example, analyte molecules 70 are capable of being optically detected (e.g., the analyte molecules may be directly detected using optical interrogation). At least some of the plurality of analyte molecules 70 are contained within liquid droplets 72 (e.g., using microfluidic techniques) which comprise fluid 71, as shown in step (B). Additionally, some droplets may be present which do not contain any analyte molecules (e.g., droplets 74 comprising fluid 71). Plurality of droplets 75 are substantially surrounded by fluid 73 which is substantially immiscible with fluid 71. Plurality of droplets 75 can be optically interrogated by feeding droplets into column 74 such that each droplet passes by an optical detection system (e.g., comprising light source 76 and detector 78) single file, as shown in step (C). Each droplet may be determined to contain an analyte molecule when there is a change in the optical single (e.g., a change in optical signal due to the presence of an analyte molecule in the droplet).

Figure 4B:
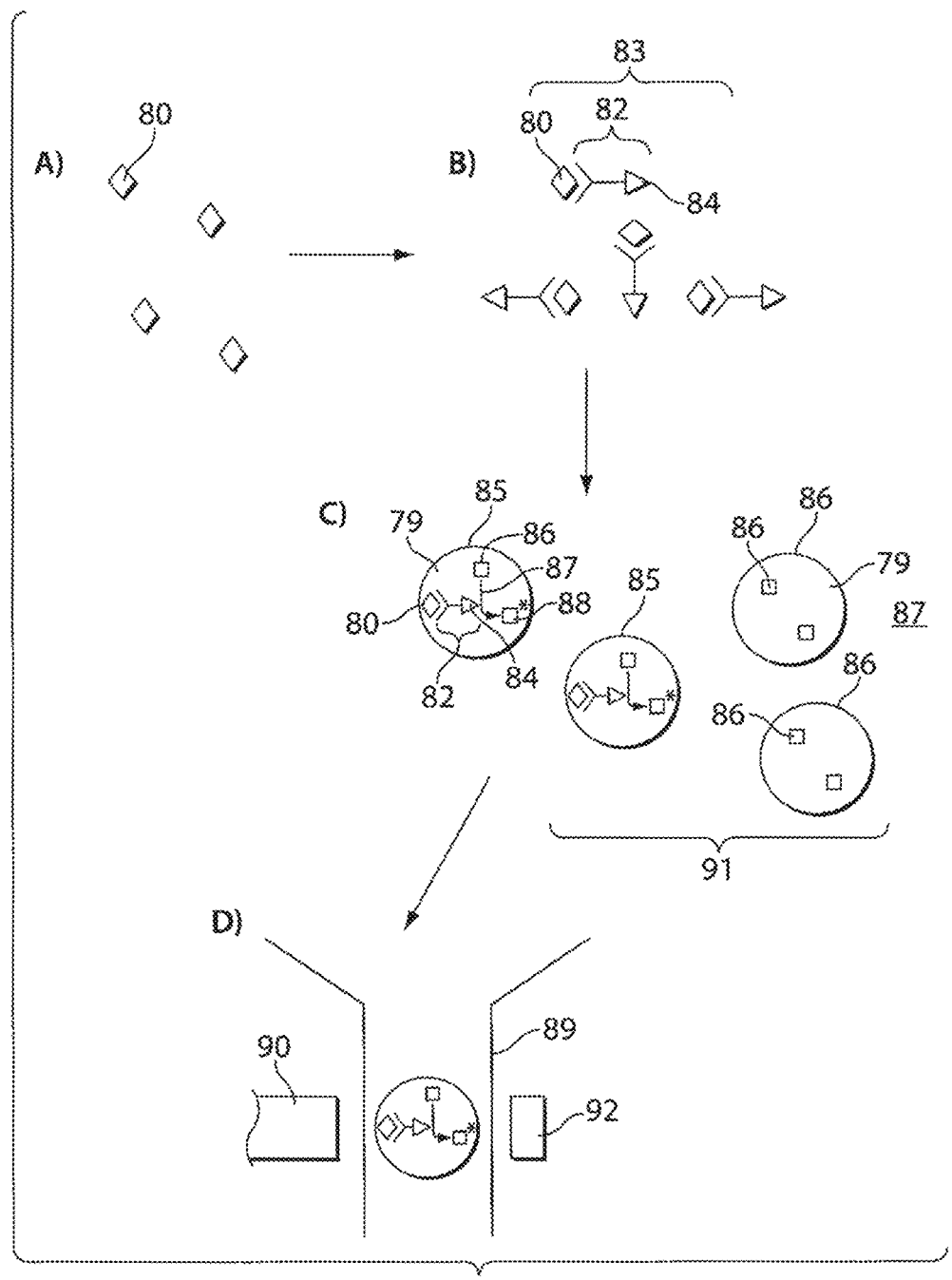
FIG. 4B is a schematic flow diagram depicting one embodiment of steps (A-D) for performing an exemplary method of the present invention.

As another example, as illustrated in FIG. 4B, plurality of analyte molecules 80 are provided, as shown in step (A). In this example, analyte molecules 70 are not capable of being optically detected, and must be indirectly detection (as described herein). Plurality of analyte molecules 80 are exposed to a plurality of binding ligands 82, such that at least one binding ligand associates with a significant portion of the analyte molecules, as shown in step (B), to form complex 83, as shown in step (B). In this example, each binding ligand 82 comprises enzymatic component 84. At least a portion of complexes 83 may be contained in droplets 85 (e.g., using microfluidic techniques), as shown in step (C), which comprise liquid 79. Additionally, some droplets may be present which do not contain any complexes (e.g., droplets 86 comprising fluid 79). Plurality of droplets 91 are substantially surrounded by fluid 87 which is substantially immiscible with fluid 79. Droplets 85 and 86 may additionally comprise precursor labeling agent 86, which is converted to labeling agent 88 upon exposure to enzymatic component 84, as indicated by arrow 87. Plurality of droplets 91 can be optically interrogated by feeding the plurality of droplets into column 89 such that each droplet passes by an optical detection system (e.g., comprising light source 90 and detector 92) single file, as shown in step (D). Each droplet may be determined to contain an analyte molecule when there is a change in the optical single (e.g., a change in optical signal due to the presence of a labeling agent in the droplet).

Figure 4C:
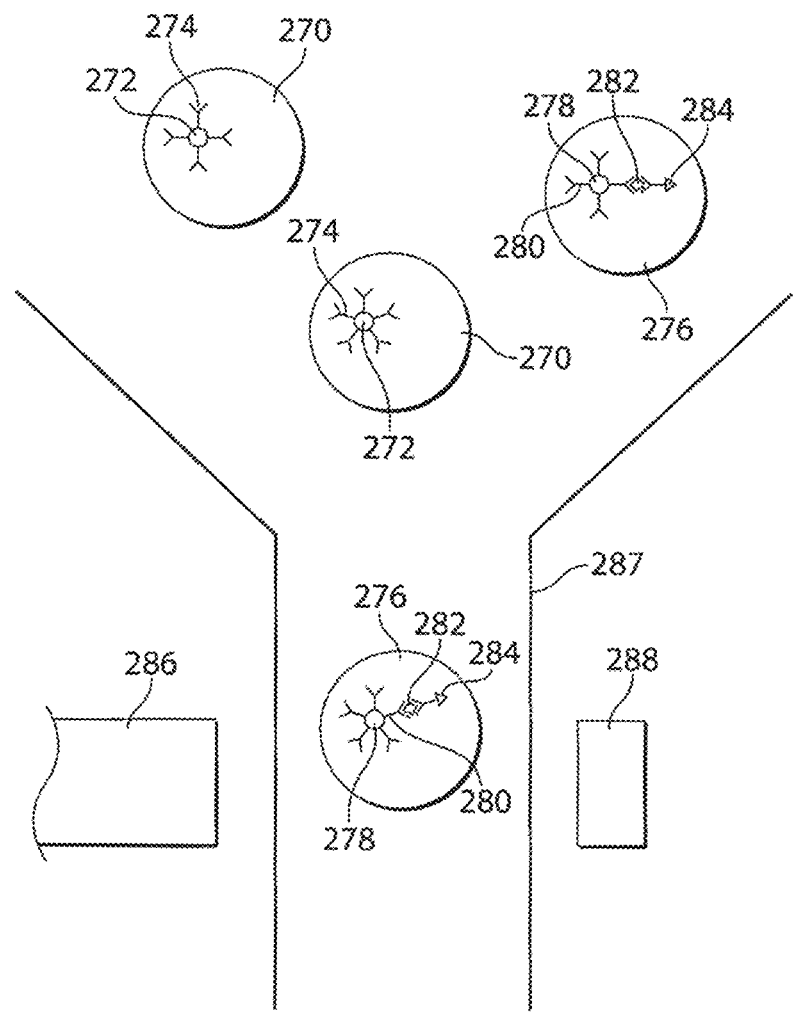
FIG. 4C is a schematic diagram depicting one embodiment for performing an exemplary method of the present invention.

As yet another example, FIG. 4C illustrates an embodiment where single analyte molecules 282 are associated with respect to capture objects 272, 278 via capture components 274. Additionally, in this example, the immobilized analyte molecules are associated with binding ligand 284. The droplets can be optically interrogated by feeding droplets into column 287 such that each droplet passed by the optical detection system (e.g., comprising light source 286 and detector 288) single file. Each droplet may be determined to contain a binding ligand when there is a change in the optical single (e.g., a change in optical signal due to the presence of a binding ligand in the droplet).

The following sections provide additional information regarding method steps, materials, and parameters that may be used to practice the assay methods described above.

Capture Objects and Spatial Locations for Capture Object Segregation

In some embodiments, the method and systems of the present invention utilize a plurality of capture objects that each includes a binding surface having affinity for at least one type of analyte molecule. The plurality of capture objects may be configured to be able to be spatially segregated from each other, that is, the capture objects may be provided in a form such that the capture objects are capable of being spatially separated into a plurality of locations. For example, the plurality of capture objects may comprise a plurality of beads (which can be of any shape, e.g., sphere-like, disks, rings, cube-like, etc.), a dispersion or suspension of particulates (e.g., a plurality of particles in suspension in a fluid), nanotubes, or the like. In some embodiments, the plurality of capture objects is insoluble or substantially insoluble in the solvent(s) or solution(s) utilized in the assay. In some cases, the capture objects are solid or substantially solid (e.g., is essentially free of pores), however, in some cases, the plurality of capture objects may be porous or substantially porous, hollow, partially hollow, etc. The plurality of capture objects may be non-absorbent, substantially non-absorbent, substantially absorbent, or absorbent. In some cases, the capture objects may comprise a magnetic material, which as described herein, may facilitate certain aspect of the assay (e.g., washing step). In some cases, a capture object surface may also comprise a protective or passivating layer that can reduce or minimize non-specific binding events (e.g., analyte molecules, binding ligands, etc.).

In some embodiments, the capture objects each include a binding surface having affinity for at least one type of analyte molecule of interest. The portion of the capture object which comprises a binding surface may be selected or configured based upon the physical shape/characteristics and properties of the capture objects (e.g., size, shape), and the format of the assay. In some embodiments, substantially all of the outer surfaces of the capture objects form the binding surfaces. A binding surface having an affinity for at least one type of analyte molecule may be formed via the association of a plurality of capture components with a capture object. In some cases, an analyte molecule may associate with a capture component (e.g., become immobilized with respect to) via formation of at least one chemical bond and/or physical adsorption, or combination thereof. Non-limiting examples of types of chemical bonds include ionic bonds, covalent bonds (e.g., carbon-carbon, carbon-oxygen, oxygen-silicon, sulfur-sulfur, phosphorus-nitrogen, carbon-nitrogen, metal-oxygen, or other covalent bonds), hydrogen bonds (e.g., between hydroxyl, amine, carboxyl, thiol, and/or similar functional groups), dative bonds (e.g., complexation or chelation between metal ions and monodentate or multidentate ligands), Van der Waals interactions, or the like. Capture components which are useful or potentially useful for practicing certain aspects and embodiments of the invention are discussed in more detail below. At least some of the analyte molecules, upon exposure to the plurality of capture objects comprising a plurality of capture components, become immobilized with respect to a capture component. In certain embodiments, substantially all of the plurality of analyte molecules in the fluid sample tested may become immobilized with respect to the capture components (and hence, the capture objects).

Without wishing to be bound by any theory, the use in certain embodiments of the invention of a capture step in which a plurality of capture objects having a large surface area for binding are exposed to a fluid sample containing the analyte molecules or particles such that the analyte molecules/particles become immobilized with respect to the capture objects may facilitate an increase in the speed and/or efficiency of the assay for detection and quantification of concentration of the analyte in the sample compared to assays where the analyte molecules themselves are segregated for detection without being exposed to and immobilized with respect to a capture object. This increase in binding speed and efficiency may be further enhanced if the solution in which the plurality of analyte molecules and capture objects are incubated for capture is agitated (e.g., stirred) to increase the collision frequency and mass transfer rate between the plurality of capture objects (e.g., plurality of beads) and the analyte molecules (e.g., as contrasted with a substrate comprising a stationary surface (e.g., a microtiter plate)).

The plurality of capture objects for analyte capture may be of any suitable size or shape. Non-limiting examples of suitable shapes include spheres, cubes, ellipsoids, tubes, sheets, and the like. In certain embodiments, the average diameter (if substantially spherical) or average maximum cross-sectional dimension (for other shapes) of a capture object may be greater than about 0.1 um (micrometer), greater than about 1 um, greater than about 10 um, greater than about 100 um, greater than about 1 mm, or the like. In other embodiments, the average diameter of a capture object or the maximum dimension of a capture object in one dimension may be between about 0.1 um and about 100 um, between about 1 um and about 100 um, between about 10 um and about 100 um, between about 0.1 um and about 1 mm, between about 1 um and about 10 mm, between about 0.1 um and about 10 um, or the like. The "average diameter" or "average maximum cross-sectional dimension" of a plurality of capture objects, as used herein, is the arithmetic average of the diameters/maximum cross-sectional dimensions of the capture objects. Those of ordinary skill in the art will be able to determine the average diameter/maximum cross-sectional dimension of a population of capture objects, for example, using laser light scattering, microscopy, sieve analysis, or other known techniques. For example, in some cases, a Coulter counter may be used to determine the average diameter of a plurality of beads.

The capture objects for analyte capture may be fabricated from one or more suitable materials, for example, plastics or synthetic polymers (e.g., polyethylene, polypropylene, polystyrene, polyamide, polyurethane, phenolic polymers, or nitrocellulose etc.), naturally derived polymers (latex rubber, polysaccharides, polypeptides, etc), composite materials, ceramics, silica or silica-based materials, carbon, metals or metal compounds (e.g., comprising gold, silver, steel, aluminum, copper, etc.), inorganic glasses, silica, and a variety of other suitable materials. Non-limiting examples of potentially suitable configurations include beads (e.g., magnetic beads), nanotubes, plates, disks, dipsticks, or the like.

In some embodiments, more than one type of capture object for analyte capture may be employed. In some cases, each type of capture object may include a surface with differing binding specificity. In these embodiments, more than one type of analyte molecule may be quantified and/or detected in a single, multiplexed assay method. For example, the plurality of capture objects for analyte capture may comprise a plurality of a first type of capture object comprising a binding surface having an affinity for a first type of analyte molecule and a plurality of a second type of capture objects comprising a binding surface having an affinity for a second type of analyte molecule. Upon exposure to a sample containing the first type of analyte molecule and the second type of analyte molecule, the first type of analyte molecule becomes immobilized with respect to the first type of capture object and the second type of analyte molecule becomes immobilized with respect to the second type of capture object. The first type of capture object and the second type of capture object may be encoded to be distinguishable from each other (e.g., to facilitate differentiation upon detection) by including a differing detectable property. For example, each type of capture object may have a differing fluorescence emission, a spectral reflectivity, shape, a spectral absorption, or an FTIR emission or absorption. In a particular embodiment, each type of capture object may comprise one or more dye compounds (e.g., fluorescent dyes) but at varying concentration levels, such that each type of capture object has a distinctive signal (e.g., based on the intensity of the fluorescent emission). Upon spatially segregating the capture objects after the capture step into a plurality of locations for detection, a location comprising a first type of capture object associated with a first type of analyte molecule may be distinguished from a location comprising a second type of capture object associated with a second type of analyte molecule via detection of the differing property. The number of locations comprising each type of capture object and/or the number of capture objects associated with an analyte molecule may be determined, enabling a determination of a measure of the concentration of both the first type of analyte molecule and the second type of analyte molecules in the fluid sample based at least in part on these numbers.

Figure 5:
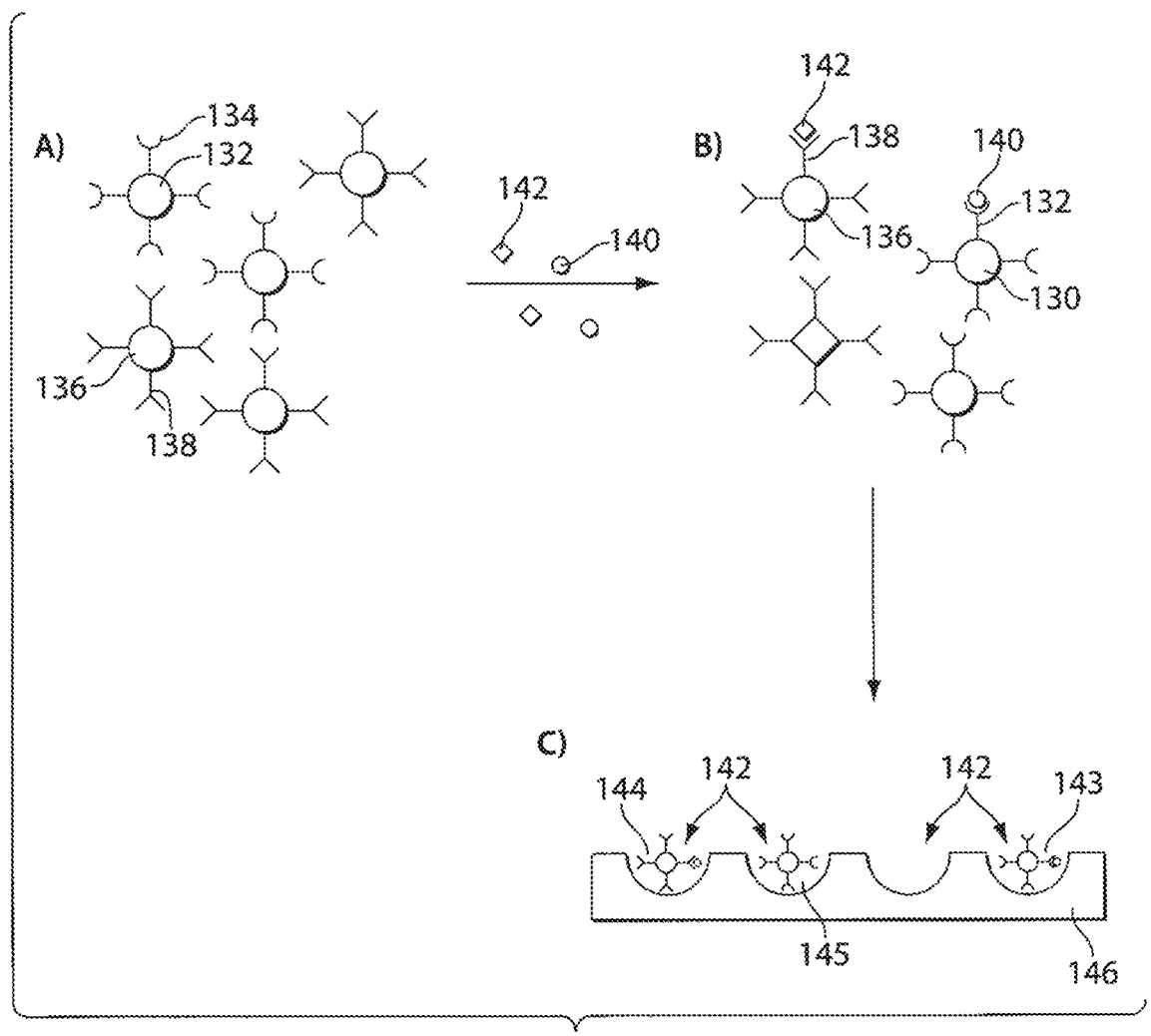
FIG. 5 is a schematic flow diagram depicting one embodiment of steps (A-C) for performing an exemplary method of the present invention.

For example, as illustrated in FIG. 5, step (A) a plurality of a first type of capture object 132 comprising a first type of capture component 134 and a plurality of a second type of capture object 136 comprising a second type of capture component 138 are provided. The plurality of capture objects is exposed to a fluid sample comprising a plurality of a first type of analyte molecule 140 and a second type of analyte molecule 142. As shown in step (B), at least some of the first type of analyte molecule 140 may associate with a capture object of the first type 132 via capture component 134 and at least some of the second type of analyte molecule 142 may associate with a capture object of the second type 136 via capture component 138. Some of the first type of capture objects and second type of capture objects may not associate with any first type of or second type of analyte molecules. At least some of the plurality of capture objects from step (B) may be spatially segregated into a plurality of locations (represented by reaction vessels 142 formed in substrate 146, as shown in step (C). Some of the reaction vessels may not comprise any capture objects. The plurality of reaction vessels may then be analyzed (e.g., for example, as illustrated in FIG. 1, step (D)) to determine the number of reaction vessels containing a first type of capture object associated with a first type of analyte molecule (e.g., reaction vessel 144) and the number of reaction vessels containing a second type of capture object associated with a second type of analyte molecule (e.g., reaction vessel 145). Additionally, the number of locations containing a first type of capture object or a second type of capture object not associated with any analyte molecules may also be determined. A measure of the concentration of the first type (or second type) of analyte molecule may be determined at least in part based on the number of the first type (or second type) of analyte molecule detected. Alternatively, a measure of the concentration of either first type (or second type) of analyte molecule in the fluid sample may be based on the ratio of the number of reaction vessels comprising the first type (or second type) of capture object associated with a first type (or second type) of analyte molecule to the number of reactions vessels comprising the first type (or second type) of capture objects not associated with any analyte molecules. Additional methods for determining the concentration of the first and/or second types of analyte molecules in the fluid sample may be carried out using methods similar to those described herein for samples comprising a single type of analyte molecule. Using optical detection, the first type of capture object may have a maximum wavelength of emission at a first wavelength and the second type of capture object may maximum wavelength of emission at a second wavelength, and therefore, allow for the reaction vessels which contain a first type of capture object to be distinguished from the reaction vessels which contain a second type of capture object.

Alternatively, or in combination, with use of coded capture objects for multiplexing, as described above, in some multiplexed assays, similar capture object types may be employed that may, in certain cases, each include capture components specific for multiple types of analytes. In certain such assays, a first type of binding ligand, e.g., having affinity for a first analyte molecule type, and a second, third, etc. type of binding ligand having affinity for a second, third, etc., respectively type of analyte molecule type and configured to be detectably distinguishable from each other (e.g., through use of differing detectable markers, enzymatic components and/or labeling agents, etc.) may be used in conjunction with the assay, and the detection/quantification of the different types of binding ligands may be correlated to the presence/concentration of different types of analyte molecules in the fluid sample.

In a particular embodiment, the plurality of capture objects for analyte capture comprises a plurality of beads. The beads may each comprise a plurality of capture components via which a plurality of analyte molecules may be immobilized. The plurality of capture components may be present on the surface of the beads. In some embodiments, the beads may be magnetic beads. The magnetic property of the beads may help in separating the beads from a solution (e.g., comprising a plurality of unbound analyte molecules) and/or during washing step(s) (e.g., to remove excess fluid sample, labeling agents, etc.). Potentially suitable beads, including magnetic beads, are available from a number of commercial suppliers. As noted above, there are many other examples of potentially suitable capture objects for analyte capture including nanotubes (e.g., carbon nanotubes), microfluidic droplets (e.g., droplets of a first fluid substantially surrounded by a second fluid), etc.

Those of ordinary skill in the art will be aware of methods and techniques for exposing a plurality of capture objects to a fluid sample containing or suspected of containing an analyte molecule or particle for initial analyte capture. For example, the plurality of capture objects may be added (e.g., as a solid, as a solution) directly to a fluid sample. As another example, the fluid sample may be added to the plurality of capture objects (e.g., in solution, as a solid). In some instances, the solutions may be agitated (e.g., stirred, shaken, etc.).

Following immobilization of the analyte molecules with respect to a plurality of capture objects, the capture objects may be subjected to at least one wash step. The wash step may aid in the removal of any unbound molecules (e.g., analyte molecules, or other reaction components) from the solution. For example, referring to FIG. 1, following immobilization of analyte molecules 4 with beads 6, as shown in step (B), a wash step may be performed to remove any unbound analyte molecules not immobilized with respect to an analyte molecule. As another example, referring to FIG. 2, following association of binding ligands 31 with analyte molecules 36, as shown in step (C), a wash step may be performed to remove any unbound binding ligands. The wash step may be performed using any suitable technique known to those of ordinary skill in the art, for example, by incubation of the capture objects with a wash solution followed by centrifuging the solution comprising the capture objects and decanting off the liquid, or by using filtration techniques. In embodiments where the plurality of capture objects comprises a plurality of magnetic beads, the beads may be isolated from the bulk solution with aid of a magnet.

The plurality of capture objects subsequent to the capture step (e.g., at least some associated with at least one analyte molecule) may be exposed to one or more additional reagents, prior to spatially segregating the plurality of capture objects into a plurality of locations for detection. For example, as noted previously, the capture objects may be exposed a plurality of binding ligands, at least some of which may associate with an immobilized analyte molecule. The capture objects may be exposed to more than one type of binding ligand (e.g., a first type of binding ligand and a second, third, etc. type of a binding ligand), as noted above. The association of a binding ligand with an immobilized analyte molecule may aid in the detection of the analyte molecules, as described herein.

In some embodiments, in addition to a plurality of capture objects for analyte capture, a plurality of control objects may also be provided and/or employed. A control object(s) may be useful for a variety of purposes including, but not limited to, identification of the orientation of the plurality of locations (e.g., in the case where the plurality of locations is formed as an array of reaction sites, reaction vessels, etc.), to help determine the quality of the assay, and/or to help calibrate the detection system (e.g., optical interrogation system), as described below. It should be understood, that more than one type of control object may be present in any assay format (e.g., a first type of control object to determine quality of the assay and a second type of control object to act as a location marker), or a single type of control object may have more than one of the above-described functions.

In some cases, the control objects used to identify the orientation of the plurality of locations (e.g., reaction vessels, sites, etc.) on an array (e.g., function as location marker(s) for an array). For example, a control object may be randomly or specifically distributed on an array, and may provide one or more reference locations for determining the orientation/position of the array. Such a feature may be useful when comparing multiple images of a portion of the array at different time intervals. That is, the positions of control objects in the array may be used to register the images. In some cases, the control objects may be use to provide reference locations in embodiments where a plurality of images of small overlapping regions are being combined to form a larger image.

The presence of control objects in an assay may provide information regarding the quality of the assay. For example, if a location is found to contain a control object comprising an enzymatic component but no labeling agent is present (e.g., the product of which would be present upon exposure of a control object comprising an enzymatic component to a precursor labeling agent), this gives an indication that some aspect of the assay may not be functioning properly. For example, the quality of the reagents may be compromised (e.g., concentration of precursor labeling agent is too low, decomposition of the precursor labeling agent, etc.), and/or perhaps not all of the locations were exposed to the precursor labeling agent.

In some embodiments, the control objects may be used to calibration the detection system. For example, the control objects may output an optical signal which may be used to calibration an optical detection system. In some embodiments, the control objects can be characterized and doped with a particular characteristic (e.g., fluorescence, color, absorbance, etc.) which can act as a quality control check for the detection system performance.

The control object may be provided with the plurality of capture objects for analyte capture prior to exposure to a fluid sample containing analyte molecules, or may be added at another point in the assay (e.g., following exposure to the plurality of analyte molecules and/or binding ligands, and/or prior to spatially segregating the plurality of capture objects into a plurality of locations). The control objects may be distinguishable from the capture objects using techniques known to those of ordinary skill in the art. For example, in some embodiments, the control objects may comprise a unique property (e.g., are encoded) as compare to the capture objects comprising a binding surface for the analyte molecules. For example, the control object may have a different fluorescence emission, a spectral reflectivity, shape, a spectral absorption, or an FTIR emission or absorption, as compared to the capture objects. The percentage of control objects to total number of objects (e.g., capture objects and control objects) in the assay may be about 0.0001%, about 0.0005%, about 0.001%, about 0.005%, about 0.01%, about 0.05%, about 0.1%, about 0.5%, about 1%, about 5%, or the like.

In some embodiments, the control objects are configured as negative binding controls and may be of a similar shape and size as the capture objects used for immobilizing analyte molecules, however, the control objects may lack a binding surface for the analyte molecules (e.g., a plurality of capture components). For example, the control objects may comprise a plurality of beads, and the capture objects for immobilizing the analyte molecules may comprise the same or similar beads, additionally comprising at least one surface comprising a plurality of capture components.

In one embodiment, the control objects may comprise a positive control and include an enzymatic component. A precursor labeling agent may be converted to a labeling agent upon exposure to the enzymatic component. In some cases, the enzymatic component may be the same as the enzymatic component being used to detect the analyte molecules in a fluid sample (e.g., comprised in another component of the assay, for example, an enzymatic component comprised in a binding ligand, an analyte molecule, etc.). In such embodiments, the control object may be distinguishable from the capture objects such that the reaction vessels having a positive signal may be analyzed to determine whether the reaction vessel comprises a control object (e.g., having a first detectable signal) or a capture object (e.g., having a second detectable signal distinguishable from the first detectable signal). In other cases, the enzymatic component may be the different than an enzymatic component being used to detect the analyte molecules in a fluid sample (e.g., comprised in another component of the assay, for example, an enzymatic component comprised in a binding ligand, an analyte molecule, etc.). In this embodiment, the control object may or may not be distinguishable from the capture objects. Both a first type and a second type of precursor labeling agent may be provided to the reaction vessels, and the first type of precursor labeling agent may be converted to a first type of labeling agent upon exposure to the enzymatic component associated with the control beads and the second type of precursor labeling agent may be converted to a second type of labeling agent upon exposure to the other enzymatic component (e.g., comprised in the binding ligand/analyte molecule/etc.). The reaction vessels containing the first type of labeling agent correspond to the reaction vessels containing a control object and reaction vessels containing a second type of labeling agent correspond to the reaction vessels which contain a binding ligand/analyte molecule/etc. The plurality of locations containing a control bead may be observed to analyze, for example, the effectiveness of the enzymatic conversion reaction A variety of methods may be used to prepare the controls objects, for example, similar methods described herein for the capture objects (e.g., beads comprising a plurality of capture components). In some cases, some of the control objects may comprise an enzymatic component. The control objects may be prepared such that 1) the majority of control objects each comprise at least one enzymatic component (e.g., one, two, three, four, etc.) or 2) some of the control objects comprise a single enzymatic component and the remainder of the control objects do not comprise any enzymatic component. In the first case, during formation of the control objects, the ratio of enzymatic components provided in solution to objects may be greater than 1:1, greater than about 2:1, greater than about 5:1, greater than about 10:1, or the like. In such cases, it would be expected that after partitioning the control objects on a substrate, each location comprising a control object would give a positive signal on exposure to a precursor labeling agent. In the second case, during formation of the control objects, the ratio of enzymatic components provided in solution to objects may be less than about 1:5, less than about 1:10, less than about 1:20, less than about 1:50, or the like. In such cases, it would be expected that ratio of the number of locations comprising a control object and giving a positive signal to the number of locations comprising a control object not giving a positive signal would be approximately similar to the ratio of enzymatic components to objects during formation of the control objects and/or may follow a Poisson distribution.

As described above, following immobilization of a plurality of analyte molecules with respect to the plurality of capture objects in the analyte capture step, at least a portion of the capture objects may be spatially segregated into a plurality of locations, for example on a substrate. For example, each of capture objects of the portion of capture objects which are spatially segregated may be positioned in and/or associated with a location (e.g., a spot, region, well, etc. on the surface and/or in the body of a substrate) that spatially distinct from the locations in which each of the other capture objects are located, such that the capture objects and locations can be individually resolved by an analytical detection system employed to address the locations. As an example, each of a portion of the capture objects may be spatially segregated into an array of reaction vessels on a substrate, such that statistically only zero or one capture objects are located in at least some of the reaction vessels and in certain cases in essentially each reaction vessel. Each location may be individually addressable relative to the other locations. Additionally, the locations may be arranged such that a plurality of locations may be addressed substantially simultaneously, as described herein, while still permitting the ability to resolve individual locations and capture objects.

It should be understood, that while much of the discussion herein focusing on locations containing a single capture object, this is by no means limiting, and in some embodiments, more than one capture object may be contained at a single location. In such embodiments, the ratio of capture objects to analyte molecules may be such that following spatial segregation of the plurality of capture objects into the plurality of locations, a statistically significant fraction of the locations contain no analyte molecules and a statistically significant fraction of locations contain at least one analyte molecule. That is, while a single location may contain a plurality of capture objects, in some cases, none of the capture objects are associated with any analyte molecules and only a single one of the capture objects in an addressed location is associated with at least one analyte molecule.

As noted above, in some embodiments, the plurality of locations comprises a plurality of reaction vessels/wells on a substrate. The reactions vessels, in certain embodiments, may be configured to receive and contain only a single capture object used for analyte capture. The plurality of capture objects can be partitioned across a plurality of such reaction vessels (e.g., configured as an array of reaction vessels on a substrate), in some cases, to facilitate determination of a measure of the concentration of analyte molecules in a fluid sample by means discussed in further detail below and in the examples.

In some embodiments of the present invention, the plurality of reaction vessels may be sealed e.g., after the introduction of the capture objects used for analyte capture, for example, through the mating of the second substrate and a sealing component. The sealing of the reaction vessels may be such that the contents of each reaction vessel cannot escape the reaction vessel during the remainder of the assay. In some cases, the reaction vessels may be sealed after the addition of the capture objects and, optionally, a precursor labeling agent to facilitate detection of the analyte molecules. For embodiments employing precursor labeling agents, by sealing the contents in some or each reaction vessel, a reaction to produce the detectable labeling agents can proceed within the sealed reaction vessels, thereby producing a detectable amount of labeling agents that is retained in the reaction vessel for detection purposes.

The plurality of locations comprising a plurality of reaction vessels may be formed using a variety of methods and/or materials. In some cases, the plurality of reaction vessels is formed as an array of depressions on a first surface. In other cases, however, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, e.g., an elastomeric polymer material, to aid in sealing. The surfaces may be or made to be hydrophobic or contain hydrophobic regions to minimize leakage of aqueous samples from the microwells.

In some cases, the sealing component may be capable of contacting the exterior surface of an array of microwells (e.g., the cladding of a fiber optic bundle as described in more detail below) such that each reaction vessel becomes sealed or isolated such that the contents of each reaction vessel cannot escape the reaction vessel. According to one embodiment, the sealing component may be a silicone elastomer gasket that may be placed against an array of microwells with application of substantially uniform pressure across the entire substrate. In some cases, the reaction vessels may be sealed after the addition of the plurality of capture objects used for analyte capture and, optionally, any precursor labeling agent molecule that may be used to facilitate detection of the analyte molecule.

Figure 6:
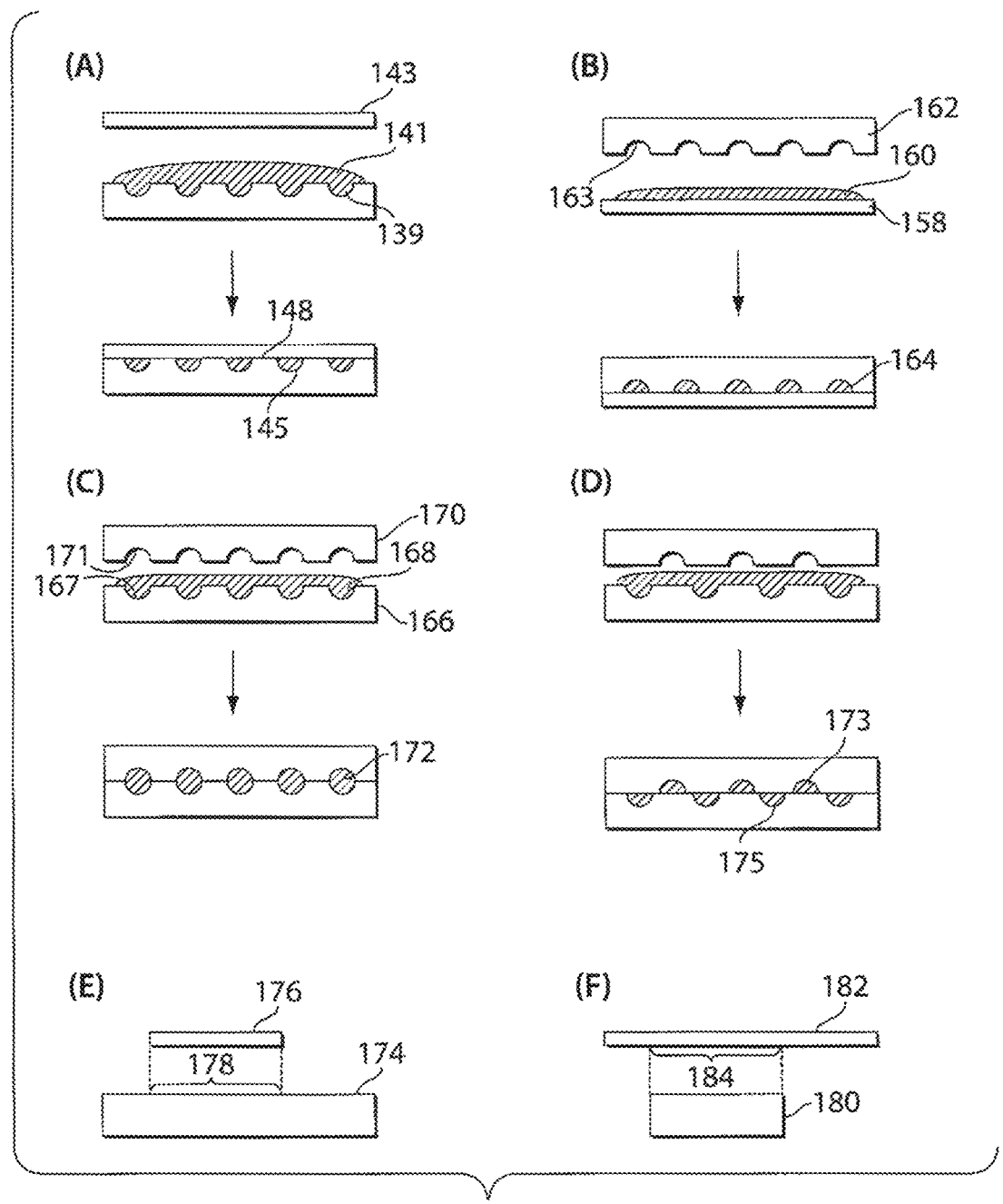
FIG. 6 is a schematic flow diagram depicting an embodiment of a method (steps A-D) for the formation of a plurality of reaction vessels through mating of a substrate and a sealing component and depicting examples of the size (E, F) of a sealing component relative to a substrate.

A non-limiting example of the formation of a plurality of reaction vessels containing assay solution on/in a substrate is depicted in FIG. 6. FIG. 6, panel (A) shows a surface comprising a plurality of microwells 139, which have been exposed to an assay solution 141 (e.g., a solution containing the capture objects used for analyte capture and/or control objects obtained after performance of the analyte capture step(s) and any washing step(s)), and a sealing component 143. Sealing component 143 in this example comprises a substantially planar bottom surface. Mating of substrate 139 with sealing component 143 forms a plurality of sealed reaction vessels 145. The areas between the reaction vessels 148 may be modified to aid in the formation of a tight seal between the reaction vessels.

A second embodiment is shown in FIG. 6, panel (B), in which sealing component 162 comprising a plurality of microwells 163 is mated with a substantially planar surface 158 which has been exposed to assay solution 162, thereby forming a plurality of reaction vessels 164.

In a third embodiment, as shown in FIG. 6, panel (C), substrate surface 166 comprising a plurality of microwells 167 is mated with sealing component 170 also comprising a plurality of microwells 171. In this embodiment, the microwells in the substrate and the microwells in the sealing components are substantially aligned so each reaction vessel 172 formed comprises a portion of the microwell from the sealing component and a portion of a microwell from the substrate. In FIG. 6, panel (D), the microwells are not aligned such that each reaction vessel comprises either a microwell from the sealing component 173 or a microwell from the substrate 175.

The sealing component may be essentially the same size as the substrate or may be different in size. In some cases, the sealing component is approximately the same size as the substrate and mates with substantially the entire surface of the substrate. In other cases, as depicted in FIG. 6, panel (E), the sealing component 176 is smaller than the substrate 174 and the sealing component only mates with a portion 178 of the substrate. In yet another embodiment, as depicted in FIG. 6, panel (F), the sealing component 182 is larger than the substrate 180, and only a portion 184 of the sealing component mates with the substrate 180.

In some embodiments, the reaction vessels may all have approximately the same volume. In other embodiments, the reaction vessels may have differing volumes. The volume of each individual reaction vessel may be selected to be appropriate to facilitate any particular assay protocol. For example, in one set of embodiments where it is desirable to limit the number of capture objects used for analyte capture contained in each vessel to a small number, the volume of the reaction vessels may range from attoliters or smaller to nanoliters or larger depending upon the nature of the capture objects, the detection technique and equipment employed, the number and density of the wells on the substrate and the expected concentration of capture objects in the fluid applied to the substrate containing the wells. In one embodiment, the size of the reaction vessel may be selected such only a single capture object used for analyte capture can be fully contained within the reaction vessel. In accordance with one embodiment of the present invention, the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the reaction vessels have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

In embodiments where the plurality of capture objects used for analyte capture comprise a plurality of beads and the plurality of locations comprise a plurality of reaction vessels having a shape that is essentially that of a circular cylinder, the size of the reaction vessels may be based upon the size of the beads and may be designed so as to ensure that the number of wells containing more than a single bead is minimal. In some cases, the maximum permissible well diameter may be calculated according to Equation 3:

$$2*BeadRadius + \sqrt{(3*BeadRadius^2 - WellDepth^2 + 2*WellDepth*BeadRadius)} \quad \text{(Eq. 3)}$$

and/or the maximum permissible well depth may be calculated according to Equation 4:

$$BeadRadius + \sqrt{(4*BeadRadius*WellDiameter - WellDiameter^2)} \quad \text{(Eq. 4)}$$

The minimum permissible well depth and the minimum permissible well diameter to assure that a single bead can be contained in the well, in most embodiments, will not be less than the average diameter of the bead. Having a properly sized reaction vessel which allows for no more than a single bead to be present in a reaction vessel may provide better ability to resolve individual beads allowing for more accuracy with regard to determining a measure of the concentration of analyte molecules in a fluid sample by the means described in more detail below and in the Examples. For example, if the reaction vessels are too large, more than one bead may be able to fit in the reaction vessel, which may lead to an increase in the number of reaction vessels containing multiple analyte molecules, which may introduce inaccuracy in a concentration determination using an algorithm/statistical model based on single molecule detection (see below). In some cases, however, it may be desirable to have more than one bead fit in a reaction vessel. On the other hand, in the reaction vessel is too small, a bead may not be able to fit in the reaction vessel, thereby preventing proper sealing of the reaction vessel (e.g., in embodiments where the reaction vessel is sealed) and/or may lead to difficulties in addressing individual locations (e.g., in embodiments where a labeling agent is produced for detection, the labeling agent may disperse away from the reaction vessel it is produced in). In such cases, there may be false positives (e.g., a reaction vessel which does not contain an analyte molecule may be determined to contain an analyte molecule based on the labeling agent which has diffused away from the location in which it was produced) which may lead to imprecise determination of a measure of the concentration of analyte molecules in a fluid sample.

In some embodiments, the average depth of the reaction vessels is between about 1.0 and about 1.7 times, between about 1.0 times and about 1.5 times, between about 1.0 times and about 1.3 times, or between about 1.1 times and about 1.4 times the average diameter of the beads. In some embodiments, the average diameter of the reactions vessels is between about 1.0 times and about 1.9 times, between about 1.2 times and about 1.7 times, between about 1.0 times and about 1.5 times, or between about 1.3 times and about 1.6 times the average diameter of the beads. In a particular embodiment, the average depth of the reaction vessels is between about 1.0 times and about 1.5 times the average diameter of the beads and the average diameter of the reactions vessels is between about 1.0 times and about 1.9 times the average diameter of the beads. The total number of locations and/or density of the locations employed in an assay (e.g., the number/density of reaction vessels in an array) can depend on the composition and end use of the array. For example, the number of reaction vessels employed may depend on the number of capture objects employed, the suspected concentration range of the assay, the method of detection, the size of the capture objects, the type of detection entity (e.g., free labeling agent in solution, precipitating labeling agent, etc.). Arrays containing from about 2 to many billions of reaction vessels (or total number of reaction vessels) can be made by utilizing a variety of techniques and materials. Increasing the number of reaction vessels in the array can be used to increase the dynamic range of an assay or to allow multiple samples or multiple types of analyte molecules to be assayed in parallel. The array may comprise between one thousand and one million reaction vessels per sample to be analyzed. In some cases, the array comprises greater than one million reaction vessels. In some embodiments, the array comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000, or the like, reaction vessels. In some embodiments, the array comprises about 10,000, about 20,000, about 50,000, about 100,000, about 150,000, about 200,000, about 300,000, about 500,000, about 1,000,000, or more, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

A reaction vessel in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels.

In a particular embodiment, an array of reaction vessels is formed by creating microwells on one end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

Alternatively, the equivalent structures of a plurality of reaction vessels may be fabricated using other methods and materials that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding, embossing, and/or etching techniques as will be known to those of ordinary skill in the art.

In certain embodiments, the present invention provides a system equipped with a mechanical platform that applies a sealing component to a substrate. The platform may be positioned beneath a stage on the system. After the chosen reaction components have been added to an array of reaction vessels, the sealing component may be mated with the array. For example, the sealing component may be sandwiched between a flat surface (such as, for example, a microscope slide) and the array of reaction vessels using uniform pressure applied by the mechanical platform.

Figure 7:
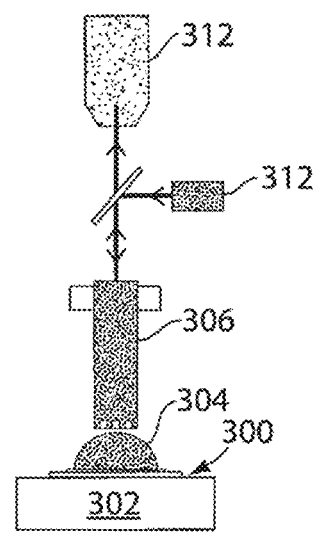
FIG. 7 depicts an experimental set-up for detection using light, according to one embodiment of the present invention.
Figure 8:
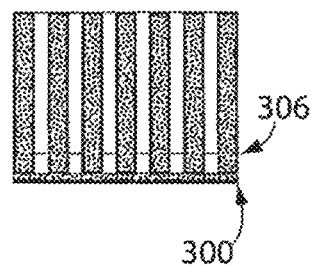
FIG. 8 shows a fiber optic array that has been sealed with a sealing component, according to one embodiment.

A non-limiting embodiment is illustrated in FIG. 7. A sealing component 300 is placed on top of mechanical platform 302. The assay solution 304 is placed on top of the sealing component 300. The mechanical platform is moved upwards towards the array 306 (e.g., fiber optic array) such that uniform pressure is applied. As shown in FIG. 8, the sealing component 300 forms a tight seal with the array 306. In other instances, varying pressure may be applied to the sealing component to form a tight seal between the sealing component and the array. The system may also comprise additional components 312 that may be utilized to analyze the array (e.g., microscope, computer, etc.) as discussed more herein.

The plurality of capture objects used for analyte capture may be spatially separated into the plurality of reaction vessels using any of a wide variety of techniques known to those of ordinary skill in the art. In some cases, the plurality of reaction vessels may be exposed to a solution containing the plurality of capture objects. In some cases, force may be applied to the solution and/or capture objects, thereby aiding in the spatial separation of the capture objects from the fluid phase and/or the deposition of the capture objects in the vessels. For example, after application of an assay solution containing the capture objects to a substrate containing the reaction vessels, the substrate and solution may be centrifuged to assist in depositing the capture objects in the reaction vessels. In embodiments where the capture objects (e.g., beads) are magnetic, a magnet may be used to aid in containing the capture objects in the reaction vessels. In some cases, when the plurality of reaction vessels is formed on the end of a fiber optic bundle (or another planar surface), a material (e.g., tubing) may be placed around the edges of the surface of the array comprising the plurality of reaction vessel to form a container to hold the solution in place while the capture objects settle in the reaction vessels or are placed into the reaction vessels (e.g., while centrifuging). Following placement of the capture objects into at least some of the reaction vessels, the surrounding material may be removed and the surface of the array may be washed and/or swabbed to remove any excess solution/capture objects.

In some embodiments, the substrate does not include wells or reaction vessels forming the plurality of reaction vessels but uses/provides other means to spatially segregate the plurality of capture objects used for analyte capture. In some cases, a patterned substantially planar surface may be employed, wherein the patterned areas form a plurality of locations. In some cases, the patterned areas may comprise substantially hydrophilic surfaces which are substantially surrounded by substantially hydrophobic surfaces. A plurality of capture objects (e.g., beads) may be substantially surround by a substantially hydrophilic medium (e.g., comprising water), and the beads may be exposed to the pattern surface such that the beads associate in the patterned areas (e.g., the locations), thereby spatially segregating the plurality of beads. For example, in one such embodiment, a substrate may be or include a gel or other material able to provide a sufficient barrier to mass transport (e.g., convective and/or diffusional barrier) to prevent capture objects used for analyte capture and/or precursor labeling agent and/or labeling agent from moving from one location on or in the material to another location so as to cause interference or cross-talk between spatial locations containing different capture objects during the time frame required to address the locations and complete the assay. For example, in one embodiment, a plurality of capture objects is spatially separated by dispersing the capture objects on and/or in a hydrogel material. In some cases, a precursor labeling agent may be already present in the hydrogel, thereby facilitating development of a local concentration of the labeling agent (e.g., upon exposure to a binding ligand or analyte molecule carrying an enzymatic component). As still yet another embodiment, the capture objects may be confined in one or more capillaries. In some cases, the plurality of capture objects may be absorbed or localized on a porous or fibrous substrate, for example, filter paper. In some embodiments, the capture objects may be spatially segregated on a uniform surface (e.g., a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein.

Articles and Kits

In some embodiments of the present invention, an article or kit for determining a measure of the concentration of analyte molecules or particles in a fluid sample is provided. The article or kit may comprise a plurality of beads and a substrate comprising a plurality of reaction vessels. The reaction vessels may be configured to receive and contain the capture objects. The plurality of beads in certain embodiment have an average diameter between about 0.1 micrometer and about 100 micrometers and the size of the reaction vessels may be selected such that only either zero or one beads is able to be contained in single reaction vessels. In some cases, the average depth of the reaction vessels is between about 1.0 times and about 1.5 times the average diameter of the beads and the average diameter of the reactions vessels is between about 1.0 times and about 1.9 times the average diameter of the beads. In certain embodiments, the beads may have an average diameter between about between about 1 micrometer and about 10 micrometers, between about 1 micrometer and about 5 micrometers, or any range of sizes described herein.

The plurality of beads provided may have a variety of properties and parameters, as described herein. For example, the beads may be magnetic. The plurality of beads may comprise a binding surface (e.g., a plurality of capture components) having an affinity for at least one type of analyte molecule or particle.

The plurality of reaction vessels may be formed in any suitable substrate, as described herein. In a particular embodiment, the plurality of reaction vessels is formed on the end of a fiber optic bundle. The fiber optic bundle may be prepared (e.g., etched) according to methods known to those of ordinary skill in the art and/or methods described herein. In other embodiments, the plurality of reactions vessels is formed in a plate or similar substantially planar material (e.g., using lithography or other known techniques). Exemplary suitable materials are described herein.

The average depth of the plurality of reaction vessels may be between about 1.0 and about 1.5 times, or between about 1.1 and about 1.3 times the average diameter of the beads, or any range described herein. The average diameter of the plurality of reaction vessels may be between about 1.0 times and about 1.9 times, or between about 1.3 times and about 1.8 times the average diameter of the beads, or any range described herein. The average depth and/or the average diameter of the plurality of reaction vessels may be chosen such that no more than one bead is able to be contained in a reaction vessels. Methods for calculating maximum depths and maximum diameters to facilitate single bead loading are described herein. The average volume of the plurality of reaction vessels may be between about 10 attoliters and about 100 picoliters, between about 1 femtoliter and about 1 picoliter, or any desired range. The substrate may comprise any number of reaction vessels, for example, between about 1,000 and about 1,000,000 reaction vessels, between about 10,000 and about 100,000 reaction vessels, or between about 100,000 and about 300,000 reaction vessels, or any other desired range.

The article or kit may comprise any number of additional components, some of which are described in detail herein. In some cases, the article or kit may further comprise a sealing component configured for sealing the plurality of reaction vessels. In certain embodiments, the plurality of reaction vessels may be formed upon the mating of at least a portion of a sealing component and at least a portion of the second substrate, as shown in FIGS. 7A-7F and as discussed in more detail herein. As another example, the kit may also provide solutions for carrying out an assay method as described herein. Non-limiting example of solutions include solutions containing one or more types of binding ligands and precursor labeling agents. In some cases, the article or kit may comprise at least one type of control bead.

In some embodiments, the kit may optionally include instructions for use of the plurality of beads and the plurality or reaction vessels (and any additional components provided). That is, the kit can include a description of use of the beads and reaction vessels, for example, for use with a system to determine a measure of the concentration of analyte molecules (or particles) in a fluid sample. As used herein, "instructions" can define a component of instruction and/or promotion, and typically involve written instructions on or associated with packaging of the invention. Instructions also can include any oral or electronic instructions provided in any manner such that a user of the kit will clearly recognize that the instructions are to be associated with the kit. Additionally, the kit may include other components depending on the specific application, as described herein. As used herein, "promoted" includes all methods of doing business including methods of education, hospital and other clinical instruction, scientific inquiry, drug discovery or development, academic research, pharmaceutical industry activity including pharmaceutical sales, and any advertising or other promotional activity including written, oral and electronic communication of any form, associated with the invention.

Capture Components

In some embodiments of the present invention, the surface of the capture objects may provide a binding surface having an affinity for at least one type of analyte molecule or particle. In some embodiments, the binding surface may comprise at least one type of capture component. Generally, the capture component allows the attachment of a molecule, particle, or complex to a solid support (that is, a surface of a capture object) for the purposes of immobilization, detection, quantification, and/or other analysis of the molecule, particle, or complex. A capture component is used in the present invention, in some cases, to immobilize an analyte molecule with respect to a capture object (e.g., a bead).

As will be appreciated by those in the art, the composition of the capture component will depend on the composition of the analyte molecule. Capture components for a wide variety of target molecules are known or can be readily found or developed using known techniques. For example, when the target molecule is a protein, the capture components may comprise proteins, particularly antibodies or fragments thereof (e.g., antigen-binding fragments (Fabs), Fab' fragments, pepsin fragments, F(ab')2 fragments, full-length polyclonal or monoclonal antibodies, antibody-like fragments, etc.), other proteins, such as receptor proteins, Protein A, Protein C, etc., or small molecules. In some cases, capture components for proteins comprise peptides. For example, when the target molecule is an enzyme, suitable capture components may include enzyme substrates and/or enzyme inhibitors. In some cases, when the target analyte is a phosphorylated species, the capture component may comprise a phosphate-binding agent. For example, the phosphate-binding agent may comprise metal-ion affinity media such as those describe in U.S. Pat. No. 7,070,921 and U.S. Patent Application No. 20060121544. In addition, when the target molecule is a single-stranded nucleic acid, the capture component may be a complementary nucleic acid. Similarly, the target molecule may be a nucleic acid binding protein and the capture component may be a single-stranded or double-stranded nucleic acid; alternatively, the capture component may be a nucleic acid-binding protein when the target molecule is a single or double stranded nucleic acid. Alternatively, as is generally described in U.S. Pat. Nos. 5,270,163, 5,475,096, 5,567,588, 5,595,877, 5,637,459, 5,683,867, 5,705,337, and related patents, nucleic acid "aptamers" may be developed for capturing virtually any target molecule. Also, for example, when the target molecule is a carbohydrate, potentially suitable capture components include, for example, antibodies, lectins, and selectins. As will be appreciated by those of ordinary skill in the art, any molecule that can specifically associate with a target molecule of interest may potentially be used as a capture component.

For certain embodiments, suitable target analyte molecule/capture component pairs can include, but are not limited to, antibodies/antigens, receptors/ligands, proteins/nucleic acid, nucleic acids/nucleic acids, enzymes/substrates and/or inhibitors, carbohydrates (including glycoproteins and glycolipids)/lectins and/or selectins, proteins/proteins, proteins/small molecules; small molecules/small molecules, etc. According to one embodiment, the capture components are portions (particularly the extracellular portions) of cell surface receptors that are known to multimerize, such as the growth hormone receptor, glucose transporters (particularly GLUT 4 receptor), and T-cell receptors and the target analyte molecules are one or more receptor target ligands.

In a particular embodiment, the capture component may be attached to the surface of a capture object via a linkage, which may comprise any moiety, functionalization, or modification of the binding surface and/or capture component that facilitates the attachment of the capture component to the surface. The linkage between the capture component and the surface may comprise one or more chemical or physical (e.g., non-specific attachment via van der Waals forces, hydrogen bonding, electrostatic interactions, hydrophobic/hydrophilic interactions; etc.) bonds and/or chemical linkers providing such bond(s). In certain embodiments, the capture component comprises a capture extender component. In such embodiments, the capture component comprises a first portion that binds the analyte molecule and a second portion that can be used for attachment to the binding surface.

In certain embodiments, a capture object surface may also comprise a protective or passivating layer that can reduce or minimize non-specific attachment of non-capture components (e.g., analyte molecules, binding ligands) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfo-betaines; naturally occurring long-chain lipids; and nucleic acids, such as salmon sperm DNA.

The method of attachment of the capture component to a capture object surface depends of the type of linkage employed and may potentially be accomplished by a wide variety of suitable coupling chemistries/techniques known to those of ordinary skill in the art. The particular means of attachment selected will depend on the material characteristics of the capture object surface and the nature of the capture component. In certain embodiments, the capture components may be attached to the capture object surface through the use of reactive functional groups on each. According to one embodiment, the functional groups are chemical functionalities. That is, the binding surface may be derivatized such that a chemical functionality is presented at the binding surface which can react with a chemical functionality on the capture component resulting in attachment. Examples of functional groups for attachment that may be useful include, but are not limited to, amino groups, carboxy groups, epoxide groups, maleimide groups, oxo groups, and thiol groups. Functional groups can be attached, either directly or through the use of a linker, the combination of which is sometimes referred to herein as a "crosslinker." Crosslinkers are known in the art; for example, homo- or hetero-bifunctional crosslinkers as are well known (e.g., see 1994 Pierce Chemical Company catalog, technical section on crosslinkers, pages 155-200, or "Bioconjugate Techniques" by Greg T. Hermanson, Academic Press, 1996). Non-limiting example of crosslinkers include alkyl groups (including substituted alkyl groups and alkyl groups containing heteroatom moieties), esters, amide, amine, epoxy groups and ethylene glycol and derivatives. A crosslinker may also comprise a sulfone group, forming a sulfonamide.

According to one embodiment, the functional group is a light-activated functional group. That is, the functional group can be activated by light to attach the capture component to the capture object surface. One example is PhotoLink™ technology available from SurModics, Inc. in Eden Prairie, Minn.

In some cases, the capture object may comprise streptavidin-coated surfaces and the capture component may be biotinylated. Exposure of the capture component to the streptavidin-coated surfaces can cause association of the capture component with the surface by interaction between the biotin component and streptavidin.

In certain embodiments, attachment of the capture component to the binding surface may be effected without covalently modifying the binding surface of a capture object. For example, the attachment functionality can be added to the binding surface by using a linker that has both a functional group reactive with the capture component and a group that has binding affinity for the binding surface. In certain embodiments, a linker comprises a protein capable of binding or sticking to the binding surface; for example, in one such embodiment, the linker is serum albumin with free amine groups on its surface. A second linker (crosslinker) can then be added to attach the amine groups of the albumin to the capture component (e.g., to carboxy groups).

According to one embodiment in which a chemical crosslinker is used to attach the capture components to the capture object, the analyte molecule may be captured on the binding surface of a capture object using a capture component attached via chemical crosslinking in the following manner. First, the binding surface is derivatized with a functional group, such as, an amine group. Next, a crosslinker and the capture component are placed in contact with the binding surface such that one end of the crosslinker attaches to the amine group and the capture component attaches to the other end of the crosslinker. In this way, capture components comprising proteins, lectins, nucleic acids, small organic molecules, carbohydrates can be attached.

One embodiment utilizes proteinaceous capture components. As is known in the art, any number of techniques may be used to attach a proteinaceous capture component to a wide variety of solid surfaces. "Protein" or "proteinaceous" in this context includes proteins, polypeptides, peptides, including, for example, enzymes, and antibodies. A wide variety of techniques are known to add reactive moieties to proteins, for example, the method outlined in U.S. Pat. No. 5,620,850. The attachment of proteins to surfaces is known, for example, see Heller, *Acc. Chem. Res.* 23:128 (1990), and many other similar references.

In some embodiments, the capture component (or binding ligand) may comprise Fab' fragments. The use of Fab' fragments as opposed to whole antibodies may help reduce non-specific binding between the capture component and the binding ligand. In some cases, the Fc region of a capture component (or binding ligand) may be removed (e.g., proteolytically). In some cases, an enzyme may be used to remove the Fc region (e.g., pepsin, which may produce F(ab')2 fragments and papain, which may produce Fab fragments). In some instances, the capture component may be attached to a binding surface using amines or may be modified with biotin (e.g., using NHS-biotin) to facilitate binding to an avidin or streptavidin coated capture object surface. F(ab')2 fragments may be subjected to a chemical reduction treatment (e.g., by exposure to 2-mercaptoethylamine) to, in some cases, form two thiol-bearing Fab' fragments. These thiol-bearing fragments can then be attached via reaction with a Michael acceptor such as maleimide. For example, the Fab' fragments may then be treated with a reagent (e.g., maleimide-biotin) to attach at least one biotin moiety (i.e., biotinylated) to facilitate attachment to streptavidin-coated surfaces as described above.

Certain embodiments utilize nucleic acids as the capture component, for example for when the analyte molecule is a nucleic acid or a nucleic acid binding protein, or when the it is desired that the capture component serve as an aptamer for binding a protein, as is well known in the art.

According to one embodiment, each binding surface of a capture object comprises a plurality of capture components. The plurality of capture components, in some cases, may be distributed randomly on the binding surface like a "lawn." Alternatively, the capture components may be spatially segregated into distinct region(s) and distributed in any desired fashion.

Binding between the capture component and the analyte molecule, in certain embodiments, is specific, e.g., as when the capture component and the analyte molecule are complementary parts of a binding pair. In certain such embodiments, the capture component binds both specifically and directly to the analyte molecule. By "specifically bind" or "binding specificity," it is meant that the capture component binds the analyte molecule with specificity sufficient to differentiate between the analyte molecule and other components or contaminants of the test sample. For example, the capture component, according to one embodiment, may be an antibody that binds specifically to some portion of an analyte molecule (e.g., an antigen). The antibody, according to one embodiment, can be any antibody capable of binding specifically to an analyte molecule of interest. For example, appropriate antibodies include, but are not limited to, monoclonal antibodies, bispecific antibodies, minibodies, domain antibodies, synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the capture component may be an antigen.

According to one embodiment in which an analyte particle is a biological cell (e.g., mammalian, avian, reptilian, other vertebrate, insect, yeast, bacterial, cell, etc.), the capture component may be a ligand having specific affinity for a cell surface antigen (e.g., a cell surface receptor). In one embodiment, the capture component is an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell. In one embodiment in which the analyte particle is a cell, the capture component is fibronectin, which has specificity for, for example, analyte particles comprising neural cells.

In some embodiments, as will be appreciated by those of ordinary skill in the art, it is possible to detect analyte molecules using capture components for which binding to analyte molecules is not highly specific. For example, such systems/methods may use different capture components such as, for example, a panel of different binding ligands, and detection of any particular analyte molecule is determined via a "signature" of binding to this panel of binding ligands, similar to the manner in which "electronic noses" work. This may find particular utility in the detection of certain small molecule analytes. In some embodiments, the binding affinity between analyte molecules and capture components should be sufficient to remain bound under the conditions of the assay, including wash steps to remove molecules or particles that are non-specifically bound. In some cases, for example in the detection of certain biomolecules, the binding constant of the analyte molecule to its complementary capture component may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or the like. For example, typical affinities for IgG antibodies for their antigens are in the range $10^5$-$10^{10}$ $M^{-1}$. The affinity of biotin for streptavidin is $10^{15}$ $M^{-1}$.

In certain embodiments, the capture component is chosen to be able to bind to a corresponding binding partner associated with or attached to the analyte molecule. For example, the capture component according to one embodiment is a chemical crosslinker as described above able to bind to proteins generally. According to one embodiment, every protein molecule in a fluid sample comprises an analyte molecule that attaches to such a chemical crosslinker. In another example, the capture component comprises streptavidin, which binds with high affinity to biotin, and thus captures any analyte molecules to which biotin has been attached. Alternatively, the capture component may be biotin, and streptavidin may be attached to or associated with the analyte molecules such that the analyte molecules can be captured by the biotin.

According to one embodiment, the binding surfaces of a capture object may be functionalized with capture components in the following manner. First, the surface of a capture object is prepared for attachment of the capture component(s) by being modified to form or directly bind to the capture components, or a linker may be added to the binding surface of the capture object such that the capture component(s) attaches to the binding surface of the capture object via the linker. In one embodiment, the binding surfaces of the capture object are derivatized with a chemical functionality as described above. Next, the capture component may be added, which binds to and is immobilized by the chemical functionality.

Exemplary Target Analytes

As will be appreciated by those in the art, a large number of analyte molecules and particles may be detected and, optionally, quantified using methods and systems of the present invention; basically, any analyte molecule that is able to be made to become immobilized with respect to a capture object (e.g., via a binding surface comprising a plurality of capture components) can be potentially investigated using the invention. Certain more specific targets of potential interest that may comprise an analyte molecule are mentioned below. The list below is exemplary and non-limiting.

In some embodiments, the analyte molecule may be an enzyme. Non-limiting examples of enzymes include, an oxidoreductase, transferase, kinase, hydrolase, lyase, isomerase, ligase, and the like. Additional examples of enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When a system/method of the present invention is used to detect the presence of viral or bacterial agents, appropriate target enzymes include viral or bacterial polymerases and other such enzymes, including viral or bacterial proteases, or the like.

In other embodiments, the analyte molecule may comprise an enzymatic component. For example, the analyte particle can be a cell having an enzyme or enzymatic component present on its extracellular surface. Alternatively, the analyte particle is a cell having no enzymatic component on its surface. Such a cell is typically identified using an indirect assaying method described below. Non-limiting example of enzymatic components are horseradish peroxidase, beta-galactosidase, and alkaline phosphatase.

In yet other embodiments, the analyte molecule may be a biomolecule. Non-limiting examples of biomolecules include hormones, antibodies, cytokines, proteins, nucleic acids, lipids, carbohydrates, lipids cellular membrane antigens and receptors (neural, hormonal, nutrient, and cell surface receptors) or their ligands, or combinations thereof. Non-limiting embodiments of proteins include peptides, polypeptides, protein fragments, protein complexes, fusion proteins, recombinant proteins, phosphoproteins, glycoproteins, lipoproteins, or the like. As will be appreciated by those in the art, there are a large number of possible proteinaceous analyte molecules that may be detected or evaluated for binding partners using the present invention. In addition to enzymes as discussed above, suitable protein analyte molecules include, but are not limited to, immunoglobulins, hormones, growth factors, cytokines (many of which serve as ligands for cellular receptors), cancer markers, etc. Non-limiting examples of biomolecules include PSA and TNF-alpha.

In certain embodiments, the analyte molecule may be a host-translationally modified protein (e.g., phosphorylation, methylation, glycosylation) and the capture component may be an antibody specific to a post-translational modification. Modified proteins may be captured with capture components comprising a multiplicity of specific antibodies and then the captured proteins may be further bound to a binding ligand comprising a secondary antibody with specificity to a post-translational modification. Alternatively, modified proteins may be captured with capture components comprising an antibody specific for a post-translational modification and then the captured proteins may be further bound to binding ligands comprising antibodies specific to each modified protein.

In another embodiment, the analyte molecule is a nucleic acid. A nucleic acid may be captured with a complementary nucleic acid fragment (e.g., an oligonucleotide) and then optionally subsequently labeled with a binding ligand comprising a different complementary oligonucleotide.

Suitable analyte molecules and particles include, but are not limited to small molecules (including organic compounds and inorganic compounds), environmental pollutants (including pesticides, insecticides, toxins, etc.), therapeutic molecules (including therapeutic and abused drugs, antibiotics, etc.), biomolecules (including hormones, cytokines, proteins, nucleic acids, lipids, carbohydrates, cellular membrane antigens and receptors (neural, hormonal, nutrient, and cell surface receptors) or their ligands, etc), whole cells (including prokaryotic (such as pathogenic bacteria) and eukaryotic cells, including mammalian tumor cells), viruses (including retroviruses, herpesviruses, adenoviruses, lentiviruses, etc.), spores, etc.

The fluid sample containing or suspected of containing an analyte molecule may be derived from any suitable source. In some cases, the sample may comprise a liquid, fluent particulate solid, fluid suspension of solid particles, supercritical fluid, and/or gas. In some cases, the analyte molecule may be separated or purified from its source prior to determination; however, in certain embodiments, an untreated sample containing the analyte molecule may be tested directly. The source of the analyte molecule may be synthetic (e.g., produced in a laboratory), the environment (e.g., air, soil, etc.), a mammal, an animal, a plant, or any combination thereof. In a particular example, the source of an analyte molecule is a human bodily substance (e.g., blood, serum, plasma, urine, saliva, tissue, organ, or the like). The volume of the fluid sample analyzed may potentially be any amount within a wide range of volumes, depending on a number of factors such as, for example, the number of capture objects used/available, the number of locations us/available, etc. In a few particular exemplary embodiments, the sample volume may be about 0.01 ul, about 0.1 uL, about 1 uL, about 5 uL, about 10 uL, about 100 uL, about 1 mL, about 5 mL, about 10 mL, or the like. In some cases, the volume of the fluid sample is between about 0.01 uL and about 10 mL, between about 0.01 uL and about 1 mL, between about 0.01 uL and about 100 uL, or between about 0.1 uL and about 10 uL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, or greater, prior to use. The sample may be added to a solution comprising the plurality of capture objects, or the plurality of capture objects may be added directly to or as a solution to the sample.

Binding Ligands and Precursor Labeling Agents/Labeling Agent

Binding ligands may be selected from any suitable molecule, particle, or the like, as discussed more below, able to associate with an analyte molecule and/or to associate with another binding ligand. Certain binding ligands can comprise an entity that is able to facilitate detection, either directly (e.g., via a detectable moiety) or indirectly. A component may facilitate indirect detection, for example, by converting a precursor labeling agent molecule into a labeling agent molecule (e.g., an agent that is detected in an assay). In some embodiments, the binding ligand may comprise an enzymatic component (e.g., horseradish peroxidase, beta-galactosidase, alkaline phosphatase, etc). A first type of binding ligand may or may not be used in conjunction with additional binding ligands (e.g., second type, etc.), as discussed herein.

In some embodiments, the plurality of capture objects, at least some of which comprise at least one analyte molecule, may be exposed to a plurality of binding ligands such that a binding ligand associates with at least some of the plurality of analyte molecules. In embodiments where a statistically significant fraction of the capture objects are associated with a single analyte molecule and a statistically significant fraction of the capture objects are not associated with any analyte molecules (e.g., where the number of analyte molecules is less than the total number of capture objects), a binding ligand may associate with substantially all of the analyte molecules immobilized with respect to a capture object. In some cases, greater than about 80%, greater than about 85%, greater than about 90%, greater than about 95%, greater than about 97%, greater than about 98%, greater than about 99%, or more, analyte molecules may become associated with a binding ligand.

In other embodiments where substantially all of the capture objects comprise at least one analyte molecule (e.g., in embodiments where the number of analyte molecules is about equal to or greater than the number of capture objects provided), the capture objects may be exposed to the binding ligand such that a statistically significant fraction of the capture objects associate with at least one binding ligand (or in certain embodiments substantially only a single binding ligand) and a statistically significant fraction of the capture objects do not associate with any binding ligand. In some cases, the capture objects may be exposed to the binding ligands such that at least some of the capture objects associate with at least one binding ligand and a statistically significant fraction of the capture objects do not associate with any binding ligand. A screening test to determine an appropriate amount of binding ligand to use for a desired degree of binding ligand loading (e.g. to facilitate selection of an appropriate quantity of binding ligand to use for a particular situation) may be performed with calibration standards containing a known concentration of analyte molecule and varying quantities of binding ligand using a Poisson analysis. In certain embodiments, it is determined whether the analyte is essentially fully labeled or only partially labeled with binding ligand. The percentage active analyte molecules (i.e. those associated with binding ligand) detected can be converted to the percentage analyte molecules associated with zero, one, two etc. binding ligands using Poisson distribution adjustment as described elsewhere herein.

In some embodiments, more than one type of binding ligand may be used. In some embodiments, a first type of binding ligand and a second type of binding ligand may be provided. In some instances, at least two, at least three, at least four, at least five, at least eight, at least ten, or more, types of binding ligands may be provided. When a plurality of capture objects, some of which are associated with at least one analyte molecule, are exposed to a plurality of types of binding ligand, at least some of the plurality of immobilized analyte molecules may associate with at least one of each type of binding ligand. The binding ligands may be selected such that they interact with each other in a variety of different manners. In a first example, the first type of binding ligand may be able to associate with an analyte molecule and the second type of binding ligand may be able to associate with the first type of binding ligand. In such embodiments, the first type of binding ligand may comprise a first component which aids in association of the analyte molecule and a second component which aids in association of the second type of binding ligand with the first type of binding ligand. In a particular embodiment, the second component is biotin and the second type of binding ligand comprises an enzyme or an enzymatic component which associates with the biotin.

As another example, both the first type of binding ligand and the second type of binding ligand may associate directly with an analyte molecule. Without being bound by theory or any particular mechanism, the association of both the first type and the second type of binding ligand may provide additional specificity and reliability in performing an assay, by identifying only locations which are determined to contain both the first type of binding ligand and/or the second type of binding ligand (e.g., either through direct or indirect detection) as containing an analyte molecule. Such assay methods may reduce the number of false positives caused by non-specific binding as locations that are found to only have a single type of binding ligand (e.g., only the first type of labeling agent or the second type of labeling agent) would be not be considered or counted as a location comprising an analyte molecule. The first type of binding ligand may comprise a first type of enzymatic component and the second type of binding ligand may comprise a second type of enzymatic component which differs from the first type of enzymatic component. A capture object comprising an analyte molecule, the first type of binding ligand, and the second type of binding ligand may be exposed to a first type of precursor labeling agent which is converted to a first type of labeling agent (e.g., comprising a first measurable property) upon exposure to the first type of enzymatic component and a second type of precursor labeling agent which is converted to a second type of labeling agent (e.g., comprising a measurable property which is distinguishable from the first measurable property) upon exposure to the second type of enzymatic component. Therefore, only locations which are determined to contain the first type of labeling agent and the second type of labeling agent are determined to contain an analyte molecule. As another example, the first type of binding ligand and the second type of binding ligand may each incorporate a component (e.g., such as a DNA label) and a third type of binding ligand may comprise two components complimentary to the components of the first type and second type of binding ligands (e.g., two types of complimentary DNA labels), wherein the third type of binding ligand also comprises an molecule or moiety for direct or indirect detection (e.g., the presence of the third type of binding ligand in a reaction vessel is required to determine the presence or absence of an analyte molecule in a location). When both the first type of binding ligands and the second types of binding ligands are present in substantially close proximity to each other (e.g., via association with an analyte molecule) association of the third type of binding ligand may occur, thus allowing detection of the analyte molecule. More information regarding the use of more than one type of binding ligand in a manner which may reduce certain negative affects associated with non-specific binding, are described in commonly owned U.S. patent application Ser. No. (not yet determined), entitled "Ultra-Sensitive Detection of Molecules using Dual Detection Methods" by Duffy et al., filed Mar. 24, 2010, Ser. No. 12/731,136 incorporated by reference.

Detection

The plurality of capture objects, some of which comprise at least one analyte molecule and/or at least one binding ligand can be detected and/or quantified, and the detection and/or quantification can be related to the presence and, optionally, the quantity and/or concentration of analyte molecules/particles in the sample being tested. In some embodiments, the plurality of capture objects may be detected and/or quantified by spatially segregating the plurality of capture objects into a plurality of locations. In some embodiments, the plurality of locations comprises a plurality of reaction vessels (e.g., in an array). In some cases, a detector may be configured to detect the capture objects in or at a plurality of locations (e.g., an array of reaction vessels). In some embodiments, the capture objects may be able to produce or be made to produce a detectable signal, for example, fluorescence emission, which may aid in the detection of the capture objects. In some cases, the capture objects may be detected using scattering techniques, as described herein.

In some embodiments, the number of capture objects spatially segregated may be substantially equal to the number of capture objects exposed to a fluid sample containing or suspected of containing analyte molecules. In some embodiments, however, the number of capture objects spatially segregated into a plurality of locations may be substantially less than the number of capture objects exposed to a fluid sample containing or suspected of containing analyte molecules. In some cases, about 1%, about 2%, about 3%, about 5%, about 10%, about 15%, about 20%, about 30%, about 40%, about 50%, about 60%, about 70%, about 80%, or more, of the capture objects exposed to a fluid sample are spatially segregated into a plurality of locations. In some instances, between about 1% and about 99%, between about 10% and about 90%, between about 20% and about 80%, between about 30% and about 70%, between about 50% and about 90%, between about 1% and about 50%, between about 5% and about 40%, or between about 10% and about 30% of the capture objects exposed to a fluid sample are spatially segregated into a plurality of locations.

The analyte molecules (or binding ligands) which are spatially segregated may be detected and/or quantified directly or indirectly. In the case of direct detection, the analyte molecules may comprise a molecule or moiety that may be directly interrogated and/or detected, for example, a fluorescent entity (e.g., a fluorescent moiety, fluorescent bead, fluorescent antibody, etc.), a metal nanoparticle or nanocluster (e.g., a gold nanocluster or nanoparticle, silver nanocluster or nanoparticle), a quantum dot (e.g., CdSe quantum dot, CdTe quantum dot, etc.), and radioactive isotopes. In embodiments where the assay comprises the use of one or more types of binding ligands, the binding ligands may comprise a molecule(s) or moiety(ies) that may be directly interrogated and/or detected. A location that comprises such an analyte molecule or binding ligand which comprises a moiety that may be directly interrogated and/or detected can be made to emit a signal upon interrogation of the location.

In some embodiments, non-enzymatic detection methods may be employed. Non-enzymatic detection methods will be known to those of ordinary skill in the art. Non-limiting examples include Raman scattering, electromagnetic radiation resonance methods (e.g., whispering gallery modes), spectroscopy (e.g., infrared, atomic spectroscopies), absorbance, piezoelectric transduction (e.g., quartz crystal microbalance (QCM)), circular dichroism, electron microscopies (e.g., scanning electron microscopy (SEM), x-ray photoelectron microscopy (XPS)), scanning probe microscopies (e.g., atomic force microscopy (AFM), scanning tunneling microscopy (STM)), light scattering; surface plasmon resonance (SPR), evanescent wave detection, optical interferometry and other methods based on measuring changes in refractive index, electrical transduction methods, such as conduction and capacitance; magnetic transduction effects (e.g., magnetoresistive effect), calorimetry (e.g., differential scanning calorimetry (DSC)), diffraction; nuclear magnetic resonance (NMR), electron paramagnetic resonance (EPR), mass spectroscopy (e.g., matrix assisted laser desorption and ionization (MALDI)), fluorescence technologies (e.g., fluorescence resonance energy transfer (FRET), time-resolved fluorescence (TRF), fluorescence polarization (FP)), and luminescent oxygen channeling (LOCI).

In some embodiments, the plurality of analyte molecules (or binding ligands) are indirectly detected. The indirect approach can include, for example, exposing an analyte molecule, or a binding ligand associated with an analyte molecule, to a precursor labeling agent, wherein the precursor labeling agent is converted into a labeling agent upon exposure to the analyte molecule or the binding ligand associated with an analyte molecule. The labeling agent may comprise a molecule or moiety that can be interrogated and/or detected. The presence or absence of an analyte molecule or binding ligand at a location may then be determined by determining the presence or absence of a labeling agent at/in the location. For example, the analyte molecule may comprise an enzymatic component and the precursor labeling agent molecule may be a chromogenic, fluorogenic, or chemiluminescent enzymatic precursor labeling agent molecule which is converted to a chromogenic, fluorogenic, or chemiluminescent product (each an example of a labeling agent) upon exposure to the converting agent. In this instance, the precursor labeling agent may be an enzymatic label, for example, a chromogenic, fluorogenic, or chemiluminescent enzymatic precursor labeling agent, that upon contact with the enzymatic component, is converted into a labeling agent, which is detectable. In some cases, the chromogenic, fluorogenic, or chemiluminescent enzymatic precursor labeling agent is provided in an amount sufficient to contact every location. In some embodiments, an electrochemiluminescent precursor labeling agent is converted to an electrochemiluminescent labeling agent. In some cases, the enzymatic component may comprise beta-galactosidase, horseradish peroxidase, or alkaline phosphatase.

As will be understood by those of ordinary skill in the art, a variety of appropriate chromogenic, fluorogenic, or chemiluminescent enzymatic precursor labeling agents may be selected for conversion by many different enzymes. Thus, any known chromogenic, fluorogenic, or chemiluminescent enzyme precursor labeling agent capable of producing a labeling agent in a reaction with a particular enzyme can potentially be used in the present invention as the precursor labeling agent in embodiments where the analyte molecule or a binding ligand associated with an analyte molecule comprises an enzymatic component. For example, many chromogenic, fluorogenic, or chemiluminescent precursor labeling agent suitable for use an enzymatic precursor labeling agent molecule are disclosed in *The Handbook—A Guide to Fluorescent Probes and Labeling Technologies*, Tenth Ed., Chapter 10.

In another embodiment, the analyte molecule may be a protein and the binding ligand may comprise a component which is capable of binding both to the analyte molecule and an enzymatic component. Exposure of the precursor labeling agent molecule to the enzymatic component bound to the binding ligand may convert the precursor labeling agent molecule to a chromogenic, fluorogenic, of chemiluminescent labeling agent molecule that may be detected.

Figure 9A:
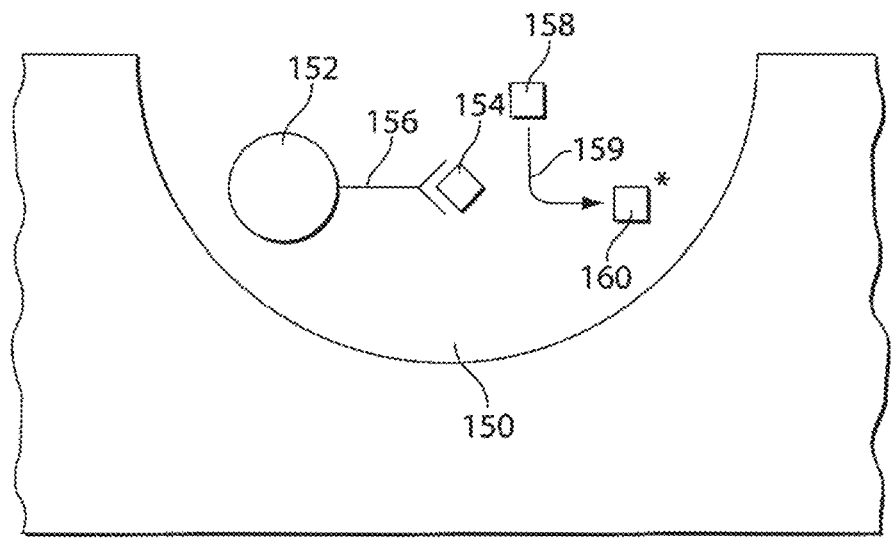
FIG. 9A shows a schematic diagram depicting a method of indirectly detecting an analyte molecule associated with a capture object, according to some embodiments.
Figure 9B:
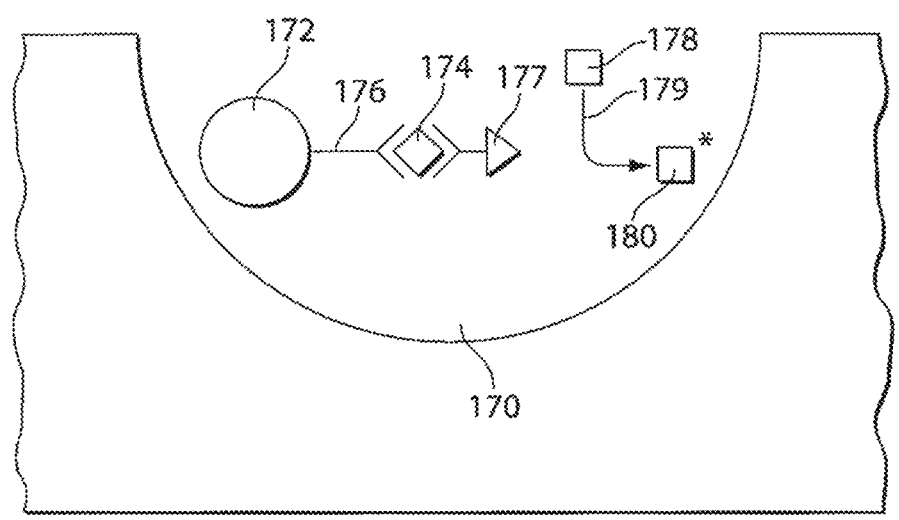
FIG. 9B shows a schematic diagram depicting a method of indirectly detecting an analyte molecule immobilized with respect to a capture object using a binding ligand, according to some embodiments.

Two non-limiting examples of indirect detection of an analyte molecule are illustrated in FIGS. 9A and 9B. In FIG. 9A, a location 150 (in this embodiment, represented by a reaction vessel) is provided which comprises capture object 152 (in this embodiment, represented by a bead). Analyte molecule 154 is immobilized with respect to capture object 152 via capture component 156. The reaction vessel is exposed to precursor labeling agent 158, which upon exposure to analyte molecule 154, is converted to labeling agent molecule 160, as indicated by arrow 159. As another example, in FIG. 9B, location 170 (in this embodiment, represented by a reaction vessel) is provided which comprises capture object 172 (in this embodiment, represented by a bead). Analyte molecule 174 is immobilized with respect to capture object 172 via capture component 176, and binding ligand 177 is associated with analyte molecule 174. The reaction vessel is exposed to precursor labeling agent 158, which upon exposure to binding ligand 177, is converted to a labeling agent molecule 180, as indicated by arrow 179.

In some embodiments, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection can be accomplished by using various techniques, including optical techniques (e.g., CCD detector). Spatially segregating capture objects/species/molecules/particles into a plurality of discrete, resolvable locations, according to some embodiments facilitates substantially simultaneous detection by allowing multiple locations to be addressed substantially simultaneously. For example, for embodiments where individual species/molecules/particles are associated with capture objects that are spatially segregated with respect to the other capture objects into a plurality of discrete, separately resolvable locations during detection, substantially simultaneously addressing the plurality of discrete, separately resolvable locations permits individual capture objects, and thus individual species/molecules/particles (e.g., analyte molecules) to be resolved. For example, in certain embodiments, individual molecules/particles of a plurality of molecules/particles are partitioned across a plurality of reaction vessels such that each reaction vessel contains zero or only one species/molecule/particle. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection. A plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In some embodiments, the plurality of species/molecules/particles may be detected substantially simultaneously within a time period of between about 100 microseconds and about 0.001 microseconds, between about 10 microseconds and about 0.01 microseconds, or less.

During the step of the method where the locations into which the capture objects/analyte molecules have been segregated are addressed, any of a variety of parameters may be determined. In some embodiments, the number of locations which comprise a capture object and an analyte molecule (or binding ligand) is determined. The number of locations which comprise a capture object but do not comprise an analyte molecule (or binding ligand) may also be determined. In some cases, the number of locations which are addressed which do not contain a capture object may also be determined. In still yet other cases, the total number of locations addressed may also be determined. A single interrogation or multiple interrogations of any subset or all of the locations ultimately addressed may be made at any given time to facilitate one or all of the above described determinations. For example, a first determination may be completed under a first range of wavelengths (e.g., white light) to determine the number of locations comprising a capture object, wherein the locations are not distinguished as to whether an analyte molecule (or binding ligand) is associated with the capture object, and a second determination of the same or some subset of the locations may be completed under a second range of wavelengths (e.g., fluorescence) to determine the number of locations which comprise a capture object associated with an analyte molecule (or binding ligand). Exemplary detection methods are described below.

Detection Methods

In some embodiments, in the systems/methods in which the species to be detected are partitioned across a plurality of locations, the locations can be interrogated using a variety of techniques, including techniques known to those of ordinary skill in the art.

In a specific embodiment of the present invention, the locations are optically interrogated. The locations exhibiting changes in their optical signature may be identified by a conventional optical train and optical detection system. Depending on the detected species (e.g., labeling agent molecules, particles, etc.) and the operative wavelengths, optical filters designed for a particular wavelength may be employed for optical interrogation of the locations.

In embodiments where optical interrogation is used, the system may comprise more than one light source and/or a plurality of filters to adjust the wavelength and/or intensity of the light source. For example, in some cases, a first interrogation of the locations may be conducted using light of a first range of wavelengths (e.g., white light in embodiments where the capture objects are not fluorescent, or a wavelength range where the capture objects fluoresce), whereas a second interrogation is conducted using light of a second, differing range of wavelengths, such that the plurality of detectable molecules fluoresce. An exemplary system configuration is provided below (see FIG. 10).

In some embodiments, the optical signal from a plurality of locations is captured using a CCD camera Other non-limiting examples of camera imaging types that can be used to capture images include charge injection devices (CIDs), complimentary metal oxide semiconductors (CMOSs) devices, scientific CMOS (sCMOS) devices, and time delay integration (TDI) devices, as will be known to those of ordinary skill in the art. The camera may be obtained from a commercial source. CIDs are solid state, two dimensional multi pixel imaging devices similar to CCDs, but differ in how the image is captured and read. For examples of CIDs, see U.S. Pat. Nos. 3,521,244 and 4,016,550. CMOS devices are also two dimensional, solid state imaging devices but differ from standard CCD arrays in how the charge is collected and read out. The pixels are built into a semiconductor technology platform that manufactures CMOS transistors thus allowing a significant gain in signal from substantial readout electronics and significant correction electronics built onto the device. For example, see U.S. Pat. No. 5,883,830. sCMOS devices comprise CMOS imaging technology with certain technological improvements that allows excellent sensitivity and dynamic range. TDI devices employs a CCD device that allows columns of pixels to be shifted into and adjacent column and allowed to continue gathering light. This type of device is typically used in such a manner that the shifting of the column of pixels is synchronous with the motion of the image being gathered such that a moving image can be integrated for a significant amount of time and is not blurred by the relative motion of the image on the camera. In some embodiments, a scanning mirror system coupled with a photodiode or photomultiplier tube (PMT) could be used to for imaging.

In one embodiment, the plurality of locations is formed directly as a plurality of reaction vessels in an end of a fiber optic bundle. According to one embodiment, the array of reaction vessels for the present invention can be used in conjunction with an optical detection system such as the system described in U.S. Publication No. 2003/0027126. For example, according to one embodiment, the array of reaction vessels of the present invention is formed in one end of a fiber optic assembly comprising a fiber optic bundle constructed of clad fibers so that light does not mix between fibers.

Figure 10A:
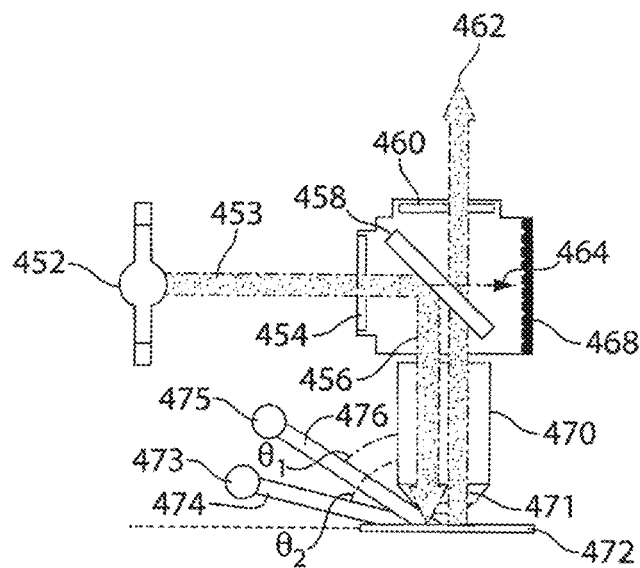
FIGS. 10A and 10B show non-limiting examples of a system employing an optical detection system of the present invention according to some embodiments.
Figure 10B:
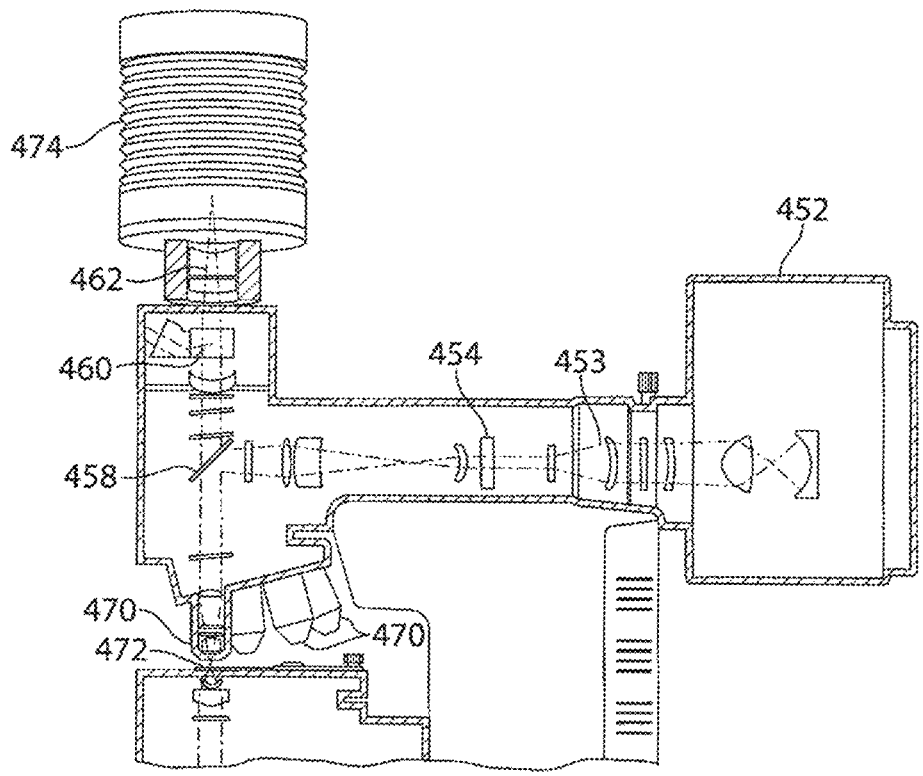

FIGS. 10A and 10B show non-limiting examples of a system of the present invention according to some embodiments. The system comprises a light source 452, excitation filter 454, dichromatic mirror 458, emission filter 460, objective 470, and array 472. Light 453 given off from light source 452 is passed through excitation filter 454. The light reflects off dichromatic mirror 458, passes through objective 470 and shines on array 472. In some cases, stray light 464 may be reduced by a stray light reducing function 468, such as an iris or aperture. Light 471 emitted from the array passes through objective 470 and emission filter 460. Light 462 is observed. The system may comprise additional components (e.g., additional filters, mirrors, magnification devices, etc.) as needed for particular applications, as would be understood by those of ordinary skill in the art.

The system shown in FIG. 10A may additionally comprise components which aid in the determination of the number of reaction vessels which contain a capture object (e.g., using white light). Alternatively, the additional components may be used to determine the total number of locations and/or provide spatially information regarding the position of the locations (e.g., containing or not containing a capture object), which may help corroborate signals observed under different light regimes (e.g., fluorescence, white light) corresponding with the position of a location (e.g., a mask may be created).

In FIGS. 10A and 10B, excitation light is emitted from source 452 and collimated into a beam 453. The excitation filter 454 may be configured to transmit only the wavelength band that excites the fluorophore (e.g., 575 nm+/−10 nm for resorufin). The excitation light is reflected downward by the dichroic filter 458 and excites the substrate 472 containing the sample through the objective lens 470. The image light is collected by the objective lens 470, collimated into a beam 471 and transmitted through the dichroic filter 458. Only the image light corresponding to the fluorescence wavelength band (e.g., 670 nm+/−30 nm for resorufin) is transmitted through the emission filter 460. The remaining collimated beam 462 contains only the emitted fluorescence wavelengths which will subsequently be imaged through the camera system.

The same system may be used to determine the positioning of the locations containing sample (e.g., reaction vessels). The array comprising the reaction vessels containing capture objects may be illuminated with a "bright field" white light illumination. The array may be illuminated (e.g., using light source 475 shown in FIG. 10A) by directing a pseudo-collimated white light (e.g., white light LED) onto the array surface from an angle (e.g., $\theta_1$ in FIG. 10A may be about 20 degrees, about 25 degrees, about 30 degrees, about 35 degrees, about 40 degrees, or greater) just outside the numerical aperture of the collection objective. Light that hits the surface of the array 472 (e.g., light 476) is reflected (and scattered) off the surface, collimated 471, and collected by the objective lens (470). The collimated beam is subsequently imaged through the camera system.

The same system may also be used to determine which locations contain a capture object (e.g., bead). Any particular bead may or may not be associated with an analyte molecule and/or binding ligand. The array may be illuminated (e.g., using light source 473 as shown in FIG. 10A) with a "dark field" white light illumination. The array may be illuminated by aiming a pseudo-collimated white light (e.g., white light LED 473) onto the array surface from an angle (e.g., θ2 in FIG. 10A is about 65 degrees, about 70 degrees, about 75 degrees, about 80 degrees, about 85 degrees) substantially outside the numerical aperture of the collection objective. Light that hits the surface of the array 472 (e.g., light 474) is reflected (and scattered) off the surface, collimated 471, and collected by the objective lens 470. The collimated beam is subsequently imaged by the camera system.

In some embodiments, an optical detection system may be employed, for example, as described in U.S. Publication No. 2003/0027126. In an exemplary system, light returning from an array of reaction vessels formed at the distal end of a fiber optic bundle is altered via use of a magnification changer to enable adjustment of the image size of the fiber's proximal or distal end. The magnified image is then shuttered and filtered by a shutter wheel. The image is then captured by charge coupled device (CCD) camera. A computer may be provided that includes and executes imaging processing software to process the information from the CCD camera and also optionally may be configured to control shutter and filter wheels. As depicted in U.S. Publication No. 20030027126, the proximal end of the bundle is received by a z-translation stage and x-y micropositioner.

Figure 11:
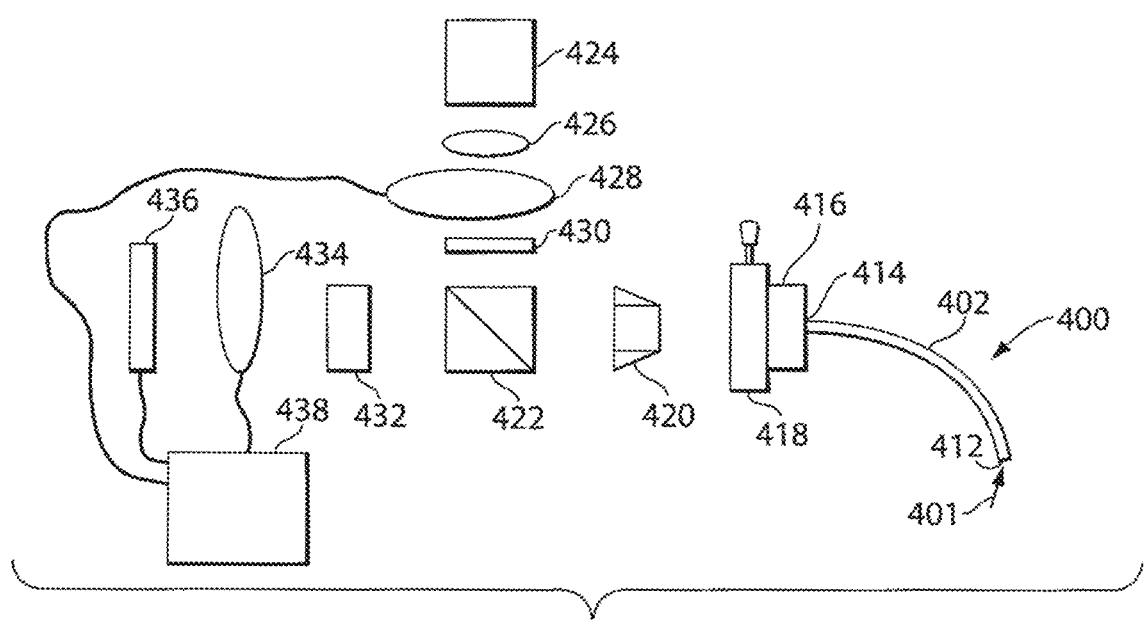
FIG. 11 is a schematic block diagram showing a system employing a fiber optic assembly with an optical detection system according to an embodiment of the invention.

For example, FIG. 11 shows a schematic block diagram of a system employing a fiber optic assembly 400 with an optical detection system. The fiber optic assembly 400 that comprises a fiber optic bundle or array 402 that is constructed from clad fibers so that light does not mix between fibers. An array of reaction vessels 401 is formed at/attached to the bundle's distal end 412, with the proximal end 414 being operatively connected with a z-translation stage 416 and x-y micropositioner 418. These two components act in concert to properly position the proximal end 414 of the bundle 402 for a microscope objective lens 420. Light collected by the objective lens 420 is passed to a reflected light fluorescence attachment with three pointer cube slider 422. The attachment 422 allows directs light from a 75 watt Xe lamp 424 through the objective lens 420 to be coupled into the fiber bundle 402. The light from source 424 is condensed by condensing lens 426, then filtered and/or shuttered by filter and shutter wheel 428, and subsequently passes through a ND filter slide 430. Light returning from the distal end 412 of the bundle 402 passes through the attachment 422 to a magnification changer 432 which enables adjustment of the image size of the fiber's proximal or distal end. Light passing through the magnification changer 432 is then shuttered and filtered by a second wheel 434. The light is collected by a charge coupled device (CCD) camera 436. A computer 438 executes imaging processing software to process the information from the CCD camera 436 and also optionally controls other components of the system, including but not limited to the first and second shutter and filter wheels 428, 434.

An array of reaction vessels used to practice some embodiments of the present invention may be integral with or attached to the distal end of the fiber optic bundle using a variety of compatible processes. In some cases, microwells are formed at the center of each individual fiber of the fiber optic bundle and the microwells may or may not be sealed. Each optical fiber of the fiber optic bundle may convey light from the single microwell formed at the center of the fiber's distal end. This feature enables the interrogation of the optical signature of individual reaction vessels to identify reactions/contents in each microwell. Consequently, by collecting the image of the end of the bundle with the CCD array, the optical signatures of the reaction vessels may be individually interrogated and/or imaged substantially simultaneously.

Quantification

According to some embodiments of the present invention, the methods, systems, and/or devices are used to determine the presence and/or a measure of the concentration of analyte molecules (or particles) in a fluid sample based at least in part on detecting and/or quantifying at least some of a plurality of capture objects used to capture the analyte molecules (and optionally at least one binding ligand). In certain embodiments where concentration is determined, a correlation and/or calibration relating the number (or fraction/percentage) of locations containing a capture object comprising at least one analyte molecule (and/or at least one binding ligand) to the quantity/concentration of analyte molecules in the fluid sample is employed. In some cases, the concentration of the analyte molecules in a fluid sample may be linearly proportional to the number/fraction of locations containing a capture object comprising at least one analyte molecule (and/or at least one binding ligand). In other cases, the measure of concentration of the analyte molecules in a fluid sample may be related to the number/fraction of locations containing a capture object associated with at least one analyte molecule (and/or at least one binding ligand) by a non-linear relationship. In some embodiments, a measure of the concentration of analyte molecules in a fluid sample may be determined at least in part using a calibration curve developed using samples containing known concentrations of target analyte molecules. Methods to determine a measure of the concentration of analyte molecules in a fluid sample are discussed more below.

Certain embodiments of present invention are distinguished by the ability to detect and/or quantify low numbers/concentrations of capture objects comprising at least one analyte molecule (and/or at least one binding ligand) and may be well suited to determine a measure of the concentration of analyte molecules in a fluid sample containing very low concentrations of the analyte molecule. This capability may be facilitated, in certain embodiments, at least in part by spatially isolating individual capture objects, including at least some comprising at least one analyte molecule (and/or at least one binding ligand), for example, by partitioning a plurality of such capture objects across an array of locations (e.g., reaction vessels), and then detecting their presence in the reaction vessels. The presence of a capture object comprising at least one analyte molecule (and/or at least one binding ligand) in a reaction vessel, in some embodiments, can be determined and the number of such reaction vessels counted in a binary fashion. That is, in embodiments where a location (e.g., a reaction vessel) is found to contain at least one capture object associated with at least one analyte molecule (and/or binding ligand), the location is counted as one. In embodiments where a location (e.g., a reaction vessel) is found to contain a capture object, the location is counted as zero. For example, wells that are counted as "ones" may be determined by detecting the presence of a detectable molecule or particle in a reaction vessel that, as described above, indicates the presence of a capture object comprising at least one analyte molecule (and/or at least one binding ligand) in the well.

In embodiments where a fluid sample containing or suspected of containing is contacted with a plurality of capture objects such that any analyte molecules present in the sample are immobilized with respect to the plurality of capture objects such that a statistically significant fraction (e.g., as described above) of the capture objects associate with a single analyte molecule and a statistically significant fraction of the capture objects do not associate with any analyte molecules (e.g., as shown in FIG. 1, step (B)), a determination of a measure of the concentration of analyte molecules in the fluid sample may be carried out as follows. First, at least a portion of the capture objects (at least some of which have a single analyte molecule immobilized) are spatially segregated into a plurality of locations (e.g., as shown in FIG. 1, step (C)). The number of locations that contain an analyte molecule immobilized with respect to a capture object is determined, either directly (e.g., by detection of the analyte molecule itself (e.g., see FIG. 1, step (D)) or indirectly (e.g., by detection of a binding ligand associated with the analyte molecule, by detection of a labeling agent (e.g., formed via conversion of a precursor labeling agent upon exposure to an analyte molecule see FIG. 4A), etc.). In some embodiments, a measure of the concentration of analyte molecules in a fluid sample is determined at least in part on the determination of the number of the plurality of locations that contain an analyte molecule (e.g., reaction vessels 12 in FIG. 1, step (D)). In certain such embodiments, a measure of the concentration of analyte molecules in the fluid sample is determined at least in part by comparison of this measured parameter to a calibration standard and/or by using a Poisson and/or Gaussian distribution analysis of the number of locations that would be expected to contain an analyte molecule.

In some embodiments the number of locations which comprise a capture object not associated with an analyte molecule may also be determined (e.g., reaction vessel 13 in FIG. 1, step (D)). In such cases, a measure of the concentration of analyte molecules in a fluid sample may be determined based at least in part on the ratio of locations comprising an analyte molecule immobilized with respect to a capture object, to the number of locations comprising a capture object not associated with an analyte molecule. In some cases, the number of locations which do not comprise a capture object may also be determined (e.g., reaction vessel 14 in FIG. 1, step (D)). In such cases, a measure of the concentration of analyte molecules in a fluid sample may be determined based at least in part on the ratio of locations comprising an analyte molecule immobilized with respect to a capture object to the number of locations not comprising a capture object and/or the number of locations not comprising an analyte molecule—whether or not such location contains a capture object (in either case above or elsewhere, the denominator for the ratio/fraction may or may not include the positive ("on" or "one") locations added to the nil ("off" or "zero") locations depending upon preference). In yet other cases, the total number of locations addressed/analyzed may be determined (e.g., reaction vessels 12, 13, and 14 in FIG. 1, step (D)) and a measure of the concentration of analyte molecules in a fluid sample may be based on the ratio of the locations comprising an analyte molecule immobilized with respect to a capture object to the total number of locations addressed/analyzed.

It should be understood, that in some assay methods, a measure of the concentration of analyte molecules in a fluid sample may be carried out using more than one type of analysis (e.g., a first analysis based on the number of locations comprising an analyte molecule immobilized with respect to a capture object, and a second analysis based on the ratio of the ratio/fraction of locations comprising an analyte molecule immobilized with respect to a capture component, to the total number of locations comprising a capture object, etc.). In such embodiments, the second analysis may be used as a quality control measure (e.g., to confirm that the first analysis provided a reasonable result) and/or the two analysis results may be averaged.

In some embodiments, the determination of a measure of the concentration of analyte molecules in a fluid sample being tested may be carried out using a similar analysis as described above, but by determining the number of reaction vessels which comprise a binding ligand as opposed to the number of reaction vessels which comprise an analyte molecule immobilized with respect to a capture object. As described herein, in some cases, following immobilization of a plurality of analyte molecules to a plurality of capture objects, the plurality of capture objects may be exposed to at least one type of binding ligand such that at least some of the immobilized analyte molecules associate with at least one binding ligand (e.g., see FIG. 2, step (B). This assay method may be especially useful in embodiments where more than one analyte molecule is expected to become associated with each capture object, but binary quantification may still be desired. In some cases, the binding ligand may be provided at a concentration such that at least some of the capture objects containing at least one analyte molecule do not associate with any binding ligands (e.g., see FIG. 2, step (C). In such embodiments, the number of locations containing a capture object associated with a binding ligand (e.g., via an analyte molecule) can replace the number of locations containing a capture object associated with an analyte molecule in the analysis and methods described above.

A measure of the concentration of analyte molecules or particles in a fluid sample may be determined using a variety of calibration techniques, and the particular technique resulting in the most accuracy and reliability can depend on the relative number/concentration of analyte molecules in the sample to the number/concentration of capture objects exposed to the sample (and or, for embodiments using binding ligands, the relative number/concentration of binding ligands to the number/concentration of capture objects exposed to each other during/after capture of the analyte molecules by the capture objects). Non-limiting examples of concentration determination methods that may be useful in particular analyte concentration regimes include the above described binary read-out methods, and/or methods in which the relative positive signal intensity measured for the locations ("intensity read-out methods") is employed. Either or both of the above methods—or alternative methods—may further employ a comparison of the measured parameter with a calibration curve.

It is currently believed that the most accurate method of determination may depend at least in part on the concentration of analyte molecules contained in the fluid sample. For example, in embodiments in which the concentration of the analyte molecules in the sample being tested results in a statistically significant fraction of locations to which that capture objects are partitioned comprising a single analyte molecule or binding ligand and a statistically significant fraction of locations not comprising any analyte molecules or binding ligands (e.g., at or approaching a regime where essentially no locations comprise more than one analyte molecule or binding ligand), a binary read-out method may be particularly useful, and in some cases, may be used in conjunction with a calibration curve. In other embodiments, where a larger number of locations comprise more than one analyte molecule and/or more than one binding ligand, a determination based at least in part on an intensity read-out may provide a more accurate measure of the concentration of analyte molecules in a fluid sample. Such a determination may also be used in conjunction with a calibration curve.

In certain embodiments, the fraction of locations (e.g., the statistically significant fraction) which comprises at least one capture object associated with an analyte molecule and/or binding ligand is less than about 50%, less than about 40%, less than about 25%, less than about 10%, less than about 5%, less than about 1%, less than about 0.5%, or less than about 0.1% of the total number of locations containing a capture object. In such embodiments, a measure of the concentration of analyte molecules in the fluid sample may be determined using a binary read-out method. In some cases, the percentage of locations which do not contain a capture object associated with an analyte molecule and/or binding ligand is at least about 20%, at least about 40%, at least about 50%, at least about 60%, at least about 70%, at least about 75%, at least about 80%, at least about 90%, or at least about 95%, at least about 99%, at least about 99.5%, at least about 99.9%, or greater, of the total number of locations.

While the discussion below focuses primarily on the use of a binary read-out system (e.g., based on counting the number of "on" and "off" locations) for ultra low level detection capability, this is by no means limiting, and the inventive methods and assays may also in certain embodiments employ instead of or in addition to a binary quantification protocol, one based in measurement of intensity (i.e. an intensity read-out method) (e.g., to extend dynamic range). As noted, in some cases, the detection systems and quantification methods may be configured so that the system can use either or both of a binary read-out determination and an intensity read-out determination, depending on the assay format and/or the concentration of analyte molecules in the fluid sample. For example, the method and/or system may be able to determine a base parameter from a first measurement and decide to use either a binary read-out determination or an intensity read-out determination depending on the result of the first determination, as described in more detail below and as is described in commonly owned U.S. patent application Ser. No. (not yet determined), entitled "Methods and systems for extending dynamic range in assays for the detection of molecules or particles" by Rissin et al., filed Mar. 24, 2010, Ser. No. 12/731,136 incorporated by reference.

According to one embodiment, the quantification method of the present invention can be performed as follows. A fluid sample containing or suspected of containing an analyte molecule of interest is contacted with a plurality of capture objects and, optionally, one or more binding ligands and the capture objects are partitioned across an array of locations, such as reaction vessels/wells (as described previously). In some embodiments, where a binary read-out method is desired to be used for determination, in the step of contacting the fluid sample with the capture objects, the relative amounts/concentrations of fluid sample and capture object containing solution are selected (e.g., based on a known or estimated/suspected approximate concentration range of analyte molecules in the sample) so that the ratio of analyte molecules in the fluid sample to total number of capture objects provided to the solution will be less than about 1:5, less than about 1:10, less than about 1:12, less than about 1:15, less than about 1:20, less than about 1:50, less than about 1:100, or less. With such ratios, at least some of the capture objects statistically will be expected associate with a single analyte molecule and the majority of the remainder of the capture objects will not associate with any analyte molecules. The number of capture objects associating with multiple analyte molecules under such conditions may be low enough to be neglected, such that capture object determined to comprise an analyte molecule can be assumed to comprise a single analyte molecule. Under such conditions, an analysis system configured to perform a binary read out quantification may be used to determine the number of locations which comprise a capture object associated with an analyte molecule by any detection method as described herein. The number of locations which comprise a capture object associated with an analyte molecule is then counted (e.g., FIG. 1, step (D), the total number of reaction vessels comprising an analyte molecules is two, e.g., reaction vessels 12) and, in some cases, the fraction of the total number of locations containing a capture object which contain a capture object associated with an analyte molecule is calculated (e.g., in FIG. 1, total number of reaction vessels comprising a capture object is three, reactions vessels 12 and 13; thus, fraction of the total number of locations comprising a capture object associated with an analyte molecule is 2:3). Utilization of a zero (no analyte molecule detected) or one (an analyte molecule detected) response, in conjunction with using an array with a large number of locations can permit a determination of bulk concentrations of analyte molecules in the sample by counting the actual number of molecules contained in the volume of sample partitioned across and contained in the locations. In some cases, the analyte molecule may be detected indirectly (e.g., the read-out is accomplished by counting the number of locations containing at least one labeling agent molecule, wherein the labeling agent has been converted from a precursor labeling agent upon exposure to an analyte molecule). In instances where a large number of locations (e.g., at least about 10,000 locations) are substantially simultaneously interrogated, the ratio of locations comprising an analyte molecule associated with a capture object to total number of locations determined (e.g., in some cases, the locations which contain a capture object associate with or not associated with any analyte molecules) may be at least about 1:100, at least about 1:1000, at least about 1:10,000 or less. Utilizing an array with a large number of locations (e.g., at least about 10,000, at least about 50,000, at least about 100,000, at least about 500,000, etc.) may provide a statistically significant signal even at this low ratio.

In some assays, a Poisson distribution adjustment may be applied to numbers and/or ratios determined by a binary read-out method to facilitate and/or improve accuracy of determining a concentration of analyte molecules in a fluid sample. For example, in embodiments where the ratio of analyte molecules in the fluid sample to the total number of capture objects contacted with the fluid sample is greater than about 1:10, greater than about 1:5, greater than about 1:4, greater than about 1:3, or greater than about 1:2, or between about 1:10 and about 1:2, between about 1:5 and about 1:2, the number of analyte molecules immobilized per capture may be zero or one, with a greater proportion containing more than one than for the regime described in the paragraph above. In some such cases, performance and accuracy of the concentration determinations may be improved over use of an assumption that all positive locations contain only a single analyte molecule (as described in the paragraph above) by employing a Poisson distribution adjustment to predict the number of locations expected to contain 0, 1, 2, 3, 4, etc., analyte molecules per capture object.

A Poisson distribution describes the likelihood of a number of events occurring if the average number of events is known. If the expected number of occurrences is $\mu$, then the probability ($P_\mu(v)$) that there are exactly $v$ occurrences ($v$ being a non-negative integer, $v=0, 1, 2, \ldots$) may be determined by Equation 5:

$$P_\mu(v) = e^{-\mu}\left(\frac{\mu^v}{v!}\right) \quad \text{(Eq. 5)}$$

In some embodiment of the present invention, $\mu$ is equal to the fraction of the number of locations determined to contain an analyte molecule associated with an analyte to the total number of capture objects detected (e.g., either associated with or not associated with any analyte molecules), and $v$ is the number of capture objects associated with a certain number of analyte molecules (e.g., the number of capture objects associated with either 0, 1, 2, 3, etc. analyte molecule). By determining $\mu$ from interrogating the array of locations during an assay, the concentration of analyte molecules in the sample can be determined using a Poisson distribution adjustment. For example, in an assay using the binary mode of measurements where capture objects associated with 1, 2, 3, 4, etc. analyte molecules are not distinguished from each other (e.g., where $v=1, 2, 3, 4$ are not differentiated from each other) and the wells (e.g., locations, reaction vessels) are simply characterized as "on" wells, then occurrences of $v=0$ can by determined definitively as the number of "off" wells. ($P_\mu(0)$) may be calculated according to Equation 6:

$$P_\mu(0) = e^{-\mu}\left(\frac{\mu^0}{0!}\right) = e^{-\mu} \quad \text{(Eq. 6)}$$

and the number of expected occurrences, $\mu$, may be determined based on a rearrangement of Equation 5, as given in Equation 7:

$$\mu = -\ln[P_\mu(0)] \quad \text{(Eq. 7)}.$$

The number of occurrences of capture objects associated with no analyte molecules (or binding ligands), $P_\mu(0)$, is equal to 1 minus the total number of capture objects with all other occurrences (e.g., capture objects associated at least one analyte molecule or binding ligand) then $\mu$ is given by Equation 8:

$$\mu = \frac{\text{Number of Analyte molecules}}{\text{Number of Capture objects}} = \quad \text{(Eq. 8)}$$
$$-\ln(1 - \text{fraction of "on" wells}).$$

Rearranging Equation 8, the total number of analyte molecules in the fluid sample contained in the locations interrogated containing a capture object can be determined using Equation (9):

Number of Analyte molecules=$-\ln(1-$fraction of "on" wells$)\times$Number of Capture objects (Eq. 9).

Therefore, the total number of molecules can be determined from the fraction of "on" wells for a given number of wells containing capture objects, and a measure of the concentration of analyte molecules in the fluid sample may be based at least in part on this number (as well as, e.g., any dilutions of the sample during the assay, the number and volume of the wells containing capture objects interrogated, etc.). The number of capture objects with 1, 2, 3, 4 etc. associated analyte molecules can also be determined by calculating $P_\mu(1)$, $P_\mu(2)$, $P_\mu(3)$ etc. from the $\mu$ determined and Equation 5.

As a non-limiting example of use of a Poisson distribution adjustment, in an assay where 26% of 50,000 capture objects interrogated were "on" (i.e., contained one or more analyte molecules and/or binding ligands) then the total number of analyte molecules present is calculated as $-\ln(1-0.26)\times 50,000=15,056$ molecules. Of these 15,056 molecules, using $\mu=-\ln(1-0.26)=0.3011$ in the Eq. 5 for $v=1$, 11,141 capture objects are calculated to have 1 analyte molecule, 1,677 capture objects 2 analyte molecules, 168 capture objects 3 analyte molecules, 13 capture objects 4 analyte molecules, and 1 capture object 5 analyte molecules. A similar analysis may be applied to embodiments where a statistically significant fraction of the spatially separated capture objects are associated with at least one binding ligand and a statistically significant fraction of spatially separated capture objects are not associated with any binding ligands.

In some embodiments, wherein the ratio of locations comprising a capture object associated with at least one analyte molecule and/or a binding ligand to locations containing a capture object free of any analyte molecule/binding ligand is high (e.g., greater than about 1:2, greater than about 1:1, greater than about 2:1, greater than about 4:1, greater than about 8:1, or greater), the determination of the concentration of analyte molecules in the fluid sample may be based at least in part on an intensity read-out determination. In such an embodiment, the total intensity of the array (e.g., total fluorescence) may be determined and a measure of the concentration of analyte molecules in the fluid sample is based at least in part on this determination.

In some embodiments, a measure of the concentration of analyte molecules or particles in the fluid sample may be determined at least in part by comparison of a measured parameter to a calibration standard. In some cases, a calibration curve may be used, similar to as described herein, wherein the total intensity is determined for a plurality of samples comprising the analyte molecule at a known concentration using a substantially similar assay format. For example, the number and/or fraction of locations that comprise a capture object associated with an analyte molecule (e.g., based on a binary read-out), or alternatively, the total intensity of the array, may be compared to a calibration curve to determine a measure of the concentration of the analyte molecule in the fluid sample. The calibration curve may be produced by completing the assay with a plurality of standardized samples of known concentration under similar conditions used to analyze test samples with unknown concentrations. A calibration curve may relate the fraction of the capture objects determined to be associated with an analyte molecule and/or binding ligand with a known concentration of the analyte molecule. The assay may then be completed on a sample containing the analyte molecule in an unknown concentration, and number/fraction of capture objects determined to be associated with an analyte molecule and/or binding ligand may be compared to the calibration curve, (or a mathematical equation fitting same) to determine a measure of the concentration of the analyte molecule in the fluid sample.

Figure 12:
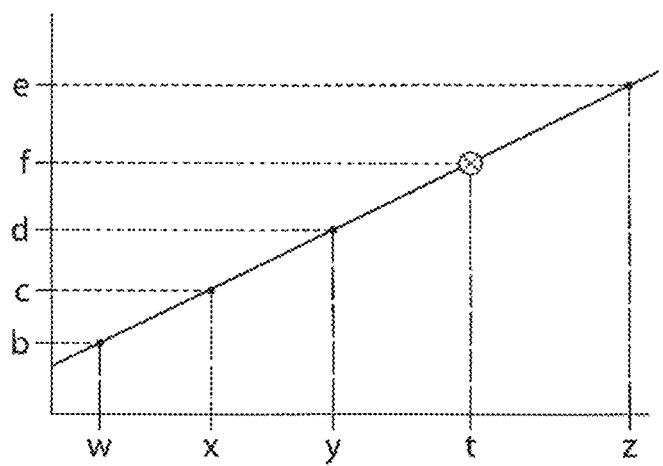
FIG. 12 shows a graph of a schematic calibration curve that may be used to determine the concentration of analyte molecules or particles in a fluid sample, according to some embodiments of the present invention.

In one exemplary embodiment for performing a calibration, four standardized fluid samples comprising an analyte molecule in varying concentration (w, x, y, and z) are used. An assay (e.g., immobilizing the analyte molecules with respect to a plurality of capture objects, optionally exposing the capture objects to at least one type of binding ligand, partitioning at least a portion of the capture objects into a plurality of discrete, separately addressable locations, detecting at least a portion of the capture objects, etc.) is carried out for each calibration sample, and the number/fraction of capture objects comprising an analyte molecule and/or binding ligand (b, c, d, and e) is determined. A plot/equation/look-up table, etc. is produced relating the values b, c, d, and e to concentrations w, x, y, and z, respectively, as depicted in FIG. 12. The assay may be then be carried out under substantially identical conditions on a fluid sample containing an analyte molecule of unknown concentration, wherein the resulting value of number/fraction of capture objects comprising an analyte molecule and/or binding ligand determined to detection of the capture objects is f. This value (f) may be plotted on the graph and a measure of the unknown concentration of the target analyte in the fluid sample (t) may be determined. In some cases, the calibration curve may have a limit of detection, wherein the limit of detection is the lowest concentration of analyte molecules in a fluid sample that may be accurately determined. In some cases, the $r^2$ value of the calibration curve may be greater than about 0.5, greater than about 0.75, greater than about 0.8, greater than about 0.9, greater than about 0.95, greater than about 0.97, greater than about 0.98, greater than about 0.99, greater than about 0.9999, or about 1. Values b, c, d, and e may be based on the absolute number of measured locations/capture objects associated with an analyte molecule (or binding ligand), or a ratio of the number of locations containing a capture object associated with an analyte molecule (or binding ligand) to the number of locations containing a capture object not associated with any analyte molecules or a ratio of the number of locations containing a capture object associated with an analyte molecule (or binding ligand) to the number of locations containing a capture object or a ratio of the number of locations containing a capture object associated with an analyte molecule (or binding ligand) to the total number of locations addressed, etc. Any number of calibration standards may be used to develop the calibration curve (e.g., about 2, 3, 4, 5, 6, 7, 8, 9, 10, or more, calibration standards).

In some embodiments, the concentration of analyte molecules in the fluid sample may be determined through use of a calibration curve using an assay system employing a computer. The computer may execute software that may use the data collected to produce the calibration curve and/or to determine a measure of the concentration of analyte molecules in a test fluid sample from such calibration curve. For example, a fluorescence image of an array comprising the plurality of capture objects partitioned across the array may be collected and analyzed using image analysis software (e.g., IP Lab, BD Biosciences). The analysis software may automatically calculate the number of locations that have fluorescence intensity over the background intensity (e.g., a number that correlates to the number of locations which comprise an analyte molecule). The number of locations which comprise fluorescence intensity over the background intensity may be divided by the total number of locations addressed, for example, to determine the fraction of locations which comprise an analyte molecule. The active location fraction may be compared to a calibration curve to determine a measure of the concentration of analyte molecules in the fluid sample.

In certain embodiments, it may be possible to increase both the dynamic range and the sensitivity of the assay by expanding the number of locations into which the capture objects are partitioned and/or by adjusting the ratio of capture objects (e.g. beads) to analyte molecules in the initial capture step. In certain cases, decreasing or increasing the analyte-to-bead ratio may result in more dynamic range. In some cases, as the volume of a sample increases, detecting small numbers of analyte molecule with accuracy, may, in some cases, become more challenging for example, due to limitations of equipment, time constraints, etc. For example, to achieve the same efficiencies in larger volume sample (e.g., 1 mL, 10 mL) as achieved with a smaller volume sample (e.g., 100 µL), more beads (e.g., 10 and 100 times more beads, respectively) may be necessary, and thus, the beads may need to be spatially segregated into larger number of locations, wherein the larger number of locations may require an increased imaging area.

For the capture step, the choice of bead concentration may depend on several competing factors. For example, it can be advantageous if sufficient beads are present to capture most of the target analyte from thermodynamic and kinetic perspectives. As an exemplary illustration, thermodynamically, 200,000 beads in 100 µL that each have about 80,000 capture components (e.g. antibodies) bound to correlates to an antibody concentration of about 0.3 nM, and the antibody-protein equilibrium at that concentration may give rise to a relatively high capture efficiency of target analyte molecules in certain cases (e.g. >70%). Kinetically, for 200,000 beads dispersed in 100 µL, the average distance between beads can be estimated to be about 80 µm. Proteins the size of TNF-α and PSA (17.3 and 30 kDa, respectively), as exemplary analyte molecules, for example, will typically tend to diffuse 80 µm in less than 1 min, such that, over a 2 hour incubation, capture of such analyte molecules will tend not to be limited kinetically. In addition, it can also be advantageous to provide sufficient beads loaded onto the arrays to limit Poisson noise to a desired or acceptable amount. Considering as an example a situation where 200,000 beads in a in 10 µL volume are loaded onto an array, typically about 20,000-30,000 beads may become trapped in femtoliter sized wells of the array. For a typical background signal (e.g. due to non specific binding, etc.) of 1% active beads, this loading would be expected to result in a background signal of 200-300 active beads detected, corresponding to a coefficient of variation (CV) from Poisson noise of 6-7%, which may be acceptable in typical embodiments. However, bead concentrations above certain concentrations may be undesirable in certain cases in that they may lead to: a) increases in non-specific binding that may reduce signal-to-background; and/or b) undesirably low ratios of analyte-to-bead such that the fraction of active beads is too low, resulting in high CVs from Poisson noise. In certain embodiments, considering a balance of factors such as those discussed above, providing about 200,000 to 1,000,000 beads per 100 µL of test sample may be desirable or, in certain cases optimal, for performing certain assays of the invention.

For embodiments of the inventive assay employing one or more binding ligand(s) to label the captured analyte molecules, it may be advantageous to, in certain instances, adjust the concentrations used to yield desirable or optimal performance. For example, considering an embodiment involving an analyte molecule that is a protein (captured protein) and employing a first binding ligand comprising a detection antibody and a second binding ligand comprising an enzyme conjugate (e.g. SβG), the concentrations of detection antibody and enzyme conjugate (SβG) used to label the captured protein may in some cases be limited or minimized to yield an acceptable background signal (e.g. 1% or less) and Poisson noise. The choice of the concentrations of detection antibody and enzyme conjugate (SβG) used to label the captured protein can be factors in improving the performance of or optimizing certain of the inventive assay methods. In certain cases, it may be desirable for only a fraction of the capture proteins to be labeled so as to avoid saturating signals produced by the assay. For example, for a particular assay where background levels observed are equivalent to ~1-2 fM of target protein, such that the ratio of analyte to bead may be about 0.3-0.6, the number of active beads may be in the range of about 25-40% if every protein was labeled with an enzyme, which may be higher than desirable in some cases. To produce background signals that may be closer to a lower end of the dynamic range for a digital detection assay—considering e.g. that in certain cases 1% active beads may provide a reasonable noise floor for background in digital detection assays of the invention—appropriate labeling of the captured protein can potentially be achieved by kinetic control of the labeling steps, either by limiting or minimizing the concentrations of both labeling reagents or by using shorter incubation times. For example, in an embodiment where label concentrations are minimized, use of a standard ELISA incubation time may provide acceptable results; e.g. using a total assay time of ~6 h. This length of time may be acceptable for testing that tolerates a daily turnaround time for samples. For shorter turnaround times of, for example, <1 hour (e.g., for point-of-care applications), the assay could be performed with shorter incubations with higher concentrations of labels.

In some embodiments, accuracy of a particular method of determining concentration with the inventive assays may be compromised, i.e. both above and below the thresholds of the dynamic range for the particular method. For example, as the concentration of the capture objects associated with an analyte molecule goes down, eventually, when below the lower limit of the dynamic range, the number of capture objects associated an analyte molecule may be too low to observe a sufficient number of occupied locations to obtain a reliable and reproducible measurement. In such a situation, the number of locations could be decreased in order to make sure that at least some (e.g., a statistically significant number) of them are occupied by a capture object associated with an analyte molecule, and/or the sample tested could be concentrated and/or the number of capture objects incubated with the sample could be decreased, etc. to increase the number/fraction of positive capture objects detected. On the other hand, a binary read-out system/method may be above its upper threshold of accuracy and/or utility when, for example, loading approaches saturation with "on" capture objects such that substantially 100% of the locations contain at least one capture object associated with an analyte molecule. At this limit, discrimination between two samples with concentrations falling in this range may not be feasible using a binary read-out system/method. In such a situation, to provide a more accurate result, a greater number of locations could be used, the concentration of the sample could be reduced, for example, through serial dilutions, the number of capture objects incubated with the sample could be increased, etc. to decrease the number/fraction of positive capture objects detected, and/or an intensity read-out system/method could be employed.

In some embodiments, the concentration of analyte molecules or particles in the fluid sample that may be substantially accurately determined is less than about 5000 fM, less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. In some cases, the limit of detection (e.g., the lowest concentration of an analyte molecule which may be determined in solution substantially accurately) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte molecules or particles in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM. The concentration of analyte molecules or particles in a fluid sample may be considered to be substantially accurately determined if the measured concentration of the analyte molecules or particles in the fluid sample is within about 10% of the actual (e.g., true) concentration of the analyte molecules or particles in the fluid sample. In certain embodiments, the measured concentration of the analyte molecules or particles in the fluid sample may be within about 5%, within about 4%, within about 3%, within about 2%, within about 1%, within about 0.5%, within about 0.4%, within about 0.3%, within about 0.2% or within about 0.1%, of the actual concentration of the analyte molecules or particles in the fluid sample. In some cases, the measure of the concentration determined differs from the true (e.g., actual) concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some embodiments, by determining the concentration of analyte molecules in a fluid sample of a known concentration using the selected assay method.

In some embodiments, more than one of the above described types of analysis and quantification methods may be employed with the same system and in a single assay. For example, in embodiments where the analyte molecules are present at lower concentration ranges, single analyte molecules can be detected, and the data may be analyzed using a digital analysis method (binary quantification). In some cases using binary quantification, as previously described, the data may be processed using a Poisson distribution adjustment. At higher concentration ranges (e.g., where it may become challenging or inaccurate to perform binary quantification), the data may be analyzed using an analog analysis method, based, for example on measured relative signal intensities (intensity read-out determination). In certain embodiments, the results of the two analysis methods (digital and analog) may both be utilized by a single assay system/protocol of the invention by linking the two methods using a single calibration curve. For example, in some embodiments, at low concentration levels (e.g., in the digital/binary concentration range), a measure of the concentration of analyte molecules in a fluid sample may be determined at least in part by counting beads as either "on" (e.g., by determining if the reaction vessel contains a bead associated with an analyte molecule) or "off" (e.g., by determining if the reaction vessel contains a bead not associated with any analyte molecule). At low ratios of analyte molecules to beads (e.g., less than about 1:5, less than about 1:10, less than about 1:20, etc.), substantially all of the beads are associated with either zero or a single analyte molecule. In this range, the percentage of active beads (e.g., "on" reaction vessels) increases linearly with increasing analyte concentration, and a digital analysis method may be most suitable.

As the analyte concentration increases, however, more of the beads will associate with more than one analyte molecule. Therefore, as the analyte concentration increases (but still in the digital range), the percentage of active beads in a population generally will not be linearly related to the bulk analyte concentration as some of the beads may associate with more than one analyte molecule. In these concentration ranges, the data may be advantageously analyzed using a digital analysis method with the above described Poisson distribution adjustment. The above described non-linear effect can be accounted for using Poisson distribution adjustment across substantially the concentration range in which there remains a statistically significant fraction of beads not associated with any analyte molecules or particles in the sample. For example, ranges of percentage of active beads (i.e. "on" beads divided by total beads multiplied by 100%) for which a digital analysis method may be able to accurately determine a measure of the concentration, include up to about 20% active beads, up to about 30% active beads, up to about 35% active beads, up to about 40% active beads, up to about 45% active beads, up to about 50% active beads, or more. In many cases when operating in the ranges above, using a Poisson distribution adjustment will improve accuracy.

Above a certain active bead percentage (i.e., where there is no longer a statistically significant fraction of beads present in the population that are not associated with any of analyte molecules or particles, or, potentially advantageously for situations where there may be a statistically significant fraction of beads present in the population that are not associated with any of analyte molecules or particles but that result in active bead percentages above a certain level—e.g., greater than or substantially greater than about 40%) (or active location percentage, in embodiments where beads are not employed)) improvements in accuracy and/or reliability in the determination of analyte molecule concentration may potentially be realized by employing an intensity measurement based analog determination and analysis rather than or supplementary to a digital/binary counting/Poisson distribution adjustment as previously described. At higher active bead percentages, the probability of an active bead (e.g., positive reaction vessel) being surrounded by other active beads (e.g., positive reaction vessels) is higher and may in certain assay set ups create certain practical challenges to exclusively using the digital/binary determination method. For example, in certain embodiments, leakage of a detectable component into a reaction vessel from an adjacent reaction vessel may occur to some extent. Use of an analog, intensity level based technique in such situations can potentially yield more favorable performance. In an intensity measurement based analog determination and analysis, the association of multiple analyte molecules at relatively high concentrations with single beads is quantified. The intensity of at least one signal from the plurality of reaction vessels which contain at least one analyte molecule may be determined. In some cases, the intensity is determined as the total overall intensity for the reaction vessels containing at least one analyte molecule (e.g., the intensity of the reaction vessels in determined as a whole). In other cases, the intensity of each reaction vessel with a signal may be determined and averaged, giving rise to an average bead signal (ABS).

According to certain embodiments, an inventive assay system may include a link between the results/parameters of the two analysis methods/systems (i.e. digital and analog), for example, with the aid of a calibration curve, so that the system is able to operate in multiple modes of quantification depending on the signal relating to the number/fraction of "on" beads detected. Such systems can have substantially expanded dynamic ranges in certain cases. Further description of such systems which can combine and use more than one quantification method for a single assay is provided in commonly owned U.S. patent application Ser. No. (not yet determined), entitled "Methods and systems for extending dynamic range in assays for the detection of molecules or particles" by Rissin et al., filed Mar. 24, 2010, Ser. No. 12/731,136 incorporated by reference.

The following examples are included to demonstrate various features of the invention. Those of ordinary skill in the art should, in light of the present disclosure, will appreciate that many changes can be made in the specific embodiments which are disclosed while still obtaining a like or similar result without departing from the scope of the invention as defined by the appended claims. Accordingly, the following examples are intended only to illustrate certain features of the present invention, but do not necessarily exemplify the full scope of the invention.

Example 1

This following example describes materials used in Examples 2-19. Optical fiber bundles were purchased from Schott North America (Southbridge, Mass.). Non-reinforced gloss silicone sheeting was obtained from Specialty Manufacturing (Saginaw, Mich.). Hydrochloric acid, anhydrous ethanol, and molecular biology grade Tween-20 were purchased from Sigma-Aldrich (Saint Louis, Mo.). 2.8-um (micrometer)-diameter tosyl-activated magnetic beads were purchased from Invitrogen (Carlsbad, Calif.). 2.7-um-diameter carboxy-terminated magnetic beads were purchased from Varian, Inc. (Lake Forest, Calif.). Monoclonal anti-human TNF-α capture antibody, polyclonal anti-human TNF-α detection antibody, and recombinant human TNF-α were purchased from R&D systems (Minneapolis, Minn.). Monoclonal anti-PSA capture antibody and monoclonal detection antibody were purchased from BiosPacific (Emeryville, Calif.); the detection antibody was biotinylated using standard methods. 1-ethyl-3-(3-dimethylaminopropyl) carbodiimide hydrochloride (EDC), N-hydroxysulfosuccinimide (NHS), and SuperBlock® T-20 Blocking Buffer were purchased from Thermo Scientific (Rockford, Ill.). DNA was purchased from Integrated DNA Technologies (Coralville, Iowa) and/or purified DNA was ordered from Integrated DNA Technologies (Coralville, Iowa). Streptavidin-β-galactosidase (SβG) was purchased from Invitrogen or conjugated in house using standard protocols. Resorufin-β-D-galactopyranoside (RGP) was purchased from Invitrogen (Carlsbad, Calif.). The fiber polisher and polishing consumables were purchased from Allied High Tech Products (Rancho Dominguez, Calif.).

Example 2

The following describes a non-limiting example of the preparation of 2.8-um-diameter magnetic beads functionalized with protein capture antibody. 600 uL (microliter) of 2.8-um-diameter tosyl-activated magnetic bead stock (1.2× $10^9$ beads) was washed three times in 0.1 M sodium borate coating buffer pH 9.5. 1000 ug (microgram) of capture antibody was dissolved in 600 uL of sodium borate coating buffer. 300 uL of 3M ammonium sulfate was added to the antibody solution. The 600 uL of bead solution was pelleted using a magnetic separator and the supernatant was removed. The antibody solution was added to the beads and the solution was allowed to mix at 37° C. for 24 hours. After incubation, the supernatant was removed and 1000 uL of PBS buffer containing 0.5% bovine serum and 0.05% Tween-20 was added to the beads. The beads were blocked overnight (~8 hours) at 37° C. The functionalized and blocked beads were washed three times with 1 ml PBS buffer containing 0.1% bovine serum and 0.05% Tween-20. Finally, 1 mL of PBS containing 0.1% bovine serum, 0.05% Tween-20, and 0.02% sodium azide was added to the functionalized and blocked beads. 50 uL aliquots were stored at 4° C. for later use.

Example 3

The following describes a non-limiting example of the preparation of 2.7-um-diameter magnetic beads functionalized with protein capture antibody. 500 uL of 2.7-um-diameter carboxy-terminated magnetic beads stock (1.15× $10^9$ beads) was washed twice in 0.01 M sodium hydroxide, followed by three washes in deionized water. Following the final wash, the bead solution was pelleted and the wash solution was removed. 500 uL of a freshly prepared 50 mg/mL solution of NHS in 25 mM MES, pH 6.0, was added to the bead pellet and mixed. Immediately, a 500 uL of a freshly prepared 50 mg/mL solution of EDC in 25 mM MES, pH 6.0, was added to the bead solution and mixed. The solution was then allowed to mix for 30 min at room temperature. After activation, the beads were washed twice with 25 mM MES at pH 5.0. Meanwhile, 1000 uL of 25 mM MES at pH 5.0 was used to dissolve 1000 ug of capture antibody. The antibody solution was then added to the activated beads and the coupling reaction was allowed to proceed for 3 hours at room temperature. After incubation, the supernatant was removed using the magnetic separator, and 1000 uL of 100 mM Tris-HCl (pH 7.4) was added and allowed to mix at room temperature for one hour to block any remaining reactive sites. Finally, the functionalized beads were stored in 1 mL of SuperBlock blocking buffer, and 0.02% sodium azide was added to the functionalized and blocked beads. 50 uL aliquots were stored at 4° C. for later use.

Example 4

The following describes a non-limiting example of the preparation of 2.7-um-diameter magnetic beads functionalized with DNA. 120 μL of 2.7-um-diameter carboxy-terminated magnetic beads was washed three times with 0.01 M NaOH, followed by deionized water for another three times. 500 uL of freshly prepared 50 mg/mL NHS in cold 25 mM MES (pH 6) was added to the pellet of beads after the final wash, and the beads were re-suspended by vortexing briefly. 500 uL of freshly prepared 50 mg/mL EDC solution in cold 25 mM MES (pH 6) was immediately added to this bead suspension and mixed for 30 min. After activation, the beads were washed three times with cold 25 mM MES (pH 5). DNA capture probe with amine modification at 5' end (5'-NH2/C12-GTT GTC AAG ATG CTA CCG TTC AGA G-3' (SEQ ID NO. 1)) was dissolved in nuclease-free water to make a 2.6 mM stock solution. 60 μL of the DNA stock was added to 600 uL of the coupling buffer that contains 0.1 M sodium phosphate and 0.5 M NaCl, pH 8. The resulting DNA solution was added to the washed beads and mixed for 3 hours at room temperature. The bead suspension was vortexed every 30 min during the reaction. After incubation, the DNA supernatant was removed and 1 mL of 100 mM Tris-HCL (pH 7.4) was added to the pellet and mixed for 1 hour to inactivate the remaining binding sites on the beads. Finally, the beads were washed in Tris-EDTA (TE) buffer and 0.05% Tween-20 for three times, and stored in TE buffer containing 0.05% Tween-20 and 0.02% sodium azide at 4° C.

Example 5

The following describes a non-limiting example of the capture of proteins on magnetic beads and formation of enzyme-labeled immunocomplex. Test solutions containing the protein of interest were incubated with suspensions of magnetic beads functionalized with capture antibody (e.g., see Example 2) for 1 h at 37° C. The beads were then separated and washed three times in PBS. The beads were resuspended and incubated with solutions containing detection antibodies for 30 min at 37° C. The beads were then separated and washed three times in PBS. The beads were incubated with solutions containing SβG (e.g., target analyte) for 30 min at 37° C., separated, and washed six times in PBS and 0.1% Tween-20. The beads were then resuspended in 10 uL of PBS in order to load into the wells of the fiber bundle arrays.

Example 6

The following describes a non-limiting example of the capture of DNA on magnetic beads and formation of enzyme-labeled complex (FIG. 25). Beads functionalized with DNA capture probe (e.g., see Example 4) that is specific to the complementary target DNA of interest were incubated with solutions containing the target DNA (5'-TT GAC GGC GAA GAC CTG GAT GTA TTG CTC C TCT GAA CGG TAG CAT CTT GAC AAC-3' (SEQ ID NO. 2)) (e.g., target analyte) for 2 hrs. After incubation, the DNA target solution was removed and the beads were washed three times in 0.2×SSC buffer containing 0.1% Tween-20. The beads were then resuspended and mixed with 10 nM biotinylated signal probe (5'-TAC ATC CAG GTC TTC GCC GTC AA/Biotin/-3' (SEQ ID NO. 3)) (e.g., first type of binding ligand) that is also specific to the target DNA for 1 hr. The beads were then washed three times in 0.2×SSC buffer containing 0.1% Tween-20 after removing the signal probe. A solution 10 pM containing SβG (e.g., second type of binding ligand comprising an enzymatic component) was then added to the bead pellet, resuspended, and mixed for 1 hr. The beads were then separated and washed six times in 5×PBS buffer containing 0.1% Tween-20. The beads were then resuspended in 10 μL of PBS and loaded onto a femtoliter well array.

Example 7

Figure 24:
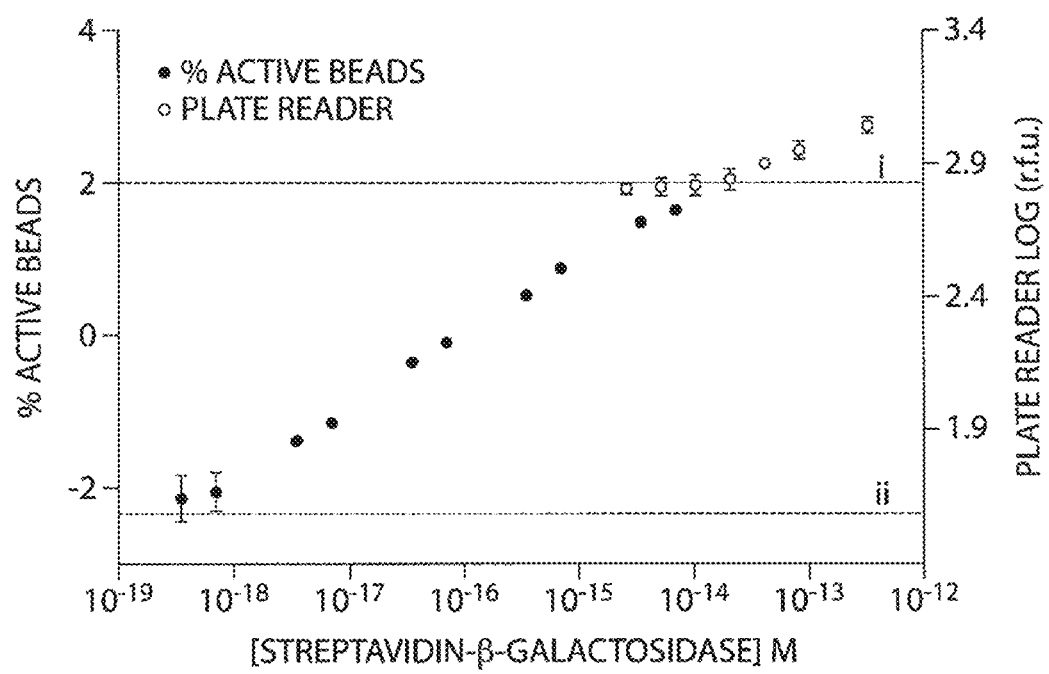
FIG. 24 shows a plot of the log of the fraction of capture objects determined to be associated with an analyte molecule versus the log of the concentration of analyte molecules in a fluid sample, according to an exemplary embodiment.

The following example describes the capture of biotin-labeled DNA on magnetic beads and formation of enzyme-labeled complex, according to a non-limiting embodiment (see FIG. 24). Beads functionalized with DNA capture probe that is specific to DNA of interest were incubated with 1 uM target DNA-biotin (5'-biotin-C TCT GAA CGG TAG CAT CTT GAC AAC-3' (SEQ ID NO. 4)) overnight (16 hrs) in TE buffer containing 0.5M NaCl and 0.01% Tween-20. After incubation, the DNA target solution was removed and the beads were washed three times in PBS buffer containing 0.1% Tween-20. The bead stock was distributed into a microtiter plate giving 400,000 beads per well in 100 uL. The buffer was aspirated from the microtiter plate wells, the beads were resuspended and incubated with various concentrations of SβG in Superblock containing 0.05% Tween-20 for 5 hr. In some cases, the beads were resuspended every 30 min during the incubation. The beads were then separated and washed six times with 5×PBS buffer containing 0.1% Tween-20. Finally, the beads were resuspended in 10 uL of PBS containing 0.1% Tween-20. In some embodiments, the beads were then separated and washed six times with 5×PBS buffer containing 0.1% Tween-20. For detection of enzyme, the beads were either: a) resuspended in 20 μL of PBS containing 0.1% Tween-20, and 10 μL aliquots were loaded onto two femtoliter well arrays for detection, or; b) resuspended in 100 μL of 100 μM RGP in PBS, incubated for 1 h at room temperature, and read on a fluorescence plate reader (Infinite M200, Tecan).

Example 8

The following describes a non-limiting example of the preparation of microwells arrays. Optical fiber bundles approximately 5-cm long were sequentially polished on a polishing machine using 30-, 9-, and 1-micron-sized diamond lapping films. The polished fiber bundles were chemically etched in a 0.025 M HCl solution for 130 seconds, and then immediately submerged into water to quench the reaction. To remove impurities from etching, the etched fibers were sonicated for 5 s and washed in water for 5 min. The fibers were then dried under vacuum and exposed to air plasma for 5 min to clean and activate the glass surface. The arrays were silanized for 30 minutes in a 2% solution of silane to make the surfaces hydrophobic.

Example 9

The following describes a non-limiting example of the loading of beads into microwells. To apply the solution of beads to the etched wells in a fiber bundle, clear PVC tubing (1/16" I.D. 1/8" O.D.) and clear heat shrink (3/16" ID) were cut into approximately 1 cm long. A piece of PVC tubing was first put onto the etched and functionalized end of a fiber bundle to create a reservoir to hold the bead solution, followed by the application of heat shrink around the interface between the PVC tubing and fiber bundle to provide a tight seal. 10 uL of the concentrated bead solution was pipetted into the reservoir created by the PVC tubing. The fiber bundle was then centrifuged at 3000 rpm (1333 g) for 10 minutes to force the beads into the etched wells. The PVC tubing/heat shrink assembly was removed after centrifugation. The distal end of the fiber bundle was dipped in PBS solution to wash off excess bead solution, followed by swabbing the surface with deionized water.

Example 10

The following describes a non-limiting example of the detection of beads and enzyme-labeled beads in microwell arrays. A custom-built imaging system containing a mercury light source, filter cubes, objectives, and a CCD camera was used for acquiring fluorescence images. Fiber bundle arrays were mounted on the microscope stage using a custom fixture. A droplet of β-galactosidase substrate (RPG) was placed on the silicone gasket material, and put into contact with the distal end of the fiber array. The precision mechanical platform moved the silicone sheet into contact with the distal end of the etched optical fiber array, creating an array of isolated femtoliter reaction vessels. Fluorescence images were acquired at 577 nm with an exposure time 1011 ms. Five frames (at 30 seconds per frame) were taken for each fiber bundle array. The fluorescent images were analyzed using image analysis software to determine the presence or absence of enzymatic activity within each well of the microwell array. The data was analyzed using a developed image processing software using MathWorks MATLAB and MathWorks Image Processing toolbox. The software aligns acquired image frames, identifies reaction vessel positions, locates reaction vessels with beads and measures the change in reaction vessel intensity over a predefined time period. Reaction vessels containing beads with sufficient intensity growth over all data frames are counted and the final number of active reaction vessels is reported as a percentage of all identified reaction vessels.

As well as fluorescence, the arrays were imaged with white light to identify those wells that contain beads. After acquiring the fluorescence images, the distal (sealed) end of the fiber bundle arrays were illuminated with white light and imaged on the CCD camera. Due to scattering of light by the beads, those wells that contained a bead appeared brighter in the image than wells without beads. Beaded wells were identified using this method by software.

Example 11

Figure 13:
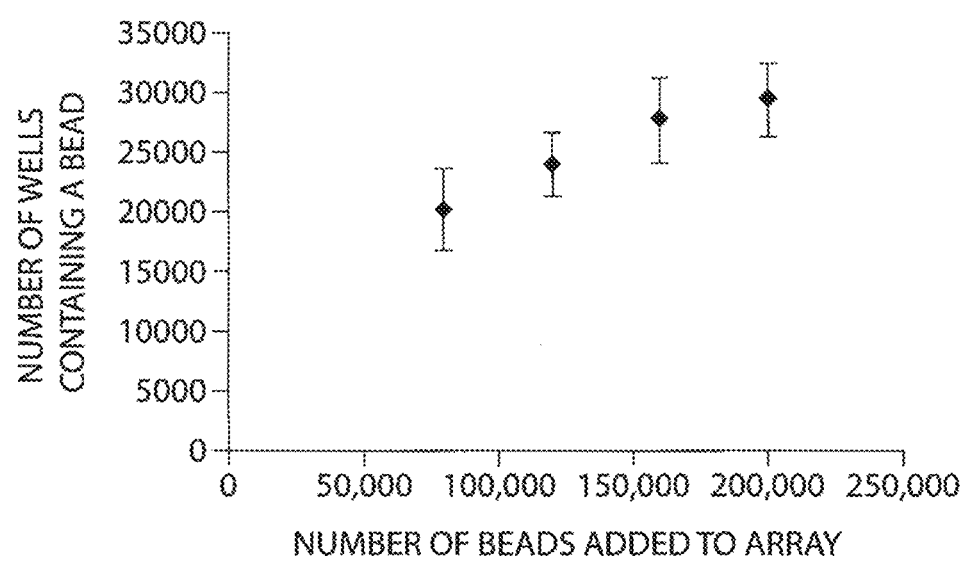
FIG. 13 shows a graph of the number of reaction vessels comprising a bead versus the total number of beads provided to the reaction vessels, according to a non-limiting embodiment.

The following describes a non-limiting example of the loading of beads into an array of microwells (FIG. 13). Arrays of 50,000 microwells were prepared as described above. 2.8 um beads were prepared as described above. 10-uL solutions containing different numbers of beads (from 80,000 to 2 million beads) were prepared as described above. Beads were loaded into the arrays of microwells as described above. The array loaded with a solution comprising 2 million beads was imaged using scanning electron microscopy (SEM). SEM showed that >99% of the 50,000 wells contained a bead, and each of these well only contained a single bead. The arrays loaded with 80,000 to 200,000 beads were imaged using white-light microscopy and image analysis was used to identify wells that contained a bead. The number of beads per array was determined over three arrays and plotted as a function of number of beads in solution (FIG. 13B). From FIG. 13B, in this embodiment, the number of beads loaded is a fraction of those provided in solution and not every well contains a bead at these assay-relevant bead loading concentrations. In some cases, the presence of a bead in a well (using white light images) may be correlated to those wells that contain enzymatic activity. In such cases, the read-out may be ratiometric (% active beads) and normalized for variation in bead loading.

Example 12

Figure 14A:
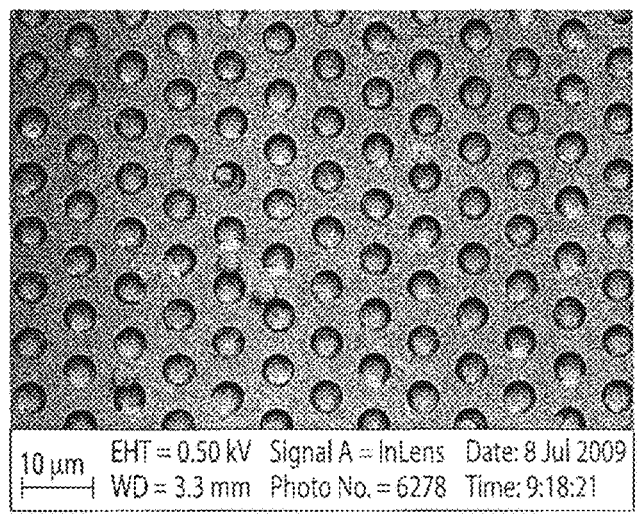
FIGS. 14A-14C show non-limiting images of beads contained in arrays comprising a plurality of reaction vessels.
Figure 14B:
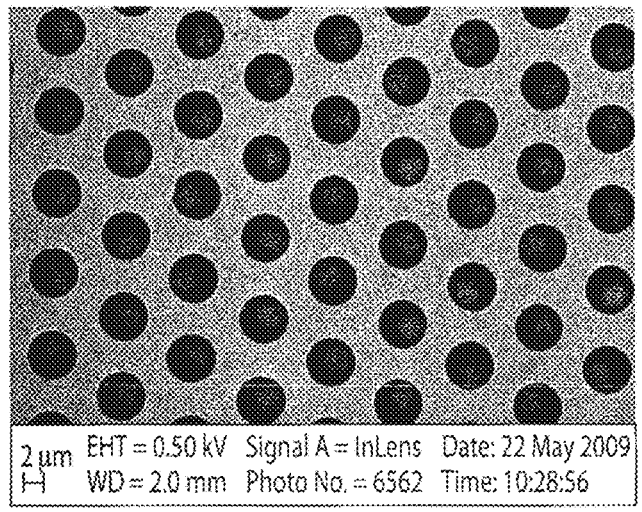
Figure 14C:
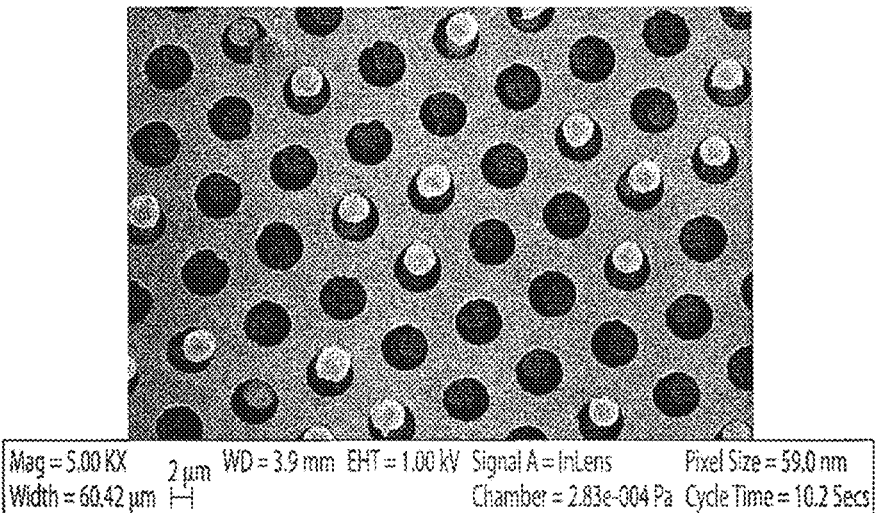

The following describes a non-limiting example of bead filling as a function of well depth (FIG. 14). In some embodiments, a single bead containing single analyte molecules can be delivered into a microwell so that they can be spatially isolated and sealed. To achieve this situation, the well depth and width may be carefully controlled to parameters optimized for a given bead diameter. FIGS. 14A-14C show SEM images of beads loaded as described above into arrays of microwells where the well depth was controlled by etching for different times. On average, the wells etch at a rate of approximately 1.5 to 1.7 µm per minute. Therefore, wells of 3.25 um depth are produced in about 115 to 130 s. For a well depth of 2.5 urn (FIG. 14A), very few beads are retained in the microwells as they are too shallow and detection of single analytes may be poor. At 3-um depth (FIG. 14B), SEM images show good filling of single beads into single wells, and a low occurrence of two beads in one well; this array may seal well and allow large numbers of single beads to be interrogated for the presence of a single analyte. For 3.5-urn deep wells (FIG. 14C), many of the wells contain two beads as well as those that contain one. The presence of a second bead above the plane of the array may deteriorate the sealing of the array as described above and may denigrate the quality of single bead isolation. These experiments indicated that an optimal well depth for 2.8-urn diameter beads, in this embodiment, is between about 3 and about 3.25 urn. While this range is optimal, it is also possible to perform the inventive measurements using well depths of 3.6 urn, i.e., the upper limit as indicated by Eq. (4).

Example 13

Figure 15A:
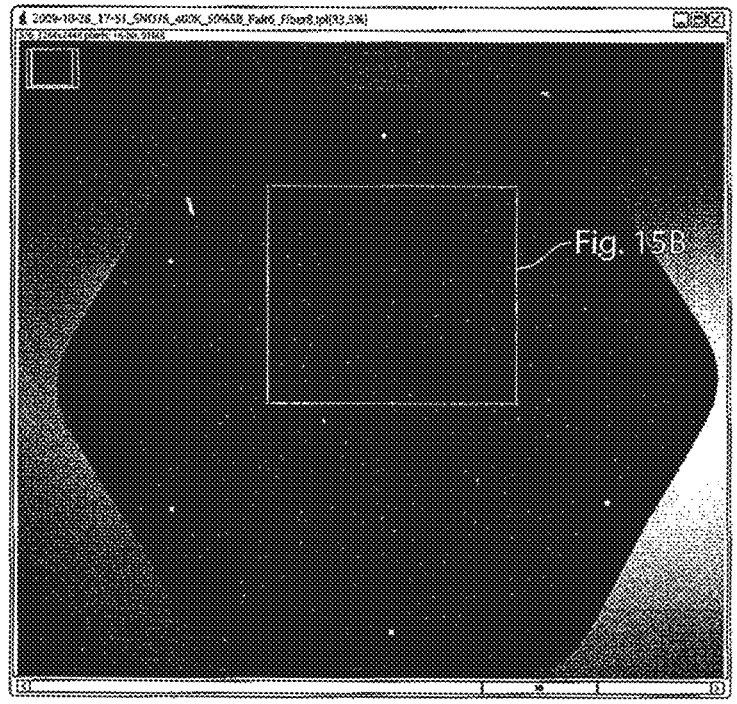
FIG. 15A shows a non-limiting fluorescence image of an array containing beads.
Figure 15B:
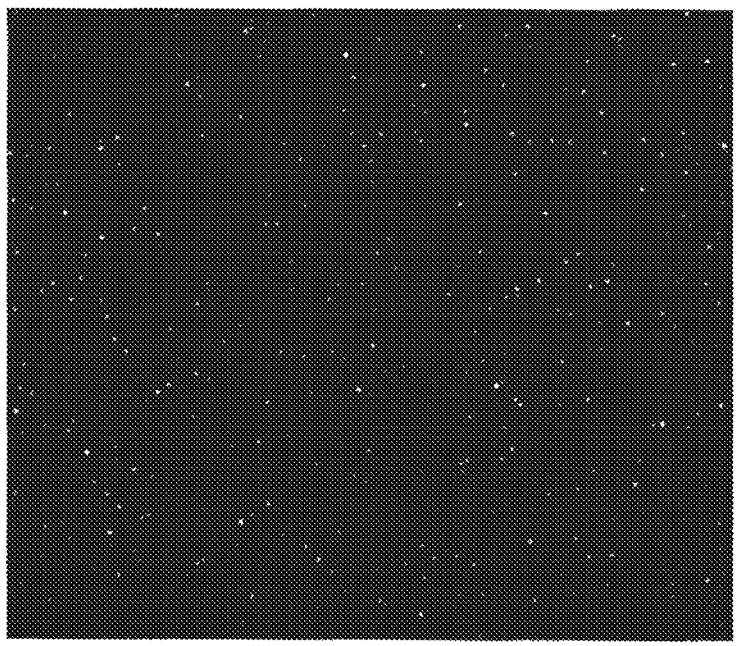
FIG. 15B shows an enlargement of the image from FIG. 15A.
Figure 16A:
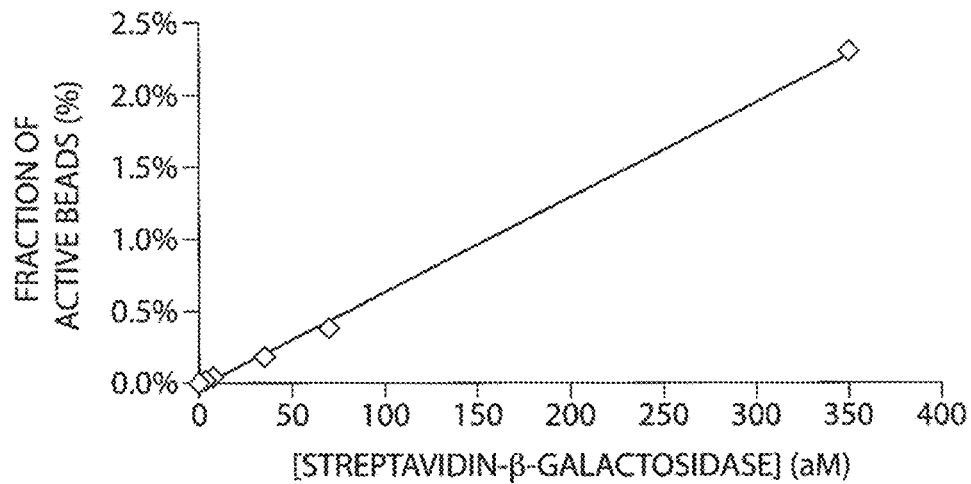
FIGS. 16A and 16B show graphs of the number of reaction vessels determined to contain an analyte molecule versus the concentration of analyte molecules in a fluid sample, according to certain embodiments.
Figure 16B:
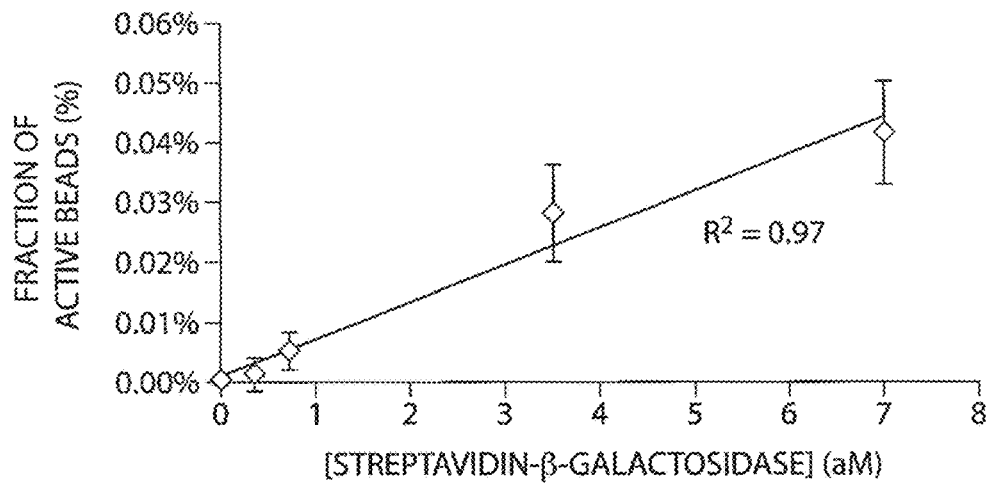
Figure 16C:
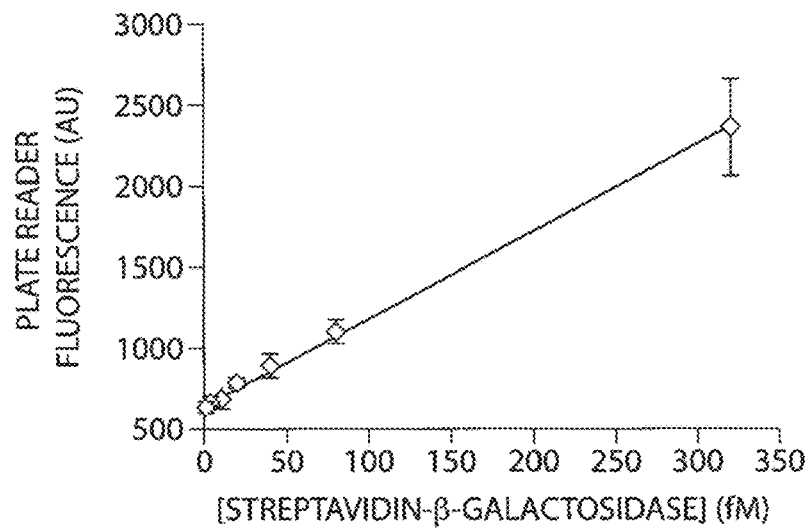
FIG. 16C shows a graph of the total fluorescence read-out versus the concentration of analyte molecules in a fluid sample, according to an exemplary embodiment.

The following example describes the comparison of a non-limiting method of the present invention versus a conventional plate reader for detecting enzyme (see FIGS. 15A, 15B, and 16). Biotin-DNA beads were prepared as described above. These beads were then incubated with a low concentration of SβG such that beads statistically contained either zero or one enzymes. These beads were loaded into microwells, sealed, and imaged as described above; FIGS. 15A and 15B show representative images. In some cases, an increase in sensitivity to enzyme label that comes from isolating single beads is observed as compared to traditional bulk measurements. Beads coated with DNA were prepared, incubated with biotinylated DNA, and then incubated with various concentrations of SβG (from 350 aM to 320 fM) as described above. Enzymes on these beads were then measured in two ways. First, the beads were loaded into microwell arrays, sealed and imaged as described above. The fraction of active wells was determined as described above and is plotted as a function of the concentration of SβG in FIG. 16A, the lower range expanded in FIG. 16B. Second, the beads were incubated with 100 uL of RPG in a microtiter plate for one hour and read on a fluorescence plate reader. The fluorescence signal as a function of the concentration of SβG is plotted in FIG. 16C. The lower limit of detection (LOD) of the inventive method (defined as the concentration at which the signal rises above three standard deviations over the background) in this experiment was 384 zM. The LOD of the bulk measurement on the plate reader was 14.5 fM. The single molecule array approach of the present invention, therefore, provided an increase of 37,760-fold in sensitivity to enzyme label over the plate reader. It should be noted that at the concentrations tested statistically only zero or single analytes should be detected on beads; for example, the ratio of enzymes to beads at 350 aM was 21,070/400,000=0.053.

Example 14

Figure 17:
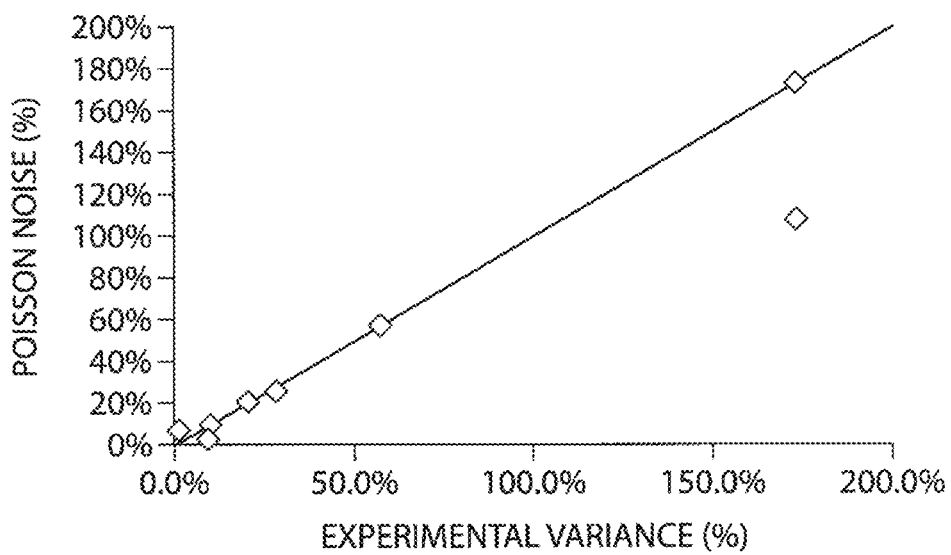
FIG. 17 shows a plot of the % Poisson Noise against the experimental variance over three measurements from the experimental data shown in FIG. 16B.

The following example illustrates the precision of detection in a method as described herein, in a non-limiting embodiment. Detection of single molecules may allow for high precision. In theory, the lowest variance in the measurement is the Poisson noise associated with counting small numbers of events. In this non-limiting example, the % Poisson Noise is given by $\sqrt{N}/N$, where N is the number of active (enzyme-associated) beads. FIG. 17 shows a plot of the % Poisson Noise against the experimental variance over three measurements (% CV) from the experimental data in FIG. 16B. As can be seen, the imprecision of the measurement (% CV) tracks closely with the Poisson Noise, suggesting that the Poisson noise may limit the precision of the methods in some cases.

Example 15

Figure 18:
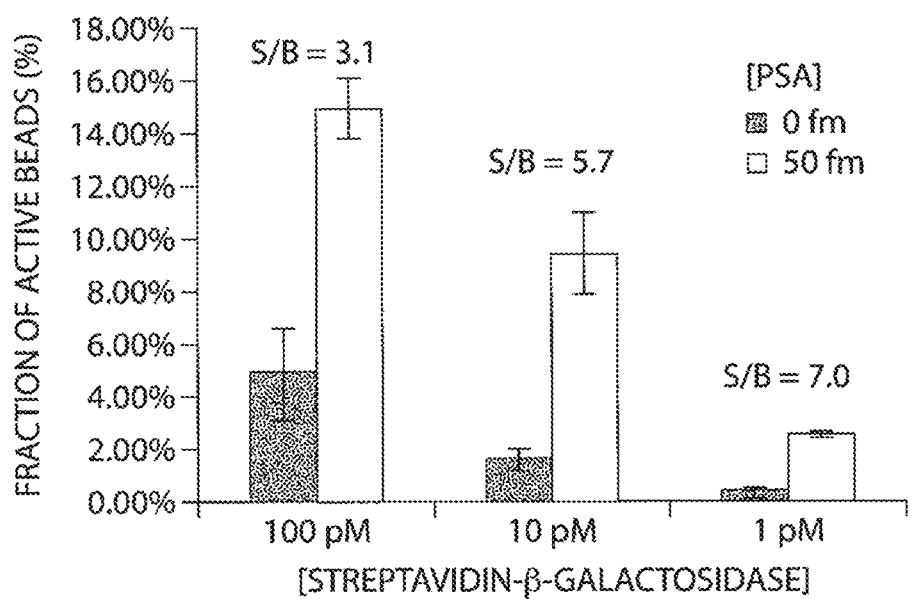
FIG. 18 shows a plot of the fraction of capture objects determined to be associated with an analyte molecule versus the concentration of binding ligand provided, at two concentrations of analyte molecules, according to an exemplary embodiment.

The following non-limiting example describes the detection of PSA in serum (FIG. 18). 2.8-um-diameter beads coated in anti-PSA antibody were prepared as described above. These beads were incubated with 25% bovine serum or 25% bovine serum spiked with 50 fM PSA. The beads were then labeled with anti-PSA detection antibody and three different concentrations of SβG (1, 10, or 100 pM). The beads were then loaded into microwell arrays, sealed and imaged as described above. Image analysis was used to determine the fraction of beads that contained an enzyme. These data show that the invention can be used to detect low concentrations of proteins in serum by performing ELISAs on single beads and detecting single enzyme labels. Because of the high efficiency of the capture of analyte using beads in this invention, the concentration of enzyme label used can be varied to only label a fraction of the analytes captured on the beads in order to optimize the signal-to-background and dynamic range of the measurement. In this data set, 1 pM of enzyme label gave an optimal signal-to-background ratio.

Example 16

Figure 19:
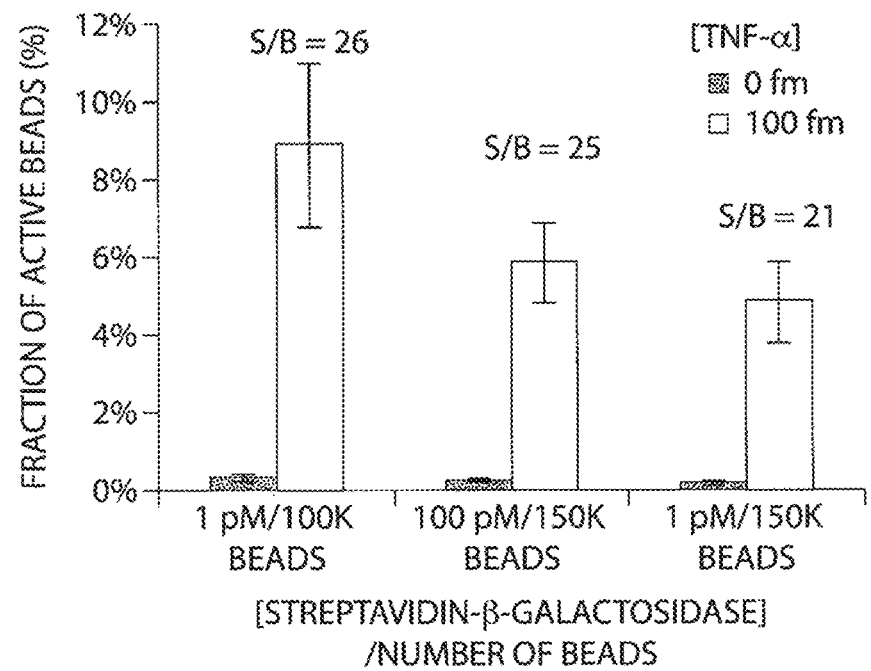
FIG. 19 shows a plot of the fraction of capture objects determined to be associated with an analyte molecule versus the concentration of binding ligand per capture object provided, at two concentrations of analyte molecules, according to an exemplary embodiment.

The following non-limiting example describes the detection of TNF-α (FIG. 19). 2.8-um-diameter beads coated in anti-TNF-α antibody were prepared as described above. These beads were incubated with 25% bovine serum or 25% bovine serum spiked with 100 fM TNF-α. The beads were then labeled with anti-TNF-α detection antibody (e.g., first binding ligand) and two different concentrations of SβG (1 or 100 pM) (e.g., second binding ligand comprising an enzymatic component). The beads were then loaded into microwell arrays, sealed and imaged as described above. Image analysis was used to determine the fraction of beads that contained an enzyme. These data show that the invention can be used to detect low concentrations of TNF-α in serum by performing ELISAs on single beads and detecting single enzyme labels. As in the previous example, the amount of enzyme label can be varied to ensure that the measurement detects only single enzyme labels on the beads and optimize the signal-to-background ratio. In this particular example, the backgrounds are very low so the signal-to-background ratio is optimal at an enzyme label concentration of 1 pM and 100,000 beads.

Example 17

Figure 20:
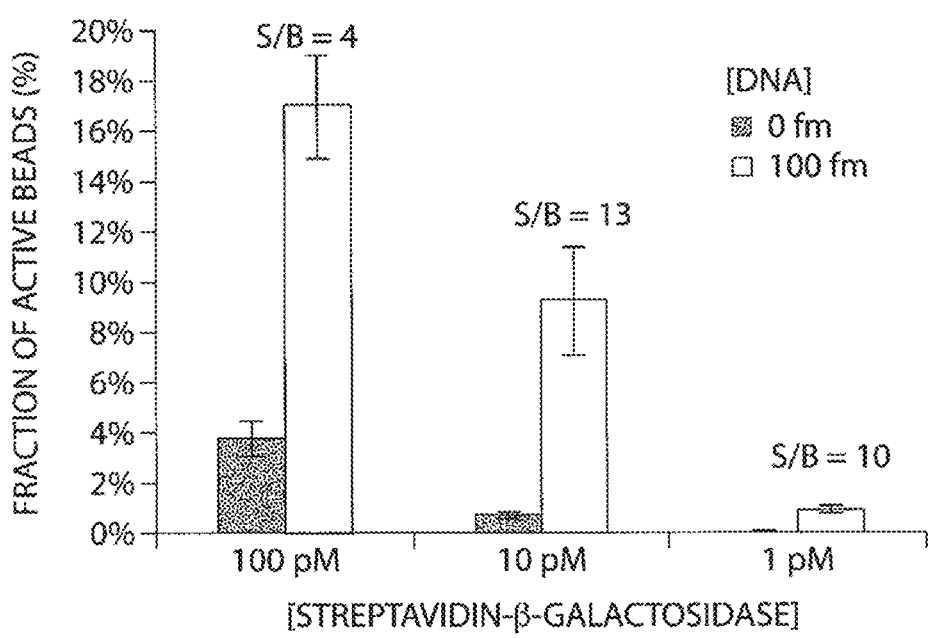
FIG. 20 shows a plot of the fraction of capture objects determined to be associated with an analyte molecule versus the concentration of binding ligand provided, at two concentrations of analyte molecules, according to an exemplary embodiment.

The following non-limiting example describes the detection of DNA in buffer (FIG. 20). 2.7-um-diameter beads functionalized with a capture sequence of DNA were prepared as described as above. These beads were then incubated with various concentrations of target DNA and then labeled with a biotinylated signal probe DNA sequence as described above. The beads were then labeled by incubating with various concentrations of SβG (1, 10, or 100 pM). The beads were then loaded into microwell arrays, sealed and imaged as described above. Image analysis was used to determine the fraction of beads contained an enzyme. These data show that the invention can be used to detect low concentrations of DNA by forming sandwich-like complexes on single beads and detecting single enzyme labels. As in the case of protein detection, the amount of enzyme label can be varied to ensure that there are statistically one or zero enzymes per bead even in the case where there are more than one target DNA molecules captured. This allows the dynamic range and signal-to-background of the single molecule measurement to be optimized. In this case, 10 pM of SβG gave the optimal signal-to-background.

Comparative Example 18

Figure 21:
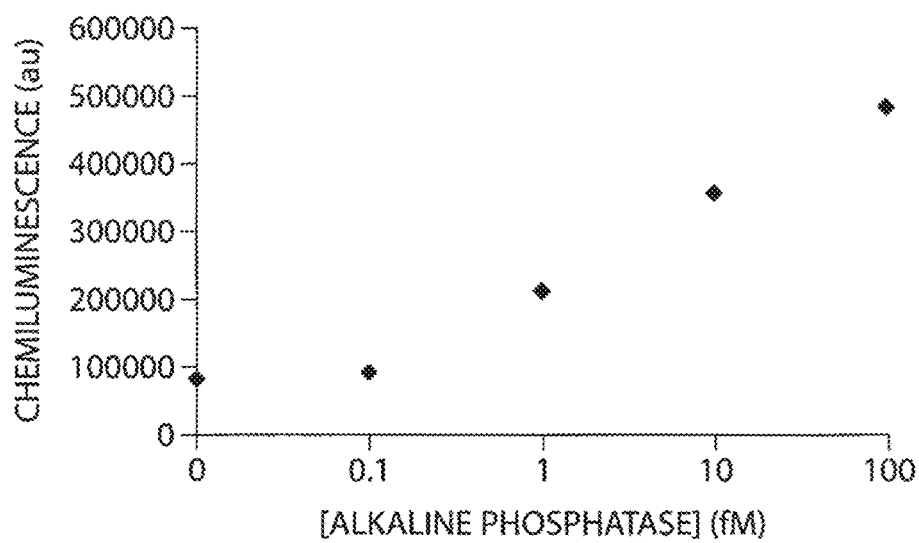
FIG. 21 shows a plot of the total chemiluminescence versus the concentration of binding ligand provided, according to an exemplary embodiment.
Figure 22:
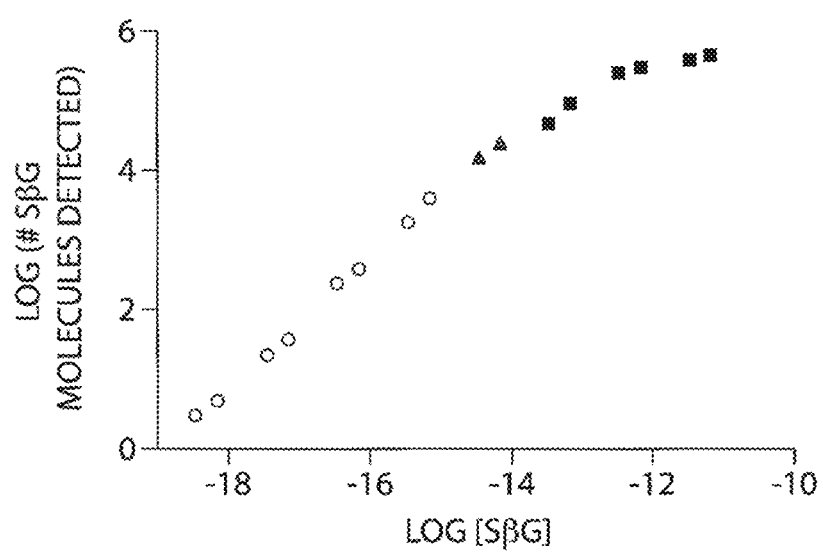
FIG. 22 shows a plot of the log of the fraction of capture objects determined to be associated with an analyte molecule versus the log of the concentration of binding ligand provided, according to an exemplary embodiment.

The following non-limiting example describes a method using detection comprising chemiluminscence from alkaline phosphatase (FIG. 21). Different concentrations of 10 uL of alkaline phosphatase were mixed with 90 uL of a solution containing the most sensitive chemiluminescent substrate available (APS-5; Lumigen Inc.) in a microtiter plate and incubated for 5 mins. The microtiter plate was then read in chemiluminescence mode of a plate reader. FIG. 21 shows a plot of chemiluminescence as a function of concentration of alkaline phosphatase. The lowest concentration of enzyme that could be detected above background was 100 aM and the calculated limit of detection was 50 aM, close to the reported value of 30 aM. Single molecule detection of β-galactosidase on beads in this invention (LOD=220 zM) is, therefore, more than 100 times more sensitive than chemiluminscent detection of alkaline phosphatase, the most sensitive enzyme label system that is commercially available.

Example 19

The clinical use of protein biomarkers for the differentiation of healthy and disease states, and for monitoring disease progression, requires the measurement of low concentrations of proteins in complex samples. Certain current immunoassays can measure proteins at concentrations above $10^{-12}$ M, whereas the concentration of the majority of proteins important in cancer, neurological disorders, and the early stages of infection are thought to circulate in the range from $10^{-16}$ to $10^{-12}$ M. For example: a 1 mm³ tumor composed of a million cells that each secrete 5000 proteins into 5 L of circulating blood translates to ~$2 \times 10^{-15}$ M (or 2 femtomolar, fM); early HIV infection with sera containing 2-3000 virions equates to concentrations of p24 antigen ranging from $60 \times 10^{-18}$ M (60 attomolar, aM) to $15 \times 10^{-15}$ M (15 femtomolar). Attempts to develop protein-based detection methods capable of detecting these concentrations have focused on the replication of nucleic acid labels on proteins, or on measuring the bulk, ensemble properties of labeled protein molecules. Sensitive methods for detecting proteins have, however, lagged behind those for nucleic acids, such as the polymerase chain reaction (PCR), limiting the number of proteins in the proteome that have been detected in blood. The isolation and detection of single protein molecules provides the most direct method for measuring extremely low concentrations of proteins, although the sensitive and precise detection of single protein molecules has proven challenging. The following describes a non-limiting exemplary method for detecting thousands of single protein molecules simultaneously using the same reagents as the gold standard for detecting proteins, namely, the enzyme-linked immunosorbent assay (ELISA). The method can detect proteins in serum at attomolar concentrations and may enable the measurement of a single molecule in blood.

The method makes use of arrays of femtoliter-sized reaction chambers (FIG. 23) that can isolate and detect single enzyme molecules. In the first step, a sandwich antibody complex is formed on microscopic beads, and the bound complexes are labeled with an enzyme reporter molecule, as in a conventional bead-based ELISA. When assaying samples containing extremely low concentrations of protein, the ratio of protein molecules (and the resulting enzyme label complex) to beads is small (typically less than 1:1) and, as such, the percentage of beads that contain a labeled immunocomplex follows a Poisson distribution, leading to single immunocomplexes on individual beads. For example, if 50 aM of a protein in 0.1 mL (3000 molecules) was captured on 200,000 beads, then 1.5% of the beads would have one protein molecule and 98.5% would have zero protein molecules (FIG. 23B). It is typically not possible to detect these low numbers of proteins using conventional detection technology (e.g., a plate reader), because the fluorophores generated by each enzyme diffuse into a large assay volume (typically 0.1-1 mL), and it takes hundreds of thousands of enzyme labels to generate a fluorescence signal above background (FIG. 24A). The method of this Example enables the detection of very low concentrations of enzyme labels by confining the fluorophores generated by individual enzymes to extremely small volumes (~50 fL), leading to a high local concentration of fluorescent product molecules. To achieve this localization in an immunoassay, in the second step of the method the immunoassay beads are loaded into an array of femtoliter-sized wells (FIG. 23B). The loaded array is then sealed against a rubber gasket in the presence of a droplet of fluorogenic enzyme substrate, isolating each bead in a femtoliter reaction chamber. Beads possessing a single enzyme-labeled immunocomplex generate a locally high concentration of fluorescent product in the 50-fL reaction chambers. By using standard fluorescence imaging on a microscope, it is possible to detect single enzyme molecules, and to image tens to hundreds of thousands of immunocomplexes substantially simultaneously. By isolating the enzymes associated with each immunocomplex, each complex can give rise to a high measurable signal which can result in substantially improved sensitivity over bulk measurements. The protein concentration in the test sample, in some cases, is determined by simply counting the number of wells containing both a bead and fluorescent product relative to the total number of wells containing beads (FIG. 23D). The concentration is then determined digitally rather than by using the total analog signal.

Figure 23A:
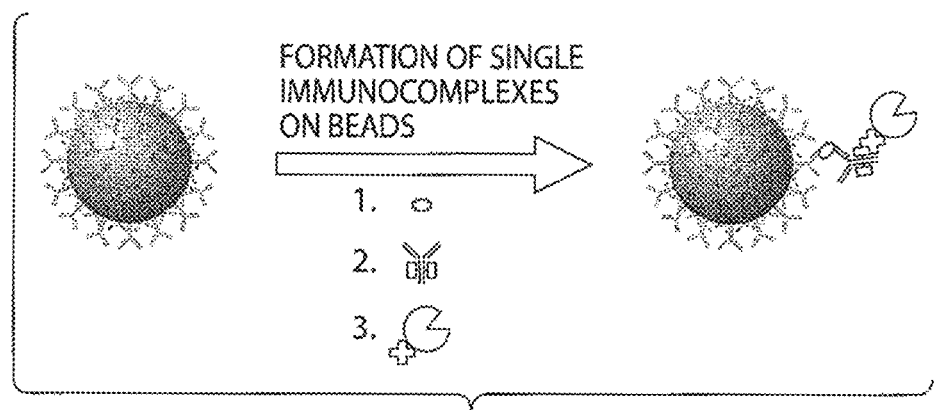
FIGS. 23A and 23B show schematic diagrams depicting one embodiment of steps for performing one method of the present invention.
Figure 23B:
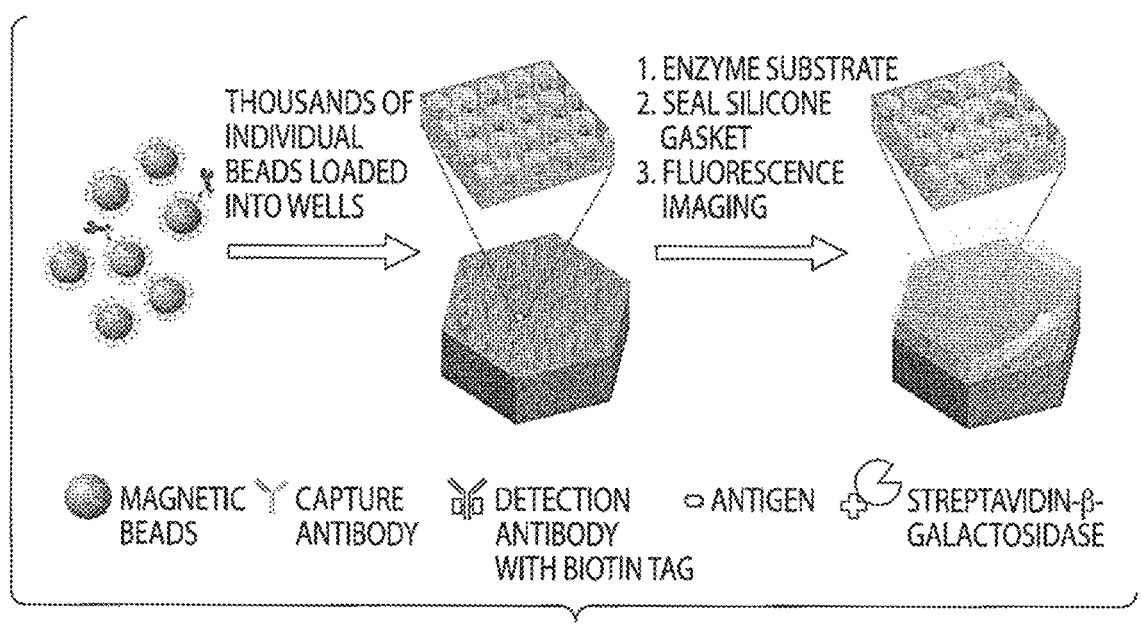
Figure 23C:
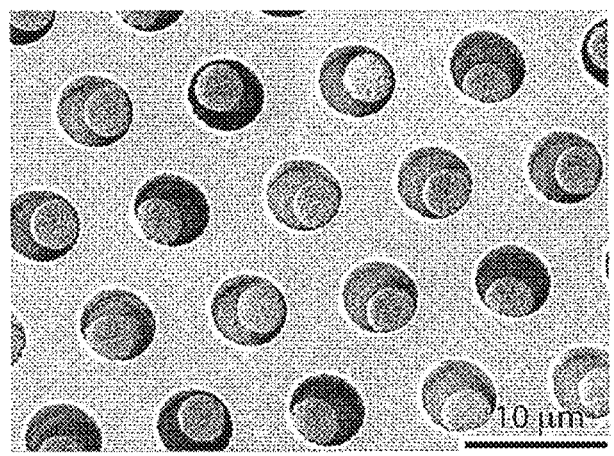
FIG. 23C shows an image of beads contained in a plurality of reaction vessels, according to an exemplary embodiment.
Figure 23D:
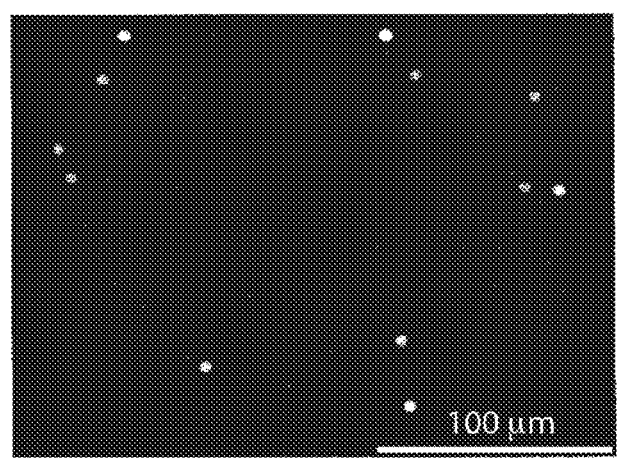
FIG. 23D shows a fluorescence image of an array comprising a plurality of beads, some of which are associated with an analyte molecule following carrying out a method of the present invention, according to an exemplary embodiment.

FIG. 23A shows the capturing and labeling single protein molecules on beads using standard ELISA reagents. FIG. 23B shows the loading of beads into femtoliter microwell arrays for isolation and detection of single molecules. FIG. 23C shows an SEM image of a small section of a femtoliter well array after bead loading. 2.7-µm-diameter beads were loaded into an array of wells with diameters of 4.5 µm and depths of 3.25 µm. FIG. 23D shows a fluorescence image of a small section of the femtoliter well array after signals from single molecules are generated. While the majority of femtoliter chambers contain a bead from the assay, only a fraction of those beads possess catalytic enzyme activity, indicative of a single, bound protein. The concentration of protein in bulk solution may be correlated to the percentage or number of beads that have bound a protein molecule. The exemplary assay was capable of providing linearity over ~4.5 logs for 50,000 beads.

FIG. 24 shows the digitization of enzyme-linked complexes can increase sensitivity substantially compared to bulk, ensemble measurements. FIG. 24 shows a log-log plot of signal output (% active beads for assay comprising the use of capture objects; Relative Fluorescence Units (r.f.u.) for plate reader) as a function of the concentration of SβG. SβG concentrations for the ensemble readout ranged from 3 fM to 300 fM, with a detection limit of $15 \times 10^{-15}$ M (15 fM; line (i)). For the exemplary assay according to the current invention, SβG concentrations ranged from 350 zM to 7 fM, demonstrating a linear response over 4.5 logs, with a detection limit of $220 \times 10^{-21}$ M (220 zM; line (ii)). Error bars are based on the standard deviation over three replicates for both technologies. LODs were determined from the signal at three standard deviations above background. Table 1 provides information regarding the imprecision of this exemplary assay according to the current invention relating to Poisson noise of counting single events. The intrinsic variation (Poisson noise) of counting single active beads is given by fin. Comparing the Poisson noise associated coefficient of variation (% CV) with the % CV for this exemplary assay according to the current invention over three measurements shows that the imprecision of the assay is determined only by counting error. This observation suggests that this assays according to the current invention, in some cases, may have imprecision <20% as long as at least 25 active beads are detected, equating to an enzyme concentration of 4.5 aM.

TABLE 1

| [SbG] (aM) | Average # single complexes | Average % active | Measurement % CV | Poisson % CV |
|---|---|---|---|---|
| 0 | 1 | 0.0016% | 87% | 122% |
| 0.35 | 3 | 0.0086% | 75% | 55% |
| 0.7 | 5 | 0.0099% | 63% | 46% |
| 3.5 | 22 | 0.0413% | 10% | 21% |
| 7 | 38 | 0.0713% | 15% | 16% |
| 35 | 237 | 0.4461% | 1% | 7% |
| 70 | 385 | 0.8183% | 5% | 5% |
| 350 | 1787 | 3.3802% | 2% | 2% |
| 700 | 4036 | 7.5865% | 5% | 2% |
| 3500 | 15634 | 30.6479% | 3% | 1% |
| 7000 | 24836 | 44.5296% | 1% | 1% |

To quantify the potential sensitivity that may be achieved by singulating enzyme-labeled molecules compared to conventional ensemble measurements, a model sandwich assay was developed to capture enzyme molecules on beads; the population of beads were either singulated and read using methods of the current invention, or read as an ensemble population on a conventional plate reader. Beads were functionalized with DNA capture molecules, and subsequently saturated with biotinylated complementary DNA target molecules in a one-step hybridization (see Methods section below). These beads were used to capture various concentrations of an enzyme conjugate, streptavidin-β-galactosidase (SβG), commonly used as a label in ELISA. While the exemplary assay according to the current invention and conventional assay incubations were performed under the substantially similar conditions, in these example the assays diverged at the bead readout step. For the comparative conventional assay, beads were read out in 100 uL on a fluorescence plate reader after 1 h incubation with 100 μM resorufin-β-D-galactopyranoside (RGP), a fluorogenic substrate for β-galactosidase. The detection limit of the capture assay on the microtiter plate reader was 15 fM of SβG (FIG. 24). For single molecule detection according to the present invention, the beads were loaded into the femtoliter arrays and, after sealing a solution of RGP into the wells of the array, signal generated from single enzymes accumulated in the reaction chambers for 2.5 min, with fluorescent images acquired every 30 s. A white light image of the array was acquired at the end of the experiment. These images were analyzed to identify wells that contained beads (from the white light image) and determine which of those beads had an associated enzyme molecule bound (from time-lapsed fluorescent images). FIG. 24 shows a log-log plot of the percentage of beads that contained an enzyme as a function of bulk SβG concentration. The limit of detection (LOD) for the assay according to the invention was 220 zeptomolar (13 molecules in 100 μL, or 22 yoctomoles), corresponding to an improvement in sensitivity over the plate reader of a factor of 68,000, showing that singulation can result in a dramatic increase in sensitivity over conventional ensemble measurements. The concentration of SβG detected using the assay of the present invention was a factor of 140 lower than chemiluminescence detection of alkaline phosphatase (30 aM), the current most sensitive ELISA system. The high thermodynamic and kinetic efficiency that may be achieved for the present process (Table 2) can enable the detection of very low numbers of enzyme labels and indicates that the measurement of a single labeled molecule from blood is a possibility.

TABLE 2

Calculations of the capture efficiency of enzyme label from 0.35 aM to 7000 aM for the assay performed according to the invention (FIG. 24).

| [SβG] (aM) | Column A Average % active beads observed (FIG. 2) | Column B Enzyme/bead ratio from Poisson distribution | Column C Total # of enzymes on 400,000 beads | Column D Background corrected # of enzymes on beads | Column E Calculated # of enzymes in 100-μL sample | Column F Capture Efficiency |
|---|---|---|---|---|---|---|
| 0 | 0.0016% | 0.000016 | 7 | — | — | — |
| 0.35 | 0.0086% | 0.000086 | 34 | 28 | 21 | 132% |
| 0.7 | 0.0099% | 0.000099 | 40 | 33 | 42 | 79% |
| 3.5 | 0.0413% | 0.000413 | 165 | 159 | 211 | 75% |
| 7 | 0.0713% | 0.000713 | 285 | 279 | 421 | 66% |
| 35 | 0.4461% | 0.004471 | 1789 | 1782 | 2107 | 85% |
| 70 | 0.8183% | 0.008217 | 3287 | 3280 | 4214 | 78% |
| 350 | 3.3802% | 0.034387 | 13755 | 13748 | 21070 | 65% |
| 700 | 7.5865% | 0.078897 | 31559 | 31552 | 42140 | 75% |
| 3500 | 30.6479% | 0.365974 | 146390 | 146383 | 210700 | 69% |
| 7000 | 44.5296% | 0.589320 | 235728 | 235722 | 421400 | 56% |

In Table 2, for the experiments, on average 50,000 beads (~12.5%) were interrogated out of the 400,000 incubated with the solutions of enzyme. The low fraction of beads detected was limited by the number of reaction vessels used in this example (50,000 wells). By accounting for bead loss, the number of active beads observed experimentally (Column A) can be used to estimate the total number of active beads out of the 400,000 used (Column B). After background subtraction (Column C) and applying a Poisson distribution adjustment based on the distribution of 0, 1, 2, 3, 4, etc., enzyme molecules per bead, the total number of molecules captured on beads can be determined (Column D). The ratio of this number to the total number of enzymes in 100 uL at the start of the experiment (Column E; volume× concentration×Avogadro's number) yields a capture efficiency (Column F). The overall efficiency of capture and detection of enzyme using the present assay is high (65-85%) and in some embodiments, may be minimally limited in this experiment by the slow diffusion of the large SβG conjugate (MW~515 kDa).

Figure 25A:
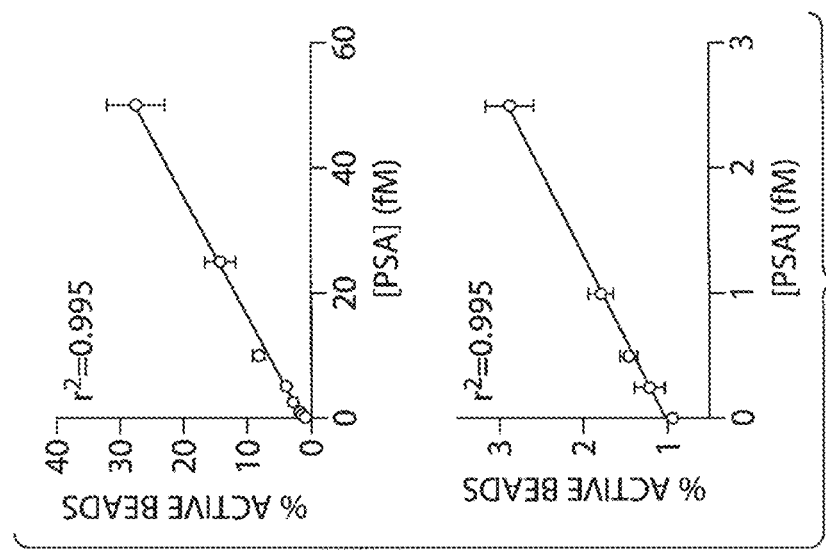
FIG. 25 show plots of the fraction of capture objects determined to be associated with an analyte molecule comprising A) PSA, B) TNF-alpha, or C) DNA, versus the concentration of analyte molecules in a fluid sample, according to an exemplary embodiment.
Figure 25B:
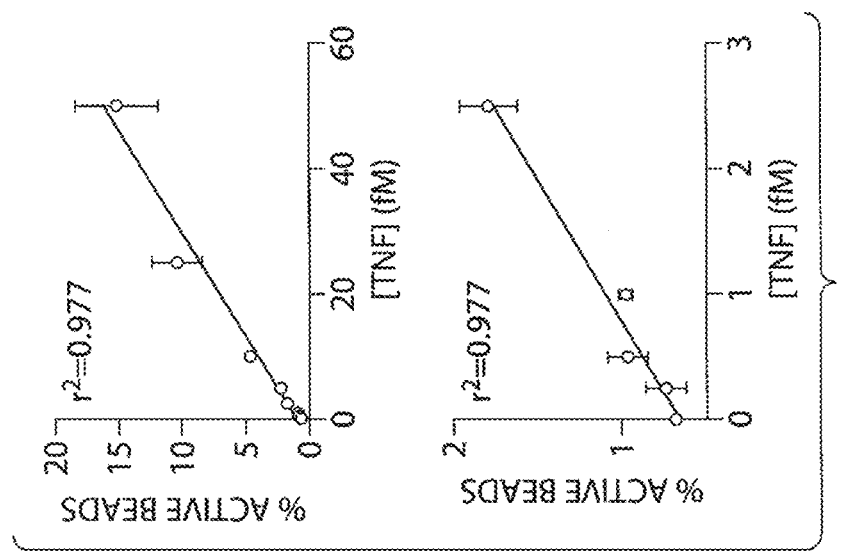
Figure 25C:
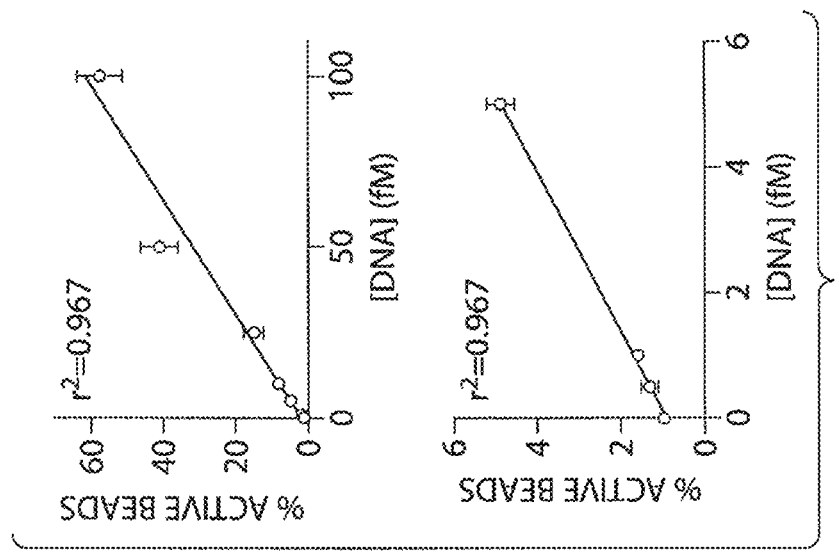

A sandwich-based assay was developed for two clinically-relevant protein biomarkers, namely prostate specific antigen (PSA) and tumor necrosis factor-α (TNF-α). These assays show that the high enzyme label sensitivity of the assay of this Example translates to highly sensitive (<1 fM) assays suitable for detecting proteins in blood. An assay for DNA was also developed to show that the assay of this Example can be used to directly detect single nucleic acid molecules without requiring replication of the target. All assays were performed as outlined in FIG. 23A and FIG. 23B, apart from the DNA assay where a capture sequence and a biotinylated signal sequence were used in place of capture and detection antibodies, respectively. FIGS. 25A-25C show data from the assays for A) PSA, B) TNF-α, and C) DNA. The human forms of the proteins were spiked into 25% bovine serum to be representative of clinical test samples; a four-fold dilution factor was used which may reduce matrix effects in immunoassays. DNA was detected in buffer to be representative of purified nucleic acid preparation techniques. Using digital detection to detect PSA in 25% serum, an LOD of 46 aM (1.5 fg/mL) was attained, equating to 184 aM in whole serum. A leading commercial PSA assay (ADVIA Centaur, Siemens) reports an LOD of 3 pM (0.1 ng/mL) in human serum, and ultra-sensitive assays have been reported with LODs in the range of 10-30 fM. The single molecule assay of the present Example was, therefore, more sensitive than the commercial assay by a factor of 15,000, and more sensitive than other ultra-sensitive methods by a factor of at least 50. The detection limit in the TNF-α determination was 148 aM (2.5 fg/mL), corresponding to 590 aM in whole serum. The highest sensitivity commercially-available ELISA for TNF-α has an LOD of 21 fM (0.34 pg/mL) in serum (Table 1). The assay of the present Example, therefore, imparted an improvement over the most sensitive TNF-α assay of a factor of 35. The LOD of the digital DNA sandwich assay was 135 aM, corresponding to about 8000 copies. The ability of certain assays of the present invention to potentially measure much lower concentrations of proteins compared to conventional techniques arises from the extremely low background signals that may be achieved by digitizing the detection of proteins.

FIGS. 25A-25C shows the attomolar detection of proteins in serum and DNA in buffer using digital detection. Plots of % active beads against analyte concentration for: (FIG. 25A) human PSA spiked into 25% serum, (FIG. 25B) human TNF-α spiked into 25% serum, and (FIG. 25C) DNA in buffer. The bottom row of plots shows the low-end of the concentration range. Assays were performed by sequentially incubating specific capture beads with target solution, biotinylated detector, and SβG conjugate. After completion of the assay, beads were loaded into femtoliter well arrays and interrogated for the presence of single immunocomplexes.

Figure 26:
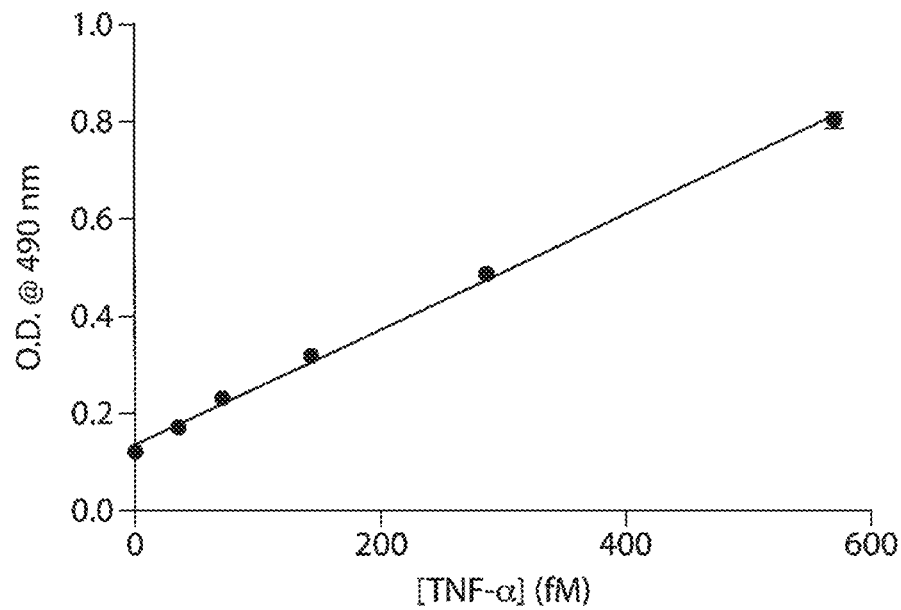
FIG. 26 shows a plot of the optical density versus the concentration of TNF-alpha, according to an exemplary embodiment.

Background in the inventive digital detection immunoassays may arise, at least in part from non-specific binding (NSB) of detection antibody and enzyme conjugate to the capture bead surface (Table 3). Because the inventive assays can provide improved label sensitivity over conventional assays (FIG. 24), significantly less detection antibody (~1 nM) and enzyme conjugate (1-50 pM) can be used to detect binding events compared to conventional assays (labeling reagent concentrations ~10 nM). The decreased label concentration may result in substantially reduced NSB to the capture surface, resulting in much lower background signals and lower LODs. For example, in the TNF-α and PSA determinations as described above, the NSB levels were equivalent to the signal produced by 1.8 fM and 1.2 fM of target protein, respectively. The highest sensitivity commercial TNF-α assay has an NSB level equivalent to 85 fM of TNF-α (FIG. 26), a factor of 50 higher. The ability to reduce backgrounds in certain assays of the present invention by lowering the concentration of labeling reagents can translate to immunoassays with improved sensitivity over conventional assays.

TABLE 3

NSB dropout data.
NSB Dropout Experiment (SiMoA PSA assay)

|  | Average | SD | CV | % NSB | |
|---|---|---|---|---|---|
| No dAb; No PSA | 0.110% | 0.162% | 147% | from SbG | 20% |
| No SbG; No PSA | 0.000% | 0.000% | — | from dAb | 80% |
| NSB | 0.541% | 0.194% | 36% | Total NSB | 100% |

In Table 3, a dropout experiment isolating the sources of NSB in the PSA digital assay. By comparing 'no detection antibody NSB' (No dAb) and 'no SβG NSB' (No SβG) to total NSB (NSB), the contribution of detection antibody and SβG to the NSB of the assay was determined.

Figure 27:
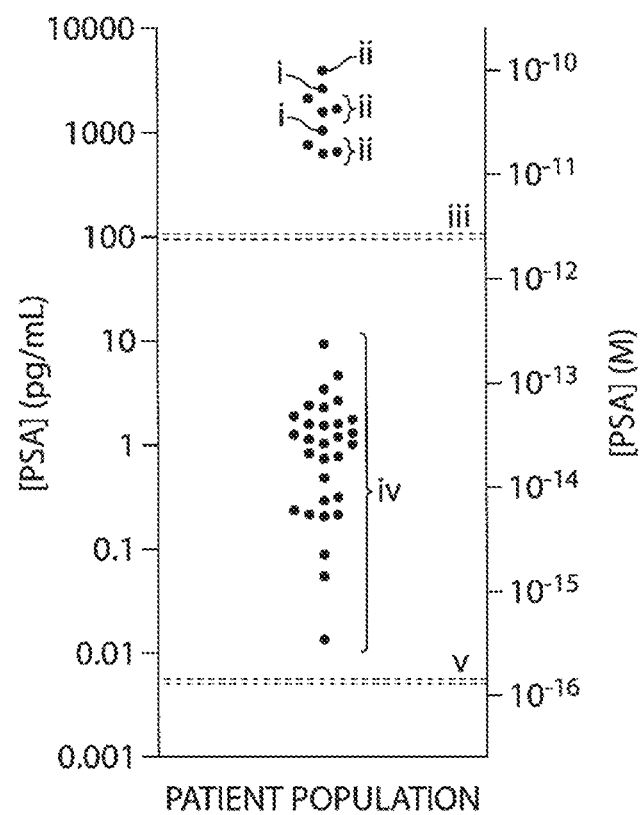
FIG. 27 shows a plot of the concentration of PSA determined for a plurality of human subjects.

To demonstrate the unique diagnostic measurements that could be afforded by detecting single molecules of a protein in human clinical samples, PSA was measured in serum samples from patients who had undergone radical prostatectomy (RP). PSA is a serum biomarker for prostate cancer used as both a screening tool and to monitor for the biochemical recurrence of patients who have undergone radical prostatectomy. After radical prostatectomy, the vast majority of PSA is eliminated, and levels fall below the detection limit of standard commercial assays (3 pM or 0.1 ng/mL). Regular monitoring of these patients for return of PSA can detect recurrence of prostate cancer, but several years may pass post-surgery for biochemical recurrence to be detected by current immunoanalyzers. The ability to accurately quantify PSA levels in post-prostatectomy patients at very low concentrations (<3 fM or 100 fg/mL) may provide early indication of recurrence should PSA levels increase. FIG. 27 shows PSA levels measured using the assay of this Example in the serum of thirty patients (age 60-89) who had undergone radical prostatectomy and whose blood was collected at least 6 weeks post-surgery. The PSA levels in the sera of all 30 patients were below the detection limit of commercial assays. Here, whole serum samples were diluted 1:4 in buffer and measured using the PSA digital assay of this Example (FIG. 25A). PSA was successfully detected in all 30 patients using the present assay. Nine of the thirty samples fell below the LOD of the previously highest sensitivity PSA assay. These data demonstrate a potential clinical utility of certain inventive assays for measuring proteins in serum at concentrations well below the capability of current technology. Table 4 summarizes the patient results.

FIG. 27 shows digital detection of PSA in serum samples of patients who had undergone radical prostatectomy. The concentrations of PSA were determined using the assay of the present Example in serum samples from RP patients (circles (iv)), healthy control samples (circles (ii)), and Bio-Rad PSA control samples (circles (i)). RP patient samples were obtained from SeraCare Life Sciences (Milford, Mass.) and all had undetectable PSA levels as measured by a leading clinical diagnostic assay (ADVIA Centaur); line (iv) represents the detection limit of the ADVIA Centaur PSA assay (100 pg/mL or 3 pM). All 30 patient samples were above the detection limit of the inventive PSA digital assay, shown by the line (v) (0.00584 pg/mL or 184 aM), with the lowest patient PSA concentrations measured at 0.014 pg/mL (420 aM) using the present assay. Patient samples with the lowest PSA levels were detectable, but approached the LOD of the assay resulting in a high dose % CV. The present assay was validated for specificity to PSA using control standards (Bio-Rad) and serum from healthy individuals (ProMedDx) that had been assayed using the ADVIA Centaur PSA assay (See Table 5).

TABLE 4

Summary of Patient Results

| Patient ID | [PSA] (pg/mL) | Dose % CV |
|---|---|---|
| S600 | 9.39 | 6% |
| S599 | 0.75 | 10% |
| S598 | 2.71 | 12% |
| S597 | 1.79 | 12% |
| S596 | 2.46 | 17% |
| S595 | 0.32 | 21% |
| S594 | 1.63 | 15% |
| S593 | 1.15 | 12% |
| S592 | 3.46 | 9% |
| S591 | 0.21 | 25% |
| S590 | 0.22 | 22% |
| S589 | 0.85 | 17% |
| S588 | 2.33 | 3% |
| S587 | 1.06 | 13% |
| 5586 | 1.29 | 22% |
| S585 | 0.49 | 84% |
| S584 | 0.056 | 136% |
| S583 | 1.33 | 26% |
| S582 | 4.76 | 9% |
| S581 | 1.57 | 31% |
| S580 | 0.30 | 4% |
| S579 | 1.22 | 15% |
| S578 | 0.090 | 91% |
| S577 | 1.92 | 6% |
| S576 | 0.014 | 286% |
| S575 | 0.79 | 63% |
| S574 | 1.62 | 20% |
| S573 | 0.22 | 32% |
| S572 | 1.04 | 20% |
| S571 | 0.24 | 21% |

TABLE 5

| | Centaur (ng/mL) | Assay Method of the present invention (ng/mL) |
|---|---|---|
| Bio-Rad Control 1 | 0.838 | 1.06 ± 0.21 |
| Bio-Rad Control 2 | 2.47 | 2.66 ± 0.36 |
| Normals | | |
| ProMedDx S376 | 2.1 | 1.60 |
| ProMedDx S378 | 2.3 | 1.70 |
| ProMedDx S381 | 2.9 | 2.14 |
| ProMedDx S388 | 4.1 | 3.95 |
| ProMedDx S395 | 0.93 | 0.63 |
| ProMedDx S396 | 0.9 | 0.77 |
| ProMedDx S397 | 1.2 | 0.66 |

Table 5 shows the specificity of the present assay was confirmed using PSA samples from Bio-Rad (controls) and ProMedDx (serum from healthy individuals) that had previously been tested on a commercial immunoanalyzer (ADVIA Centaur, Siemens). The PSA concentrations of the healthy serum samples determined using the exemplary method were (24±12)% lower than those originally determined on the ADVIA Centaur. There are two possible explanations for this systematic bias between the two technologies. First, the ADVIA Centaur values were obtained on fresh serum, whereas values for the present assay were obtained after the sera had been frozen for extended periods of time and had experienced a freeze-thaw cycle. Second, there may be differences between the PSA calibrators used to generate the calibration curves that would result in differences in PSA concentrations determined. Complex PSA from the World Health Organization (WHO) was used as calibrators; the ADVIA Centaur calibration PSA is unknown.

By isolating and detecting single immunocomplexes formed in ELISA, certain assays of the invention can impart sensitivity, precision, and dynamic range improvements over standard readout methods and other known ultrasensitive approaches. While certain of the inventive assays can provide sensitivity below the detectable limit of standard and ultra-sensitive readout formats in serum, potentially two more logs of sensitivity may be available based on the enzyme label LOD (FIG. 24). The ability to isolate and interrogate single molecules on individual beads according to certain embodiments of the invention may facilitate distinguishing true antibody-antigen binding events from non-specifically bound complexes. Identifying and differentiating these two populations may permit the detection of a single biomarker molecule in a human serum sample.

Capture of Proteins on Magnetic Beads and Formation of Enzyme-Labeled Immunocomplex (FIGS. 25 and 27).

Beads functionalized with an antibody to the target protein were prepared according to the manufacturer's instructions. Test solutions containing the protein of interest were incubated with suspensions of 200,000 magnetic beads for 2 h at room temperature. The beads were then separated and washed three times in PBS and 0.1% Tween-20. The beads were resuspended and incubated with solutions containing detection antibody (typically, 1-3 nM) for 45 min at room temperature. The beads were then separated and washed three times in PBS and 0.1% Tween-20. The beads were incubated with solutions containing SβG (1-50 pM) for 30 min at room temperature, separated, and washed six times in PBS and 0.1% Tween-20. The beads were then resuspended in 10 μL of PBS and loaded onto a femtoliter well array.

Example 20

Figure 28:
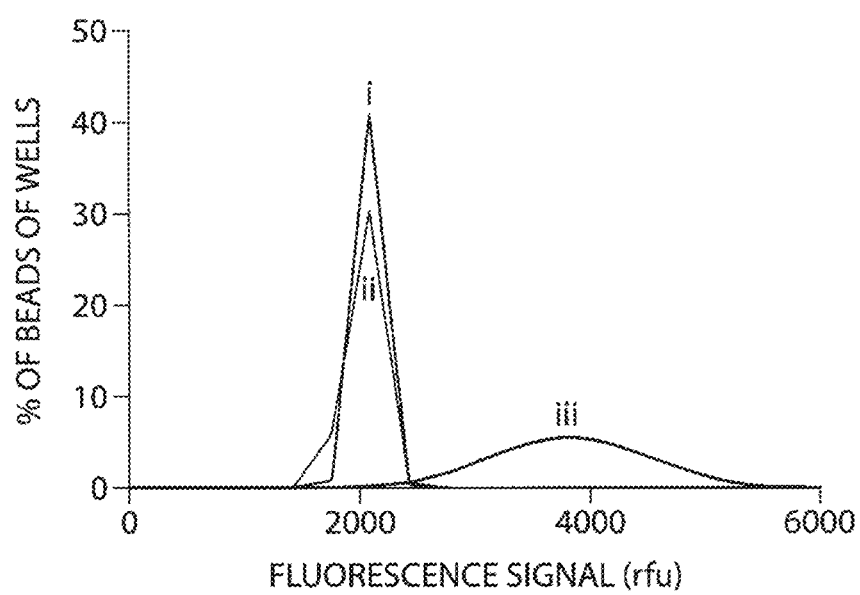
FIG. 28 shows a histogram of the average fluorescence intensity of reaction vessels in an assay method, according to one embodiment of the present invention.

FIG. 28 shows a histogram of the average fluorescence intensity of reaction vessels in an experiment of the present invention. A representative set of images from the experiment were analyzed to determine populations of reaction vessels that: (i) contained no beads; (ii) contained a bead (from white light scatter) but no enzyme (no increase in fluorescence intensity); and, (iii) contained a bead (from white light scatter) and an enzyme (increasing fluorescence intensity over four consecutive images, and an overall increase in fluorescence of at least 20%). Specifically, line (i) represents data from empty reaction vessels, line (ii) represents reaction vessels with a bead but no enzyme ("off" beads), and line (iii) represents reaction vessels with both a bead and enzymatic activity ("on" beads).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed:

1. A method for determining a measure of a concentration of analyte molecules or particles in a fluid sample, comprising:
    exposing a plurality of capture objects to a solution containing or suspected of containing at least one type of analyte molecules or particles;
    immobilizing analyte molecules or particles with respect to the plurality of capture objects such that at least some of the capture objects associate with at least one analyte molecule or particle and a statistically significant fraction of the capture objects do not associate with any analyte molecule or particle;
    spatially segregating at least a portion of the capture objects subjected to the immobilizing step into a plurality of separate locations;
    addressing at least a portion of the plurality of locations subjected to the spatially segregating step and determining a measure indicative of a number or fraction of said locations containing at least one analyte molecule or particle, wherein determining the measure indicative of the number or fraction of said locations containing at least one analyte molecule or particle comprises use of one or more detection methods comprising one or both of:
        a) replicating a nucleic acid precursor, and
        b) converting a nucleic acid precursor to a nucleic acid that can be readily detected; and
    determining a measure of the concentration of analyte molecules or particles in the fluid sample based at least in part on the measure indicative of the number or fraction of locations determined to contain at least one analyte molecule or particle.

2. The method of claim 1, wherein the addressing step comprises determining the number of said locations containing at least one analyte molecule or particle.

3. The method of claim 2, wherein the step of determining the measure of the concentration of analyte molecules or particles in the fluid sample is based at least in part on a Poisson distribution analysis of the number or fraction of locations determined to contain at least one analyte molecule or particle.

4. The method of claim 1, wherein the addressing step comprises determining the fraction of said locations containing at least one analyte molecule or particle.

5. The method of claim 1, wherein the capture objects exposed to the solution each include a binding surface having affinity for the at least one type of analyte molecule or particle.

6. The method of claim 5, wherein determining the measure indicative of the number or fraction of said locations containing at least one analyte molecule or particle comprises replicating a nucleic acid precursor.

7. The method of claim 5, wherein determining the measure indicative of the number or fraction of said locations containing at least one analyte molecule or particle comprises converting a nucleic acid precursor to a nucleic acid that can be readily detected.

8. The method of claim 5, wherein determining the measure indicative of the number or fraction of said locations containing at least one analyte molecule or particle comprises determining a measure indicative of a number or fraction of locations comprising replicated nucleic acids.

9. The method of claim 5, wherein determining the measure indicative of the number or fraction of said locations containing at least one analyte molecule or particle comprises determining a measure indicative of a number or fraction of locations comprising nucleic acids that can be readily detected.

10. The method of claim 5, wherein determining the measure indicative of the number or fraction of said locations containing at least one analyte molecule or particle comprises detecting a fluorescence signal.

11. The method of claim 5, wherein at least a portion of the analyte molecules or particles are associated with at least one binding ligand.

12. The method of claim 5, wherein determining the measure indicative of the number or fraction of said locations containing at least one analyte molecule or particle comprises using a nucleic acid-based technique chosen from one or more of: polymerase chain reaction (PCR), rolling circle amplification (RCA), ligation, and loop-mediated isothermal amplification (LAMP).

13. The method of claim 5, wherein the plurality of locations comprises a plurality of reaction vessels.

14. The method of claim 13, wherein the reaction vessels of the plurality of reaction vessels each have a volume between 10 attoliters and 100 picoliters.

15. The method of claim 5, wherein the analyte molecules or particles are proteins.

16. The method of claim 5, wherein the analyte molecules or particles are nucleic acids.

17. The method of claim 5, wherein determining the measure indicative of the number or fraction of said locations containing at least one analyte molecule or particle comprises using polymerase chain reaction (PCR).

18. The method of claim 5, wherein determining the measure indicative of the number or fraction of said locations containing at least one analyte molecule or particle comprises using rolling circle amplification (RCA).

19. The method of claim 5, wherein at least some of the plurality of separate locations contain only a single capture object.

20. The method of claim 5, wherein the plurality of capture objects that include a binding surface having affinity for the at least one type of analyte molecule or particle comprises a plurality of beads.

\* \* \* \* \*